US008163535B2

(12) United States Patent
Reed et al.

(10) Patent No.: US 8,163,535 B2
(45) Date of Patent: Apr. 24, 2012

(54) DEVICES AND PROCESSES FOR NUCLEIC ACID EXTRACTION

(75) Inventors: Michael W. Reed, Lake Forest Park, WA (US); Oliver Z. Nanassy, Edmonds, WA (US); Paul V. Haydock, Shoreline, WA (US); Nigel Rudra Sharma, Bothell, WA (US); Ronald L. Bardell, Minneapolis, MN (US); Perry Hargrave, Lynnwood, WA (US)

(73) Assignee: Blood Cell Storage, Inc., Seattle, WA (US)

( * ) Notice: Subject to any disclaimer, the term of this patent is extended or adjusted under 35 U.S.C. 154(b) by 396 days.

(21) Appl. No.: 12/348,244

(22) Filed: Jan. 2, 2009

(65) Prior Publication Data
US 2009/0215125 A1 Aug. 27, 2009

Related U.S. Application Data

(63) Continuation-in-part of application No. 11/768,076, filed on Jun. 25, 2007, now Pat. No. 7,608,399.

(60) Provisional application No. 60/816,577, filed on Jun. 26, 2006, provisional application No. 60/910,609, filed on Apr. 6, 2007, provisional application No. 61/018,621, filed on Jan. 2, 2008, provisional application No. 61/052,089, filed on May 9, 2008, provisional application No. 61/093,648, filed on Sep. 2, 2008, provisional application No. 61/111,079, filed on Nov. 4, 2008.

(51) Int. Cl.
*C12M 1/00* (2006.01)
*C12M 1/36* (2006.01)
*G01N 15/06* (2006.01)
*C07H 21/04* (2006.01)

(52) U.S. Cl. ............... 435/283.1; 435/287.2; 435/288.5; 422/68.1; 422/81; 422/505; 422/527; 536/23.1

(58) Field of Classification Search .................. None
See application file for complete search history.

(56) References Cited

U.S. PATENT DOCUMENTS

| 4,883,867 A | 11/1989 | Lee |
| 5,155,018 A | 10/1992 | Gillespie |
| 5,234,809 A | 8/1993 | Boom |
| 5,405,519 A | 4/1995 | Schwartz |

(Continued)

FOREIGN PATENT DOCUMENTS

EP 0430 248 A2 6/1991

(Continued)

OTHER PUBLICATIONS

Sigma-Aldrich catalog, 200-2001, p. 109.*

(Continued)

*Primary Examiner* — Betty Forman
(74) *Attorney, Agent, or Firm* — Christensen O'Connor Johnson Kindness PLLC

(57) ABSTRACT

Devices, processes, and kits for the extraction of nucleic acids from biological samples are disclosed. The devices comprise a first port, a second port, and a binding chamber intermediate and in fluid communication with the first port and the second port. The binding chamber comprises an unmodified flat glass surface effective for binding a heterogeneous population of nucleic acids. The first port, second port, and binding chamber define a continuous fluid pathway that is essentially free of nucleic acid-specific binding sites.

27 Claims, 12 Drawing Sheets

U.S. PATENT DOCUMENTS

| | | | |
|---|---|---|---|
| 5,587,128 | A | 12/1996 | Wilding |
| 5,599,664 | A | 2/1997 | Schwartz |
| 5,658,548 | A | 8/1997 | Padhye |
| 5,720,928 | A | 2/1998 | Schwartz |
| 5,808,041 | A | 9/1998 | Padhye |
| 5,994,056 | A | 11/1999 | Higuchi |
| 6,147,198 | A | 11/2000 | Schwartz |
| 6,150,089 | A | 11/2000 | Schwartz |
| 6,168,948 | B1 | 1/2001 | Anderson |
| 6,171,785 | B1 | 1/2001 | Higuchi |
| 6,174,671 | B1 | 1/2001 | Anantharaman |
| 6,194,562 | B1 | 2/2001 | Smith |
| 6,218,531 | B1 | 4/2001 | Ekenberg |
| 6,294,136 | B1 | 9/2001 | Schwartz |
| 6,340,567 | B1 | 1/2002 | Schwartz |
| 6,377,721 | B1 | 4/2002 | Walt |
| 6,383,393 | B1 | 5/2002 | Colpan |
| 6,448,012 | B1 | 9/2002 | Schwartz |
| 6,489,112 | B1 | 12/2002 | Hadd |
| 6,509,158 | B1 | 1/2003 | Schwartz |
| 6,610,256 | B2 | 8/2003 | Schwartz |
| 6,617,105 | B1 | 9/2003 | Rudi |
| 6,649,378 | B1 | 11/2003 | Kozwich |
| 6,713,263 | B2 | 3/2004 | Schwartz |
| 6,720,417 | B1 | 4/2004 | Walter |
| 6,814,934 | B1 | 11/2004 | Higuchi |
| 6,821,757 | B2 | 11/2004 | Sauer |
| 7,173,124 | B2 | 2/2007 | Deggerdal |
| 7,238,530 | B2 | 7/2007 | Goudsmit |
| 7,416,892 | B2 | 8/2008 | Battrell |
| 2001/0026921 | A1 | 10/2001 | Rabbani |
| 2002/0006623 | A1 | 1/2002 | Bradley |
| 2002/0025529 | A1* | 2/2002 | Quake et al. ............ 435/6 |
| 2002/0155586 | A1 | 10/2002 | Cheng |
| 2002/0157119 | A1 | 10/2002 | Beachy |
| 2002/0164816 | A1 | 11/2002 | Quake |
| 2003/0138941 | A1 | 7/2003 | Gong |
| 2004/0014070 | A1 | 1/2004 | Pinsl-Ober |
| 2004/0086930 | A1 | 5/2004 | Tereba |
| 2004/0122222 | A1 | 6/2004 | Sakurai |
| 2004/0152085 | A1 | 8/2004 | Terlesky |
| 2004/0215011 | A1 | 10/2004 | Deggerdal |
| 2005/0142565 | A1 | 6/2005 | Samper |
| 2005/0191760 | A1 | 9/2005 | Heath |
| 2005/0211559 | A1 | 9/2005 | Kayyem |
| 2005/0214765 | A1 | 9/2005 | Reitan |
| 2006/0029972 | A1 | 2/2006 | Lorenz |
| 2006/0166223 | A1* | 7/2006 | Reed et al. ............ 435/6 |
| 2006/0216239 | A1 | 9/2006 | Zhang |

FOREIGN PATENT DOCUMENTS

| | | | |
|---|---|---|---|
| EP | 1234832 B1 | 8/2002 | |
| EP | 1388588 A1 | 2/2004 | |
| EP | 1529841 B1 | 5/2005 | |
| EP | 1607748 A1 | 12/2005 | |
| WO | 99/09042 A2 | 2/1999 | |
| WO | 0040697 A1 | 7/2000 | |
| WO | 0222265 A1 | 3/2002 | |
| WO | 2004040001 A2 | 5/2004 | |
| WO | 2004061085 A2 | 7/2004 | |
| WO | WO 2004/071662 | * | 8/2004 |
| WO | 2005007895 A1 | 1/2005 | |
| WO | 2005/066343 A1 | 7/2005 | |
| WO | 2005073691 A1 | 8/2005 | |

OTHER PUBLICATIONS

Sigma-Aldrich, DNA Quantitation Kit, Technical Bulletin, 2001, pp. 1-4.*

Duncan, R.E., and P.T. Gilham, "Isolation of Transfer RNA Isoacceptors by Chromatography on Dihydroxyboryl-Substituted Cellulose, Polyacrylamide, and Glass," Analytical Biochemistry 66(2):532-539, Jun. 1975.

Gobbers, E., et al., "Efficient Extraction of Virus DNA by NucliSens Extractor Allows Sensitive Detection of Hepatitis B Virus by PCR," Journal of Clinical Microbiology 39(12):4339-4343, Dec. 2001.

Legendre, L.A., et al., "A Simple, Valveless Microfluidic Sample Preparation Device for Extraction and Amplification of DNA From Nanoliter-Volume Samples," Analytical Chemistry 78(5):1444-1451, Mar. 2006.

Malic, L., et al., "Current State of Intellectual Property in Microfluidic Nucleic Acid Analysis," Recent Patents on Engineering 1(1):71-88, Feb. 2007.

McCaustland, K.A., et al., "Application of Two RNA Extraction Methods Prior to Amplification of Hepatitis E Virus Nucleic Acid by the Polymerase Chain Reaction," Journal of Virological Methods 35(3):331-342, Dec. 1991.

Nanassy, O.Z., et al., "Capture of Genomic DNA on Glass Microscope Slides," Analytical BioChemistry 365(2):240-245, Jun. 2007.

Rohland, N., and M. Hofreiter, "Comparison and Optimization of Ancient DNA Extraction," BioTechniques 42(3):343-352, Mar. 2007.

Steiner, J.J., et al., "A Rapid One-Tube Genomic DNA Extraction Process for PCR and RAPD Analyses," Nucleic Acids Research 23(13):2569-2570, Jul. 1995.

Thompson, J.D., et al., "Extraction of Cellular DNA From Crude Cell Lysate With Glass," Nucleic Acids Research 18(4):1074, Feb. 1990.

Tian, H., et al., "Evaluation of Silica Resins for Direct and Efficient Extraction of DNA from Complex Biological Matrices in a Miniaturized Format," Analytical Biochemistry 283(2):175-191, Aug. 2000.

Wolfe, K.A., "Toward a Microchip-Based Solid-Phase Extraction Method for Isolation of Nucleic Acids," Electrophoresis 23(5):727-733, Mar. 2002.

Zhong, R., et al., "Fabrication of Two-Weir Structure-Based Packed Columns for On-Chip Solid-Phase Extraction of DNA," Electrophoresis 28(16):2920-2926, Aug. 2007.

Bhattacharyya, A., and C.M. Klapperich, "Thermoplastic Microfluidic Device for On-Chip Purification of Nucleic Acids for Disposable Diagnostics," Analytical Chemistry 78(3):788-792, Feb. 2006.

Boom, R., et al., "Rapid and Simple Method for Purification of Nucleic Acids," Journal of Clinical Microbiology 28(3):495-503, Mar. 1990.

Breadmore, M.C., et al., "Microchip-Based Purification of DNA from Biological Samples," Analytical Chemistry 75(8):1880-1886, Apr. 2003.

Cady, N.C., et al., "Nucleic Acid Purification Using Microfabricated Silicon Structures," Biosensors & Bioelectronics 19(1):59-66, Oct. 2003.

Nakagawa, T., et al., "Fabrication of Amino Silane-Coated Microchip for DNA Extraction From Whole Blood," Journal of Biotechnology 116(2):105-111, Mar. 2005.

Vogelstein, B., and D. Gillespie, "Preparative and Analytical Purification of DNA From Agarose," PNAS (Proceedings of the National Academy of Sciences USA) 76(2):615-619, Feb. 1979.

Kim, J.-H., et al., "A Disposable DNA Sample Preparation Microfluidic Chip for Nucleic Acid Probe Assay," Proceedings of the 15th IEEE International Conference on Micro Electro Mechanical Systems, Las Vegas, Jan. 20-24, 2002, pp. 133-136.

Lee, C.-Y., Jr., et al., "Integrated Microfluidic Systems for DNA Analysis," Proceedings of the 2004 IEEE International Conference on Robotics and Biomimetics, Shenyang, China, Aug. 22-26, 2004, pp. 284-289.

Liu, W.-T., and L. Zhu, :Environmental Microbiology-on-a-Chip and Its Future Impacts, Trends in Biotechnology 23(4):174-179, Apr. 2005.

Münchow, G., et al., "Automated Chip-Based Device for Simple and Fast Nucleic Acid Amplification," Expert Review of Molecular Diagnostics 5(4):613-620, Jul. 2005.

Waters, L.C., et al., "Microchip Device for Cell Lysis, Multiplex PCR Amplification, and Electrophoretic Sizing," Analytical Chemistry 70(1):158-162, Jan. 1998.

Weigl, B.H., et al., "Lab-on-a-Chip for Drug Development," Advanced Drug Delivery Reviews 55(3):349-377, Feb. 2003.

Gao, J., and M.B. Chan-Park, "Adhesive Behavior of DNA Molecules on Silicon Wafers Treated by Argon and Oxygen Plasma," Surface and Coatings Technology 194(2-3):244-250, May 2005.

* cited by examiner

DEVICES AND PROCESSES FOR NUCLEIC ACID EXTRACTION

CROSS-REFERENCE TO RELATED APPLICATIONS

This application is a continuation-in-part of U.S. patent application Ser. No. 11/768,076, filed Jun. 25, 2007, which claims the benefit of U.S. Provisional Application No. 60/816,577, filed Jun. 26, 2006, and U.S. Provisional Application No. 60/910,609, filed Apr. 6, 2007, each of which is incorporated herein by reference in its entirety. This application claims the benefit of U.S. Provisional Application No. 61/018,621, filed Jan. 2, 2008, U.S. Provisional Application No. 61/052,089, filed May 9, 2008, U.S. Provisional Application No. 61/093,648, filed Sep. 2, 2008, and U.S. Provisional Application No. 61/111,079, filed Nov. 4, 2008, each of which is incorporated herein by reference in its entirety.

BACKGROUND OF THE INVENTION

Rapid analysis of nucleic acids from biological samples has been advanced by the development of microfluidic technologies capable of extracting nucleic acids from cell lysates and other sources. Rapid extraction methodologies can be combined with amplification techniques such as polymerase chain reaction (PCR) to provide useful quantities of nucleic acids from minute samples of blood, tissue, cultured cells, or other biological materials. These microfluidic technologies have been widely adopted in biomedical research laboratories, permitting, for example, high-throughput screening of cloned DNA "libraries" from cultured bacteria or other host cells.

Commonly used methods for extracting DNA on such a small scale exploit the tendency for DNA to bind to materials such as silica gel, silica membranes, porous glass, or diatomaceous earth. One such system provides a microcentrifuge tube containing the DNA-binding media (known as a "spin column"). The sample is loaded into the tube and spun in a centrifuge, whereby the DNA is captured and the liquid phase containing contaminants passes through to the bottom of the tube. Such a procedure is disclosed in, for example, U.S. Pat. No. 6,821,757 to Sauer et al. Although spin column technology has been widely adopted by the research community, the resulting DNA is often of low quality for use in downstream applications such as PCR, and the need to pipette multiple samples into open tubes results in a significant risk of sample contamination. Moreover, such methods are time consuming when performed manually and very expensive to automate.

The successful use of rapid DNA extraction techniques in research has led to an interest in developing devices and processes through which this technology can be used in medical applications such as point-of-care diagnosis or testing of blood components. Recent progress toward more simple and compact devices has been reviewed by Malic et al., *Recent Patents on Engineering* 1:71-88, 2007. Despite these recent advances, there remains a need in the art for devices and processes by which high-quality DNA and RNA can be rapidly and economically extracted from biological samples.

SUMMARY OF THE INVENTION

The present invention provides devices, processes and kits that are useful for the extraction of nucleic acids, including DNA and RNA, from liquid samples.

One aspect of the invention provides a device comprising (i) a body member having a plurality of external surfaces and fabricated to contain a continuous fluid pathway therethrough, the pathway comprising a first port, a second port, and a binding channel intermediate and in fluid communication with the first port and the second port, wherein the binding channel is open to one of the external surfaces of the body member; and (ii) a glass member affixed to the one of the external surfaces of the body member to provide a first unmodified flat glass surface in fluid communication with the binding channel. The binding channel and glass member define a binding chamber effective for binding a heterogeneous population of nucleic acids, and the fluid pathway is essentially free of nucleic acid-specific binding sites. Within one embodiment, the fluid pathway further comprises a first channel connecting the first port with the binding chamber and a second channel connecting the second port with the binding chamber. Within another embodiment, the binding channel is open to a second of the external surfaces of the body member, and the device further comprises a second glass member affixed to the second external surface of the body member to provide a second unmodified flat glass surface in fluid communication with the binding channel. Within another embodiment, the first port or the second port comprises a Luer-lock fitting, an O-ring, a gasket, a tubing stub, or an elastomeric septum. Within a further embodiment, each of the first port and the second port comprises a Luer-lock fitting, an O-ring, a gasket, a tubing stub, or an elastomeric septum. Within a further embodiment, the binding chamber comprises a serpentine channel, such as a planar serpentine channel or a circumferentially flattened helical channel. In related embodiments, the binding chamber comprises two circumferentially flattened helical channels, which in certain embodiments are coaxial. The binding chamber may further comprise a viewing window. Within additional embodiments, the binding chamber is rectangular in cross-section. In other embodiments, the device also comprises a pump in fluid communication with one of the ports. In related embodiments, the device further comprises fluid distribution control means in fluid communication with the pump. Within certain related embodiments, the fluid distribution control means comprises a programmable computer. Within additional embodiments, the fluid pathway further comprises a distribution channel in fluid communication with the binding channel and a plurality of capillary channels in fluid communication with the distribution channel distal to the binding channel. Within a related embodiment, the device further comprises a plurality of assay wells, wherein each of the assay wells is in fluid communication with one of the capillary channels.

Within a second aspect of the invention there is provided a device comprising (i) a body member having a plurality of external surfaces and fabricated to contain a continuous fluid pathway therethrough, the pathway comprising a first port; a second port; a binding channel intermediate and in fluid communication with the first port and the second port, wherein the binding channel is open to one of the external surfaces of the body member; a distribution channel in fluid communication with the binding channel; and a plurality of capillary channels in fluid communication with the distribution channel distal to the binding channel; and (ii) a glass member affixed to the one of the external surfaces of the body member to provide a first unmodified flat glass surface in fluid communication with the binding channel. The binding channel and glass member define a binding chamber effective for binding a heterogeneous population of nucleic acids. Within one embodiment, the device further comprises a plurality of assay wells, wherein each of the assay wells is in fluid communication with one of the capillary channels.

Within a third aspect of the invention there is provided a device comprising (i) a body member having a plurality of external surfaces and fabricated to contain a single continuous fluid pathway therethrough, the pathway consisting essentially of a first channel; a second channel; a binding channel between the first channel and the second channel, wherein the binding channel is open to one of the external surfaces of the body member; and a plurality of ports, wherein at least one of the ports is in fluid communication with the first channel distal to the binding channel, and wherein at least another of the ports is in fluid communication with the second channel distal to the binding channel; and (ii) a glass member affixed to the one of the external surfaces of the body member to provide a first unmodified flat glass surface in fluid communication with the binding channel, wherein the binding channel and glass member define a binding chamber effective for binding a heterogeneous population of nucleic acids and wherein the fluid pathway is essentially free of nucleic acid-specific binding sites. Within one embodiment, the binding channel is open to a second of the external surfaces of the body member and the device further comprises a second glass member affixed to the second external surface of the body member to provide a second unmodified flat glass surface in fluid communication with the binding channel. Within another embodiment, the body member comprises a plurality of layered sheets of solid material selected from the group consisting of organic polymeric materials and glass. Within related embodiments, the solid material is selected from the group consisting of polyethylene terephthalate, cellulose acetate, acrylic, polycarbonate, polypropylene, and polyvinylchloride. Within other embodiments, at least one of the ports comprises a Luer-lock fitting, an O-ring, a gasket, a tubing stub, or an elastomeric septum. Within another embodiment, the binding channel is a serpentine channel. Within an additional embodiment, the serpentine channel is planar. Within other embodiments, the serpentine channel is a circumferentially flattened helix. Within related embodiments, the binding chamber comprises two circumferentially flattened helical channels, which channels are optionally coaxial. Within other embodiments, the binding chamber is rectangular in cross-section. Within further embodiments, the device also comprises a pump in fluid communication with one of the ports, and may further comprise fluid distribution control means in fluid communication with the pump. In a related embodiment, the fluid distribution control means comprises a programmable computer. In yet another embodiment, the device consists essentially of (i) a body member having a plurality of external surfaces and fabricated to contain a single continuous fluid pathway therethrough, the pathway consisting essentially of a first channel; a second channel; a binding channel between the first channel and the second channel, wherein the binding channel is open to first and second external surfaces of the body member; and a plurality of ports, wherein at least one of the ports is in fluid communication with the first channel distal to the binding channel, and wherein at least another of the ports is in fluid communication with the second channel distal to the binding channel; (ii) a first glass member affixed to the first external surface of the body member to provide a first unmodified flat glass surface in fluid communication with the binding channel; and (iii) a second glass member affixed to the second external surface of the body member to provide a second unmodified flat glass surface in fluid communication with the binding channel, wherein the binding channel, the first glass member, and the second glass member define a binding chamber effective for binding a heterogeneous population of nucleic acids and wherein the fluid pathway is essentially free of nucleic acid-specific binding sites.

Within a fourth aspect of the invention there is provided a process for extracting nucleic acid from a biological sample. The process comprises the steps of (a) introducing a nucleic acid-containing sample into the binding chamber of a device as disclosed above via one of the ports, (b) allowing nucleic acid in the sample to bind to the unmodified flat glass surface, (c) washing the binding chamber to remove contaminants, and (d) eluting bound nucleic acid from the unmodified flat glass surface. Within certain embodiments the process comprises the additional step of lysing a cell sample to prepare the nucleic acid-containing sample. Within another embodiment, the nucleic acid-containing sample contains human nucleic acid. Within a further embodiment, the nucleic acid-containing sample contains non-human nucleic acid. Within an additional embodiment, the nucleic acid is DNA. Within a related embodiment, the nucleic acid is genomic DNA. Within an additional embodiment, the bound nucleic acid is eluted with a buffer containing a fluorescent compound that exhibits a change in fluorescence intensity in the presence of nucleic acids. Within a further embodiment, flow of liquid through the binding chamber is laminar. Within an additional embodiment, the process comprises the additional step of amplifying the eluted nucleic acid. Within a related embodiment the amplifying step comprises isothermal amplification.

Within a fifth aspect of the invention there is provided a kit comprising a device as disclosed above and a buffer in a sealed container. The buffer may be a lysis buffer, a wash buffer, or an elution buffer. Within one embodiment, the buffer is an elution buffer. Within a related embodiment, the buffer is an elution buffer that comprises a fluorescent compound that exhibits a change in fluorescence intensity in the presence of nucleic acids, such as a bis-benzimide compound. Within another embodiment, the kit further comprises a second buffer in a second sealed container, wherein the buffer is a lysis buffer or a wash buffer. Within a further embodiment, the kit further comprises an instruction document.

These and other aspects of the invention will become evident upon reference to the following detailed description of the invention and the attached drawings.

All references cited herein are incorporated by reference in their entirety. Numeric ranges recited herein include the endpoints.

DESCRIPTION OF THE INVENTION

Figure 1A:
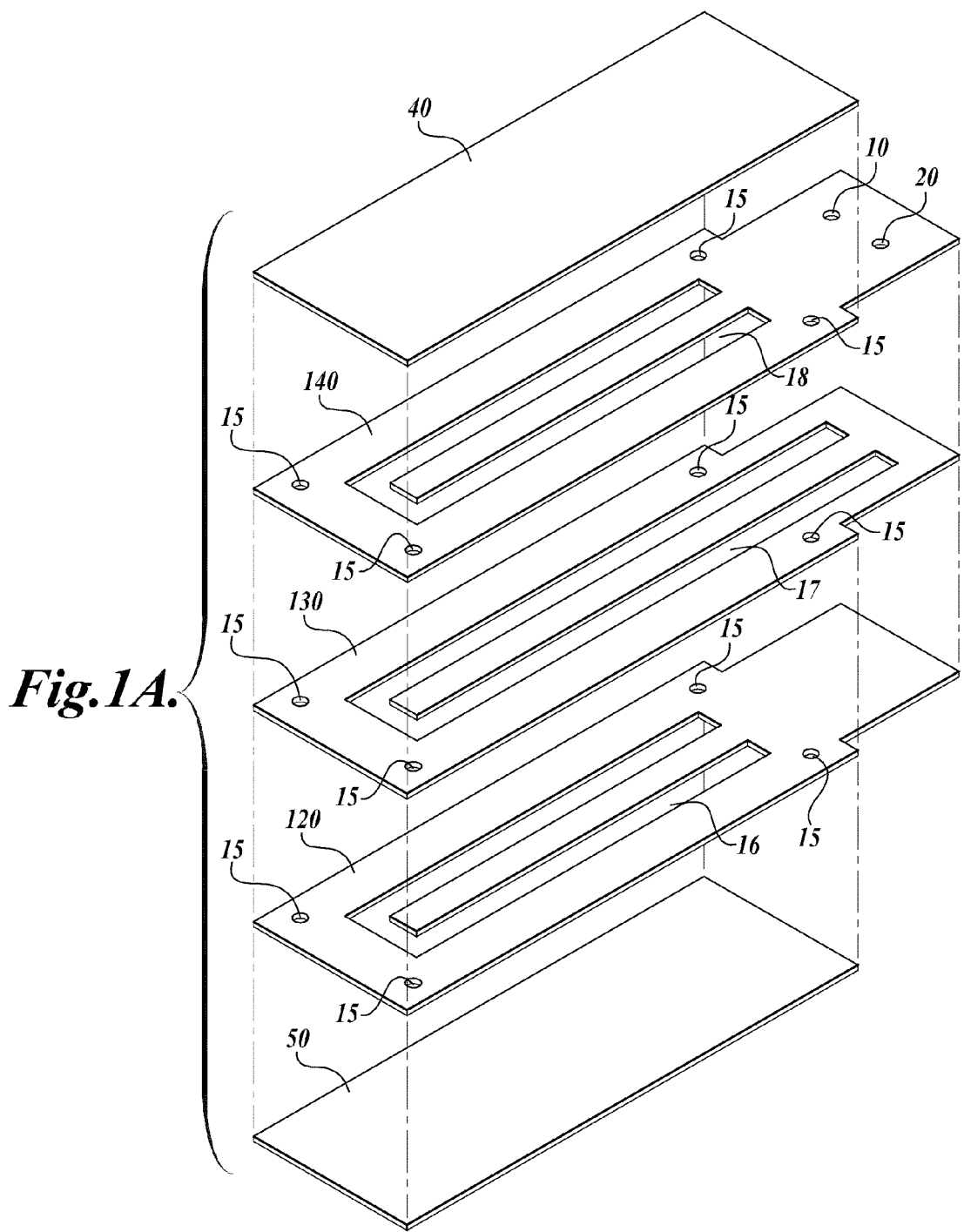
FIGS. 1A and 1B illustrate the assembly of a multi-layer device of the invention.

The present invention provides for the extraction of nucleic acids, including deoxyribonucleic acids (DNA) and ribonucleic acids (RNA), from biological samples. As used herein, the term "biological sample" means a sample containing cells or cell components and includes any sample, liquid or solid, that contains nucleic acids. Suitable biological samples that can be used within the invention include, without limitation, cell cultures, culture broths, cell suspensions, tissue samples, cell lysates, whole blood, serum, buffy coat, urine, feces, cerebrospinal fluid, semen, saliva, wound exudate, viruses, mitochondria, and chloroplasts. In one embodiment, the sample is blood or a blood product (e.g., platelets) and the nucleic acids that are extracted are those from contaminant bacterial pathogens in the blood or blood product. Thus, the present invention provides for the extraction of nucleic acids in soluble form from complex mixtures.

DNA produced through the present invention has been found to be of high quality for downstream applications. In comparison to porous glass surfaces, the flat glass surfaces used in the invention are easy to wash free of enzymes, metals (heme), and other protein contaminants that can interfere with PCR-based assays. The flat glass-based method works with dilute samples such a platelet-rich plasma to give improved yield and quality of DNA as compared to porous-bead "spin columns." PCR yields were improved and variability decreased. The devices of the invention also allow the extracted nucleic acids to be concentrated. For example, DNA captured in a 0.5-mL binding chamber can be concentrated in 0.1 mL of elution buffer by sweeping the buffer through the chamber. The invention therefore provides advantages over previously known extraction systems when working with samples that are dilute with respect to nucleic acid content (e.g., platelet concentrates, plasma, serum, urine, environmental samples, or forensic samples), or for pathogen detection with improved sensitivity.

The devices of the present invention are designed for ease of use and construction. Within certain embodiments, movement of fluids through the devices does not require internal valving. However, the design of the devices allows the addition of further channels, wells, and valves to allow more extensive manipulation and analysis to be carried out within the device. In addition, the devices are designed to be resistant to contamination, in contrast to standard spin columns. The flow-through design is flexible with regard to sample and reagent volumes, allowing dilute nucleic acid samples to be concentrated in the extraction process, and further allows quick drying of the internal channels using filtered air circulation. The glass walls of the binding chamber permit quantification of nucleic acids within the device, such as through the use of a fluorimeter. Multiple washing and drying steps can be automated, eliminating the need for manual manipulation of the device after sample loading and allowing more controlled timing of steps.

Figure 1B:
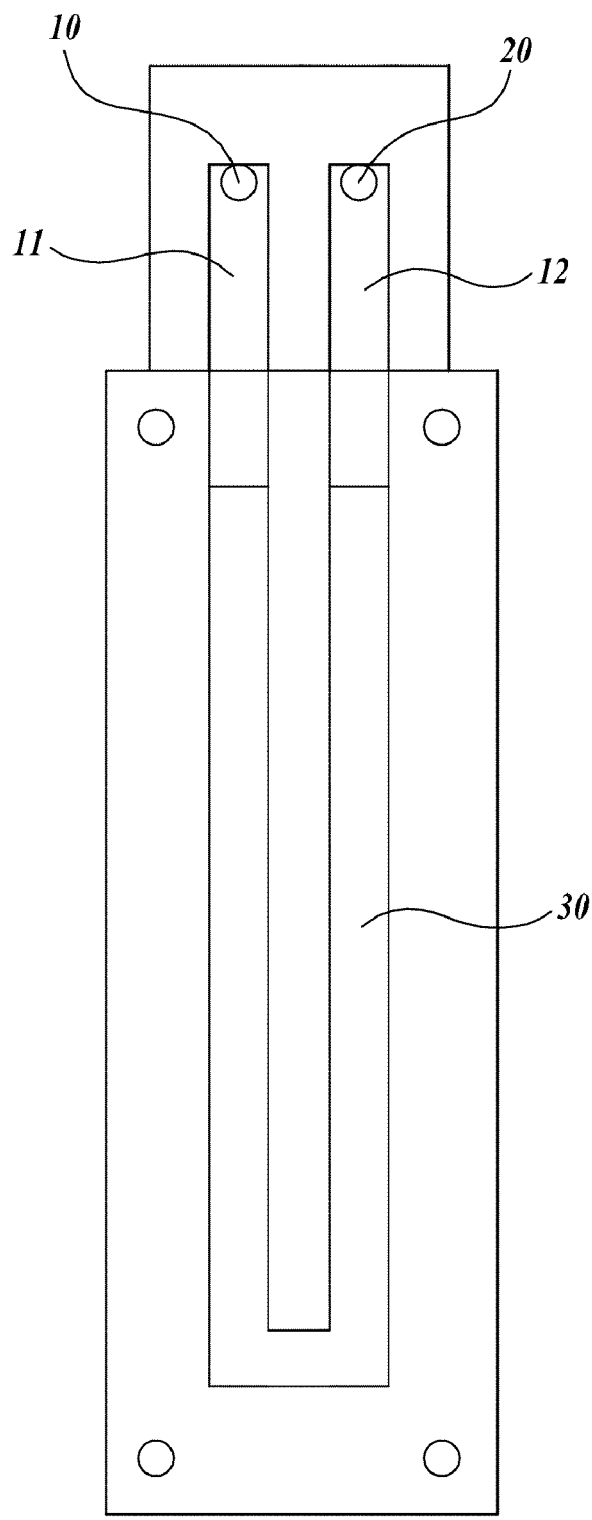

Devices of the present invention comprise a plurality of ports and a binding chamber intermediate and in fluid communication with at least two of said plurality of ports. These ports provide for the introduction of a nucleic acid-containing sample into the binding chamber, for the introduction of reagents, and for the removal of waste products and extracted nucleic acid. For example, a first port can be used for introducing fluids into the binding chamber and a second port used for removing fluids from the binding chamber, although alternative operations are within the scope of the invention. For convenience, ports are designated herein by ordinal numbers (e.g., "first port," "second port," etc.). These designations are not intended to limit the use of any particular port. One such device is illustrated in FIGS. 1A and 1B and comprises a body fabricated from a plurality of layers, including outer glass layers 40 and 50, and internal plastic layers 120, 130, and 140. As shown in FIG. 1B, a continuous fluid pathway passes through the body, providing a first channel 11, a binding chamber 30, and a second channel 12. First port 10 and second port 20 provide access to the first channel and second channel, respectively. As shown in FIG. 1A, a plurality of alignment holes 15 are provided to facilitate assembly of the layers. Internal layers 120, 130, and 140 are cut to provide the desired shape and the various openings. Thus, the illustrated U-shaped openings 16, 17, and 18 create, upon assembly, binding chamber 30 in fluid communication with first channel 11, first port 10, second channel 12, and second port 20. Adhesive layers used to bond the glass and plastic layers are not shown.

The binding chamber is configured to optimize device performance, including nucleic acid extraction efficiency and quality. In addition, the device is designed to enable a bolus of liquid to move through the device without an air bubble penetrating the leading edge and becoming entrained in the bolus. Parameters to be considered in optimizing performance include: (1) the ratio of total volume to exposed flat glass surface area; (2) the ratio of non-glass surface area to glass surface area; (3) the number of layers used to create the binding chamber (the more layers, the more irregular the chamber walls will be); and (4) the amount and type of adhesive exposed to the fluids.

The binding chamber is formed by the combination of a binding channel disposed within the body of the device and at least one glass member. The binding channel is open to at least one external surface of the body, and the glass member is affixed to that external surface, thereby providing an unmodified flat glass surface in fluid communication with the binding channel. Within some embodiments, the binding channel is open to two external surfaces of the body, and a second glass member is affixed to the second of the external surfaces, thereby providing a binding chamber with two glass surfaces.

In certain embodiments of the invention the binding chamber is rectangular in cross-section. Those skilled in the art will recognize that, in view of the fabrication methods involved, the walls of the binding chamber may exhibit irregularities in shape. Such irregularities may arise, for example, as artifacts of the cutting process (e.g., tolerance variations) or from slight mis-alignment of bonded layers. It is generally desirable to minimize such irregularities to the extent practicable.

In one embodiment, the shape and proportions of the binding chamber are selected to provide for laminar flow of liquids passing therethrough. Whether flow is turbulent or laminar can be characterized by its Reynolds number (Re). The Reynolds number can be described as the ratio of inertial forces over viscous forces, where viscous forces can be thought of as a resistance to velocity and inertial forces can be thought of as a resistance to change in velocity.

$Re = (p \times Vs \times L)/(u)$, where:

p=fluid density (kg/m$^3$)
Vs=mean fluid velocity (m/s)

L=characteristic length (m), which for pipes is Dh=hydraulic diameter (m)

Dh=(4×Area)/(perimeter), i.e., area and perimeter of pipe cross section.

u=absolute viscosity (s N/m²)

When Re is below 2300 the flow is considered laminar, and when Re is above 4000 the flow is considered turbulent. Anything between the two is considered a transition region and preferably avoided to improve predictability. Within the present invention it preferred that Re be less than 1000, more preferably less than 100.

Within the present invention, fluid channel (including first channel, second channel, and binding chamber) cross-section dimensions are ordinarily within the range of 0.15 mm×1 mm to 0.5 mm×6 mm, or circular channels having diameters providing similar volumes. Flow rates will generally not exceed 600 µL/second, and will typically be approximately 60 µL/second. Using the above equation and the values:

L=0.00026 m (small channel) or 0.0009 m (large channel)
Vs=0.4 m/s (small channel) to 0.02 m/s (large channel)
p(water)=1000 kg/m³
u(water)=1/1000 sN/m²

Re=1000×0.4×0.00026×1000=104, at a flow rate 60 µL/second in a small channel; and Re=1000×0.02×0.0009×1000=18, at a flow rate of 60 µL/second in a large channel. At a flow rate of 600 µL/second, Re=1040 in the small channel and Re=180 in the large channel. Thus, devices having the above-disclosed dimensions can accommodate flow rates in excess of 1300 µL/second before Re approaches the transition region.

Within one embodiment of the invention, the binding chamber is serpentine in shape. As used herein, "serpentine" chambers include planar chambers that bend in two dimensions as well as three-dimensional pathways having the form of a helix and variants thereof. Such three-dimensional structures will ordinarily be circumferentially flattened along at least one side to provide extended binding area in contact with the glass surface. Typically, the helix will be circumferentially flattened along two opposite sides and the binding chamber will comprise glass surfaces on both flattened sides. A serpentine shape allows for exposure of the sample to a large surface area of glass, while keeping the cross-section dimensions of the binding chamber small. Limiting the cross-section dimensions contributes to the prevention of air bubbles slipping past the leading edge of a liquid bolus within the chamber. The serpentine design also allows this combination of high surface area (glass-liquid interface) and small cross-section to exist within a compact footprint.

Figure 2A:
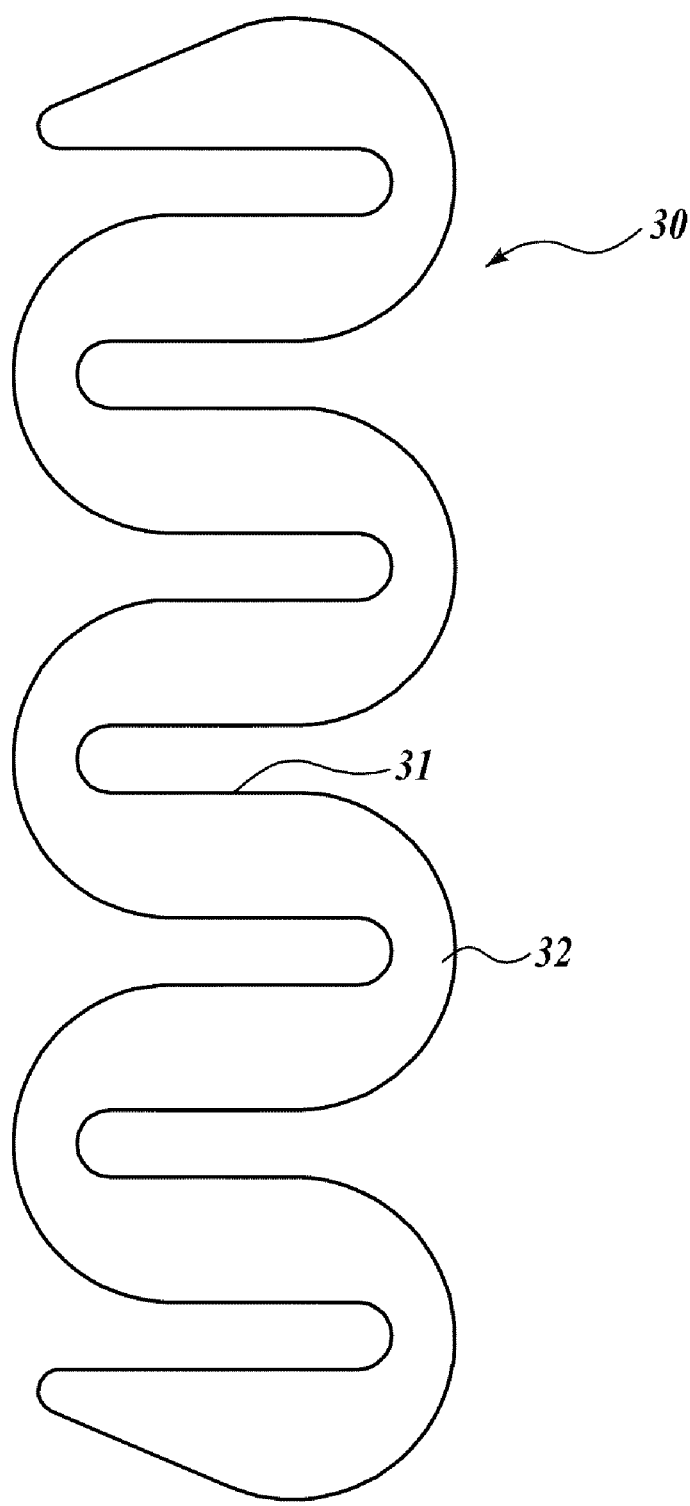
FIGS. 2A and 2B illustrate alternative embodiments of the binding chamber of the device of the invention.
Figure 2B:
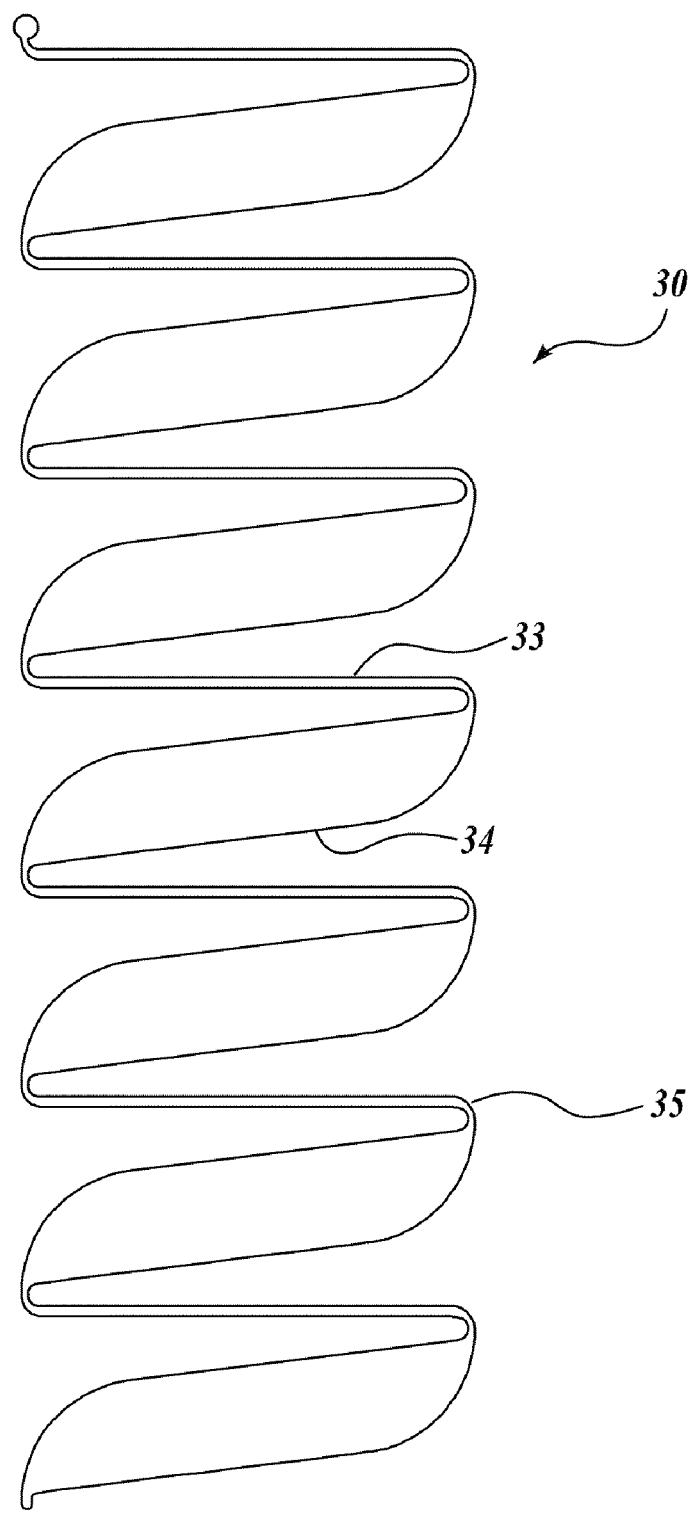

FIGS. 2A and 2B illustrate two embodiments of binding chamber 30. Within these embodiments the chamber comprises a serpentine channel in a planar configuration. The chamber shown in FIG. 2A, termed an "S-channel," comprises a series of linear segments 31 of equal dimension connected by 180° bends 32 having a narrower cross-section. The binding chamber of FIG. 2B, termed a "W-channel," comprises alternating narrow 33 and wide 34 linear segments connected by bends 35 of approximately 90°. The W-channel provides a relatively smaller chamber volume and a varied cross-section, which has been found to reduce the likelihood of air bubbles passing the leading edge of the liquid bolus in certain orientations of the device. In particular, devices comprising a W-channel can be operated in a vertical orientation and utilize gravity to drive fluid flow. Thus, the W-channel design facilitates manual operation of the device. In contrast, the S-channel device can be operated with binding chamber 30 in a horizontal orientation wherein fluid flow is driven by external pressure, such as from a pump. The S-channel design thus facilitates automated operation.

It is preferred to configure the binding chamber so that its contents can be "read" using a standard 96-well plate reader. Thus, the size and shape of the binding chamber are preferably selected so that it overlays at least a portion of a 96-well plate with portions of the chamber overlying wells of the plate. If the device is undersized relative to a 96-well plate, the device can be fitted to an adapter or carrier that shares the footprint with a 96-well plate and aligns the device such that the binding chamber or other target area is in an appropriate location.

The devices of the present invention comprise, within the binding chamber, an unmodified flat glass surface effective for binding a heterogeneous population of nucleic acids. As used herein, and "unmodified flat glass surface" means a glass surface having a flatness corresponding to that of a standard microscope slide, wherein the surface has not been etched or otherwise altered to increase its surface area, and wherein it has not been modified to specifically bind nucleic acids as disclosed below. Suitable glass materials in this regard include flat soda lime glass (e.g., Erie Electroverre Glass; Erie Scientific Company, Portsmouth, N.H.) borosilicate glass (e.g., Corning 0211; Corning Incorporated, Corning, N.Y.). Of particular interest for use within the present invention is soda lime glass available in standard slide (25×75 mm or 50×75 mm) and cover slip (20 mm or 25 mm squares) forms. Slides and cover slips are available from commercial suppliers. Standard microscope slides can be readily incorporated into the device. Slides are available in a variety of thicknesses, from approximately 0.6 mm to 5.0 mm or more. Slides that are approximately 1 mm thick are conveniently employed. The binding chamber is essentially free of nucleic acid-specific binding sites, such as charged surfaces or binding sites provided by immobilized oligonucleotides, minor groove binding agents, intercalating agents, or the like. A binding chamber that is "essentially free of nucleic acid-specific binding sites" is one that does not contain an amount of such sites sufficient to give a statistically significant increase in nucleic acid binding as compared to glass.

The remainder of the body of the device is preferably made from materials that exhibit low auto-fluorescence and very low binding of nucleic acids. The materials should also be impervious to ethanol. Rigid or semi-rigid, organic polymeric materials are preferred. Representative such materials include acrylic (a high molecular weight rigid material), polycarbonate, polypropylene, cellulose acetate, polyethylene terephthalate (PET), and polyvinylchloride, but not polystyrene. Other materials, including poly(dimethylsiloxane) and silicone rubber, can also be employed. These layers are cut using methods known in the art, including die-cutting, photolithography, soft lithography, micromachining, laser ablation, and plasma etching. See, Fiorini and Chu, *BioTechniques* 38:429-446, 2005. In the alternative, individual layers can be molded. These layers may be bonded together using adhesives, such as pressure-sensitive or thermally-activated adhesives. Suitable adhesive materials for bonding layers include, without limitation, acrylic adhesive films (e.g, 300LSE adhesive film, 467 acrylic adhesive film, and 8141 acrylic adhesive film; 3M Company, St. Paul, Minn.) and silicone adhesives (e.g., TRANSIL silicone adhesive film). As disclosed in more detail below, outgassing of certain adhesives after device manufacture may reduce DNA yield; vacuum degassing of the device prior to use can be used to alleviate this issue.

As disclosed above, the device further comprises a plurality of ports through which liquids can be introduced into or removed from the binding chamber. Thus, the ports provide openings through the surface of the device and are in fluid communication with the binding chamber, which is positioned between at least two of the ports. In the simplest configuration, first and second ports are provided as openings in a flat surface of the device. Such openings are conveniently circular in shape, although shape is a matter of routine design choice. The ports can further comprise additional components, allowing the sample and various wash buffers to be introduced into the device by various means. For example, Peek tubing stubs can be attached to the device to allow manual input. Manual addition allows the various buffers to be optimized for volume, incubation time, and flow rate. In the alternative, standard 1-mL polypropylene syringes or a programmable peristaltic pump can be used with tubing and Luer-lock adaptors. Within another embodiment, the ports are provided by small diameter holes sized to accept a needle (e.g., a blunt tip, 22G needle) inserted into the hole. Connections to the needles are made using Luer-lock fittings. In another embodiment, one or more of the ports comprises an elastomeric septum that can be pierced with a needle or cannula, thus providing a device that is sealed until the time of use. In an alternative embodiment, the device is provided with flat ports on its surface. This arrangement permits a connection manifold to be clamped over the ports. The connections can be further sealed against leaks by the inclusion of O-rings, gaskets, or the like in the ports. In another embodiment, the device comprises separate ports for sample input and reagent input. The sample input port can be fitted with a Luer-lock fitting, an elastomeric septum, or a fitting adapted to receive a pipette tip. This arrangement allows the sample to be introduced without contaminating the port used for reagent input. Ports lacking sealable openings can be sealed with adhesive tape when desired.

First and second ports can be positioned on the upper surface of the device, facilitating the simultaneous operation of a plurality of devices. Such devices can be aligned in a rack, and a multi-slot manifold equipped with a single cammed lever can be attached to the devices, sealing against each device in the system simultaneously. To automate the system, this arrangement can then be connected to a valve mechanism connected to a microprocessor-controlled, multi-channel peristaltic pump as disclosed in more detail below.

Within some embodiments of the invention, first and second channels connect the binding chamber to the first and second ports, respectively. As with the ports, channels are designated herein for convenience by ordinal numbers, which numbers are not intended to denote the use or purpose of any particular channel. These channels are typically of small diameter so as to prevent air bubbles from entering the liquid bolus under normal operating conditions of pressure and flow rate. In some embodiments, the fluid pathway within the device consists essentially of first and second channels in direct fluid communication with the binding chamber and a plurality of ports. In this configuration, the fluid pathway does not include other functional elements such as viewing windows, additional channels, or valves.

Together, the ports, binding channel, and (if present) first and second channels provide a continuous fluid pathway through the body of the device. A "continuous fluid pathway" is a pathway that allows fluid to travel continuously through the device from the first port, through the binding channel, to the second port. Additional ports and/or channels may be connected to the pathway. A "single continuous fluid pathway" denotes a continuous fluid pathway that is unbranched. Within certain embodiments of the invention the fluid pathway is essentially free of nucleic acid-specific binding sites.

Figure 3A:
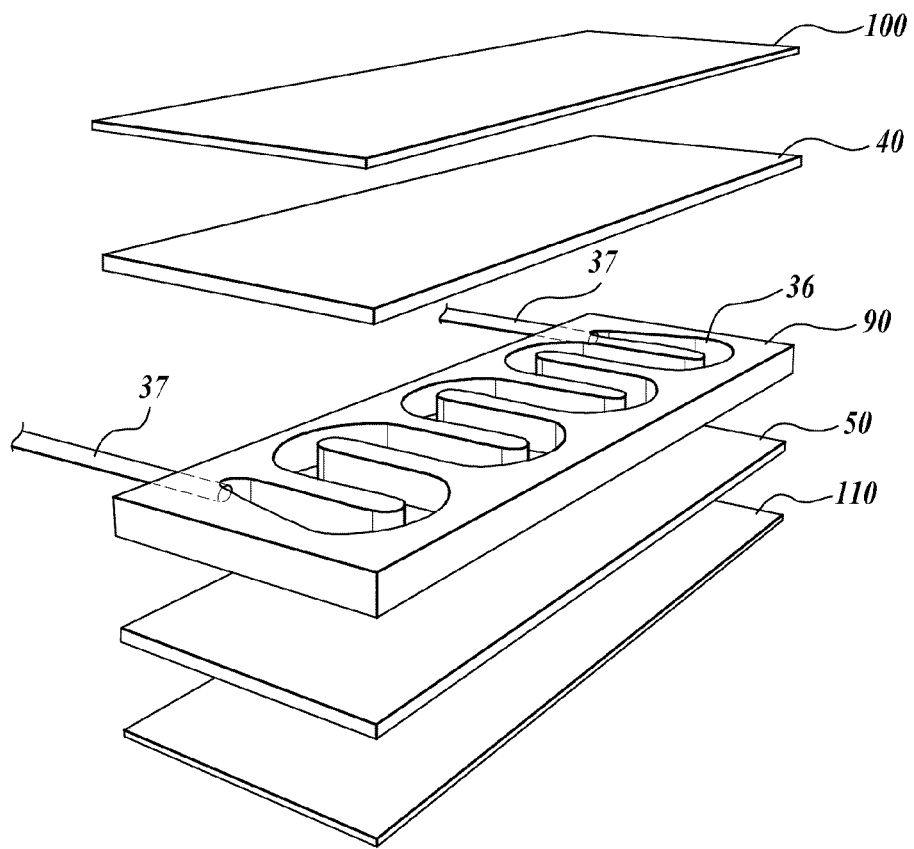
FIGS. 3A and 3B illustrate the assembly of a device of the invention.
Figure 3B:
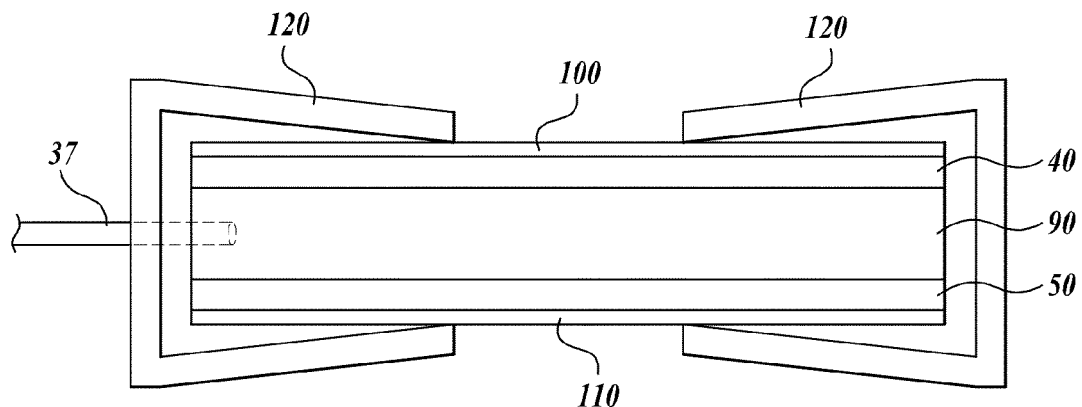

FIGS. 3A and 3B illustrate a device constructed using a compression seal. Compression sealed construction utilizes a single, die-cut body member 90 of compliant material. Suitable materials include silicone rubber, Neoprene, urethane, natural rubber, Buna-N, and the like. Serpentine binding channel 36 is cut entirely through body member 90, making it open to the upper and lower surfaces of the body member. First and second glass members (e.g., slides) 40 and 50 are clamped in place on each side of silicone rubber body member 90, creating a sealed binding chamber. In the illustrated embodiment, the device further comprises outer layers of rigid or semi-rigid plastic 100 and 110. Clamping is conveniently achieved through the use of U-shaped channels 120 of sufficient rigidity to provide a leak-proof assembly. Conventional plastic U-channel stock cut to length can be used for this purpose. First and second ports (not shown) are then constructed, such as by boring through the rubber layer. In one embodiment, holes are bored in the rubber and blunt-tip needles 37 are inserted into the holes to provide first and second ports. In another embodiment, tubing is inserted into bored holes. In an alternative embodiment, sharp needles, cannulas, or the like are inserted through the edge of the rubber layer and into the binding chamber to form the ports.

Figure 4A:
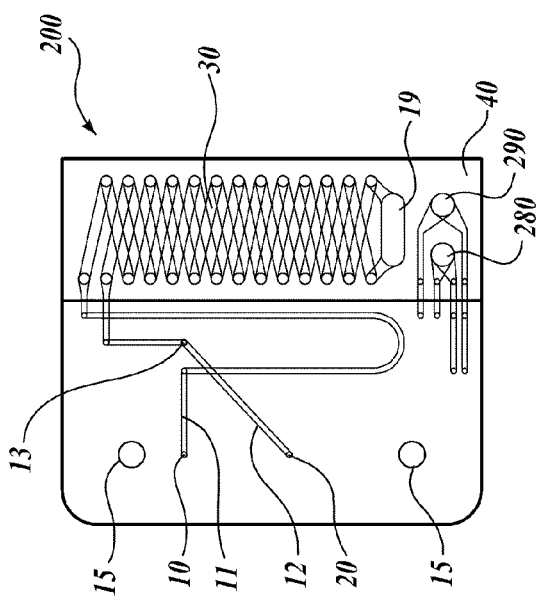
FIGS. 4A and 4B illustrate a device having a circumferentially flattened, helical binding chamber.
Figure 4B:
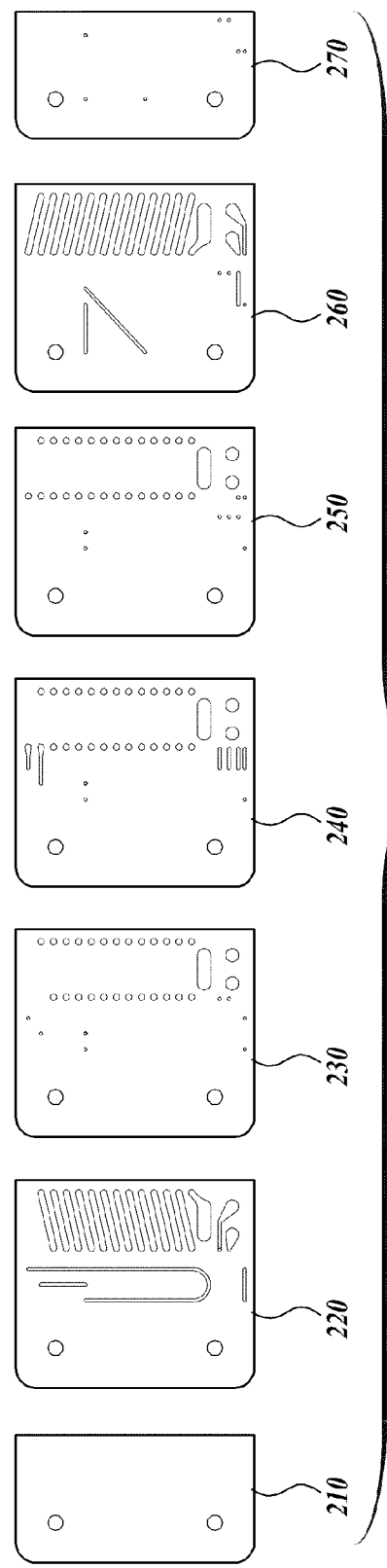

FIGS. 4A and 4B illustrate a further embodiment of the device of the invention, referred to as an "X-channel" device. Device 200 comprises first port 10, second port 20, first channel 11, second channel 12, and binding chamber 30. Binding chamber 30 comprises two circumferentially flattened helical channels, and further comprises viewing window 19 between the two circumferentially flattened helical channels. The viewing window is an open channel through all internal layers of the device, allowing optical readings to be taken without interference of plastic layers. It is preferred that viewing window 19 be configured to span a region corresponding to 2 holes of a standard 96-well assay plate, thereby facilitating the analysis of nucleic acid extraction using conventional plate reading equipment. In addition, device 200 comprises a third port 13 adapted to receive a pipette tip. A sample may be introduced into the device through third port 13 without risking contamination of first port 10 and first channel 11. This design thus provides the option of introducing the sample into the binding chamber via either the first channel or the second channel. Other fluids, including wash buffers and elution buffer, are introduced through first port 10 and first channel 11, and waste products are removed via second channel 12 and second port 20. Alignment holes 15 facilitate proper registration of the component layers during assembly. The illustrated device further comprises a pair of calibration wells 280 and 290 into which may be introduced reference standards for calibration of fluorescence detection equipment. Wells 280 and 290 comprise channels through which liquids may be introduced and removed. These wells may be positioned to correspond to holes in a standard 96-well plate. FIG. 4B illustrates component layers 210, 220, 230, 240, 250, 260, and 270 that, upon assembly, combine to provide the various channels and ports. Openings are cut in the layers using conventional methods. Following assembly of the plastic components, glass members 40 are added to front and back surfaces of the assembled body adjacent layers 210 and 270 and on top of layers 220 and 260 to define binding chamber 30. The layers are assembled using adhesive layers (not shown) as disclosed above. The adhesive seals well and the device does not leak under moderate operating pressure.

A more detailed description of a representative X-channel device and its features is as follows:

⅛ inch thick, clear walled, laminated construction.

First and second channel widths=1.0 mm.

Port diameter for first and second ports=1.0 mm.

Port diameter for pipette port (third port)=1.0-2.0 mm, sized to fit desired pipette tip.

X-channel fits within the area of a standard glass slide, width=25.3 mm, length=75.5 mm.

Glass slide separation distance (binding chamber thickness)=38 mils (965.2 µm).

X-channel volume (binding chamber volume)=488 µl; area of exposed glass surface is 1266 mm$^2$.

Exterior dimensions of the device without added fittings are approximately 66.3 mm by 76.0 mm by 2.97 mm (thickness).

As discussed above, the device can be constructed to fit a standard 96-well plate reader, either alone or in combination with a carrier plate. Such a carrier will position the device to align chosen areas (e.g., binding chamber, viewing window, calibration wells) to the standard well locations. The illustrated device has glass walls formed by two glass microscope slides. Fluorescence can be measured in the X-channel or in the viewing window.

The design of the device shown in FIGS. 4A and 4B provides advantages over devices with planar serpentine binding chambers, such as that shown in FIGS. 1A and 1B. This design better excludes bubbles from the fluid bolus in multiple orientations of the device, while maintaining a high glass contact area in the binding chamber. When the device is fabricated with a binding chamber width of 2 mm, a helix pitch of 2 mm, and a standard microscope slide as the glass member, the glass surface exposed to fluid flow is approximately 712 mm$^2$ on each side of the device, for a total exposed glass surface of 1424 mm$^2$.

Figure 5:
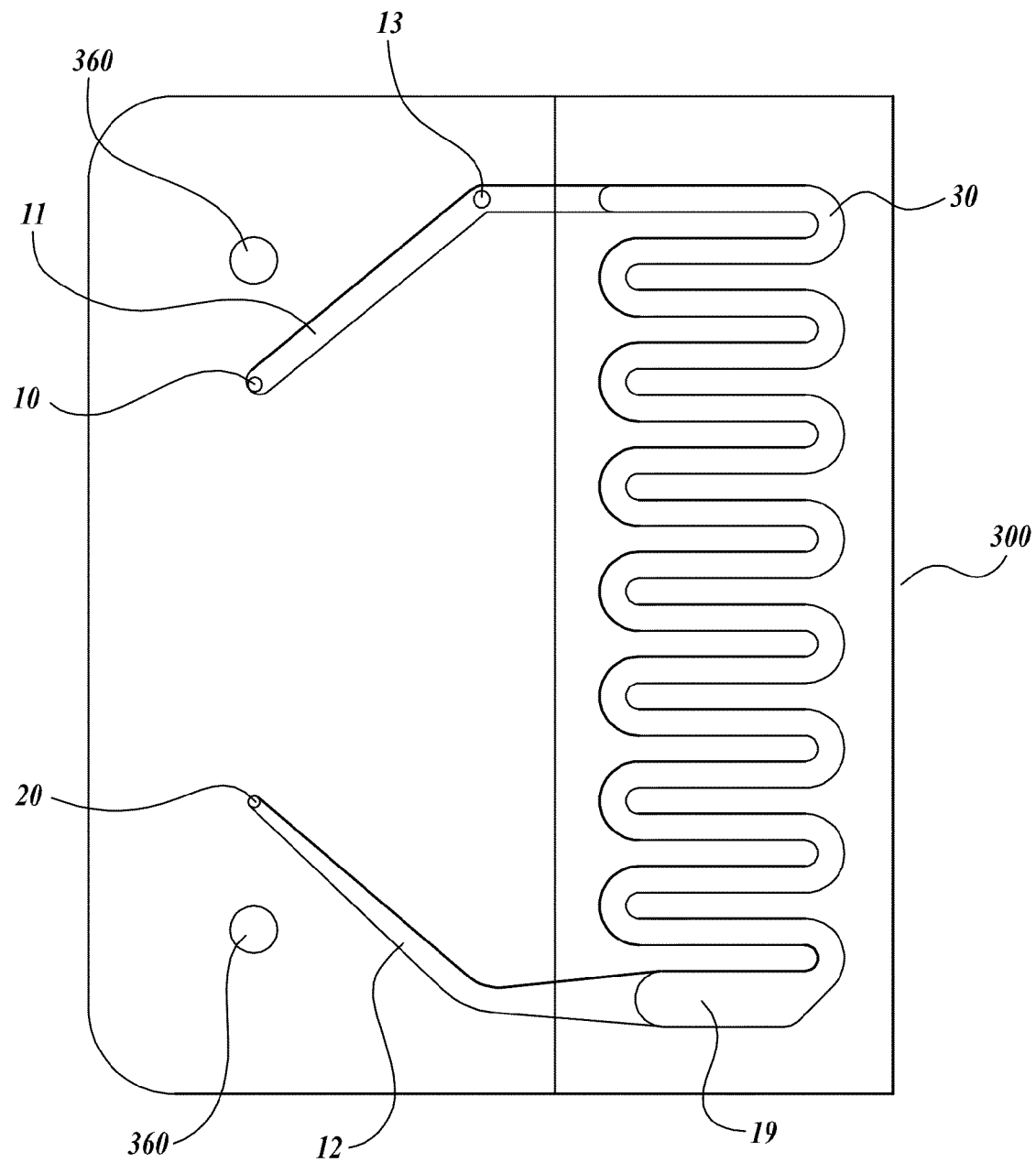
FIG. 5 illustrates a device of the invention comprising a planar serpentine binding chamber.

FIG. 5 illustrates an alternative embodiment of the device of the invention. The design of device 300 facilitates its use with a manifold that can connect to a plurality of such devices. Such an arrangement allows for the simultaneous extraction of nucleic acid from multiple samples. Device 300 comprises S-shaped binding chamber 30, the dimensions of which are held essentially constant throughout most of its length. The terminal segment of binding chamber 30 is expanded to provide viewing window 19. In an exemplary embodiment, viewing window 19 has a volume of 50 µL. This device further comprises first channel 11 and second channel 12, through which fluids are introduced into and removed from the device. Within this embodiment, inlet and outlet channels are not dedicated. Thus, a sample can be introduced through third port 13, such as by use of a micropipette, syringe, or the like. The device is then connected to a manifold (not shown), and wash reagents are introduced through second port 20 and second channel 12, and are removed through first port 10 and first channel 11. This arrangement ensures that the wash reagents are introduced through a clean channel, avoiding potential contamination from third port 13. Holes 360 serve to register the device to the manifold. Within one embodiment of device 300, third port 13 is fitted with an elastomeric septum (not shown) that seals around the pipette tip or other instrument used to introduce the sample, and further seals the port after the instrument is removed.

Figure 8A:
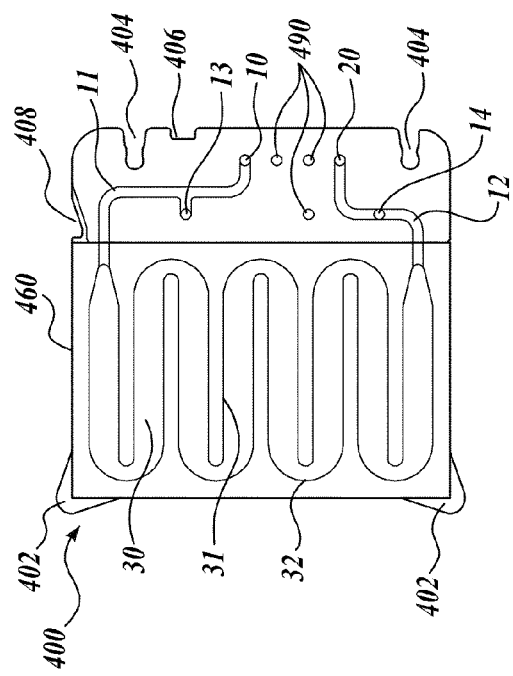
FIGS. 8A and 8B illustrate a device of the invention comprising a serpentine binding chamber with extended linear segments.
Figure 8B:
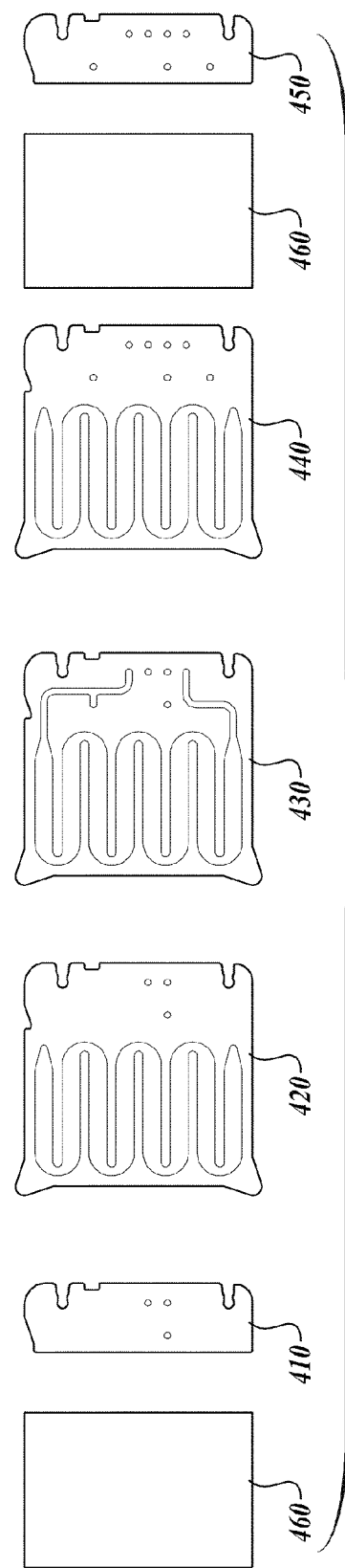

An additional device of the present invention is illustrated in FIGS. 8A and 8B. Device 400 (referred to as "version 4" or "v4") comprises a larger glass surface area for nucleic acid binding and is also adapted for use with a manifold that can connect to a plurality of such devices. As in device 300, first and second channels in device 400 are not dedicated. Device 400 comprises S-shaped binding chamber 30, in which linear segments 31 are wider than bends 32. This device further comprises first and second channels 11 and 12, through which fluids are introduced into and removed from the device. First channel 11 is accessed via first port 10 and third port 13. Second channel 12 is accessed via second port 20 and fourth port 14. A plurality of additional channels 490 pass through the device, which channels may be joined to additional device elements (not shown) as disclosed in further detail below. Additional features of device 400 include tabs 402, which protect the corners of the glass slides 460; slots 404, which can mate with guide pins in an external manifold (not shown); first notch 406, which identifies the device type and can be "read" by an instrument or manifold to which the device is connected; and second notch 408, which can be can be used to align an optical detector.

Within one embodiment, third port 13 of device 400 comprises a pipette interface for manual sample input through first channel 11. In this embodiment, second channel 12 is used for reagent input through second port 20 and product withdrawal through fourth port 14. Waste products (e.g., washes) are removed from the device through first channel 11 and first port 10. This arrangement eliminates the risk of contaminating subsequent inputs or the final product when introducing the initial sample, since the pipette or other input device is connected to what becomes the outlet of the device.

Device 400 is constructed by laminating a plurality of individual elements as shown in FIG. 8B. Table 1 provides detailed descriptions of elements 410, 420, 430, 440, 450, and 460. The external layers are formed by the combination of 2"×3" glass slides 460 with element 410 or 450. As disclosed in Table 1, individual elements are joined using silicone adhesive (not shown). Material thicknesses and the number of layers are exemplary and can be varied to obtain different device thicknesses and volumes. Specific materials are for illustrative purposes only and are not intended to be limiting; those skilled in the art will recognize that other materials can be substituted.

TABLE 1

| Layer | Element | Description | Material | Thickness | Manufacturer | Manufacturer's Part No. |
|---|---|---|---|---|---|---|
| 1a | 410 | Die Cut Laminate | Polyethylene Terephthalate (MYLAR) | 10 mil | Mellinex | — |
| 1b | 460 | 2" × 3" Microscope Slide | Soda Lime Glass | 1 mm | Erie Scientific | 2957F |
| 2 | N/A | Die Cut Adhesive | Silicone Adhesive | 2 mil | Avery Dennison | FT 3002 |

TABLE 1-continued

| Layer | Element | Description | Material | Thickness | Manufacturer | Manufacturer's Part No. |
|---|---|---|---|---|---|---|
| 3 | 420 | Die Cut Laminate | Polyethylene Terephthalate (MYLAR) | 5 mil | Mellinex | — |
| 4 | N/A | Die Cut Adhesive | Silicone Adhesive | 2 mil | Avery Dennison | FT 3002 |
| 5 | 430 | Die Cut Laminate | Polyethylene Terephthalate (MYLAR) | 10 mil | Mellinex | — |
| 6 | N/A | Die Cut Adhesive | Silicone Adhesive | 2 mil | Avery Dennison | FT 3002 |
| 7 | 440 | Die Cut Laminate | Polyethylene Terephthalate (MYLAR) | 5 mil | Mellinex | — |
| 8 | N/A | Die Cut Adhesive | Silicone Adhesive | 2 mil | Avery Dennison | FT 3002 |
| 9a | 450 | Die Cut Laminate | Polyethylene Terephthalate (MYLAR) | 10 mil | Mellinex | — |
| 9b | 460 | 2" × 3" Microscope Slide | Soda Lime Glass | 1 mm | Erie Scientific | 2957F |

The 2"×3" glass slides 460 used in device 400 provide a larger exposed glass surface area in binding chamber 30. In a representative device, linear segments 31 are 6 mm wide, and bends 32 are approximately 3 mm wide. Binding chamber 30 spans approximately 44.5 mm of the total 51.4 mm width of glass slides 460.

Figure 9:
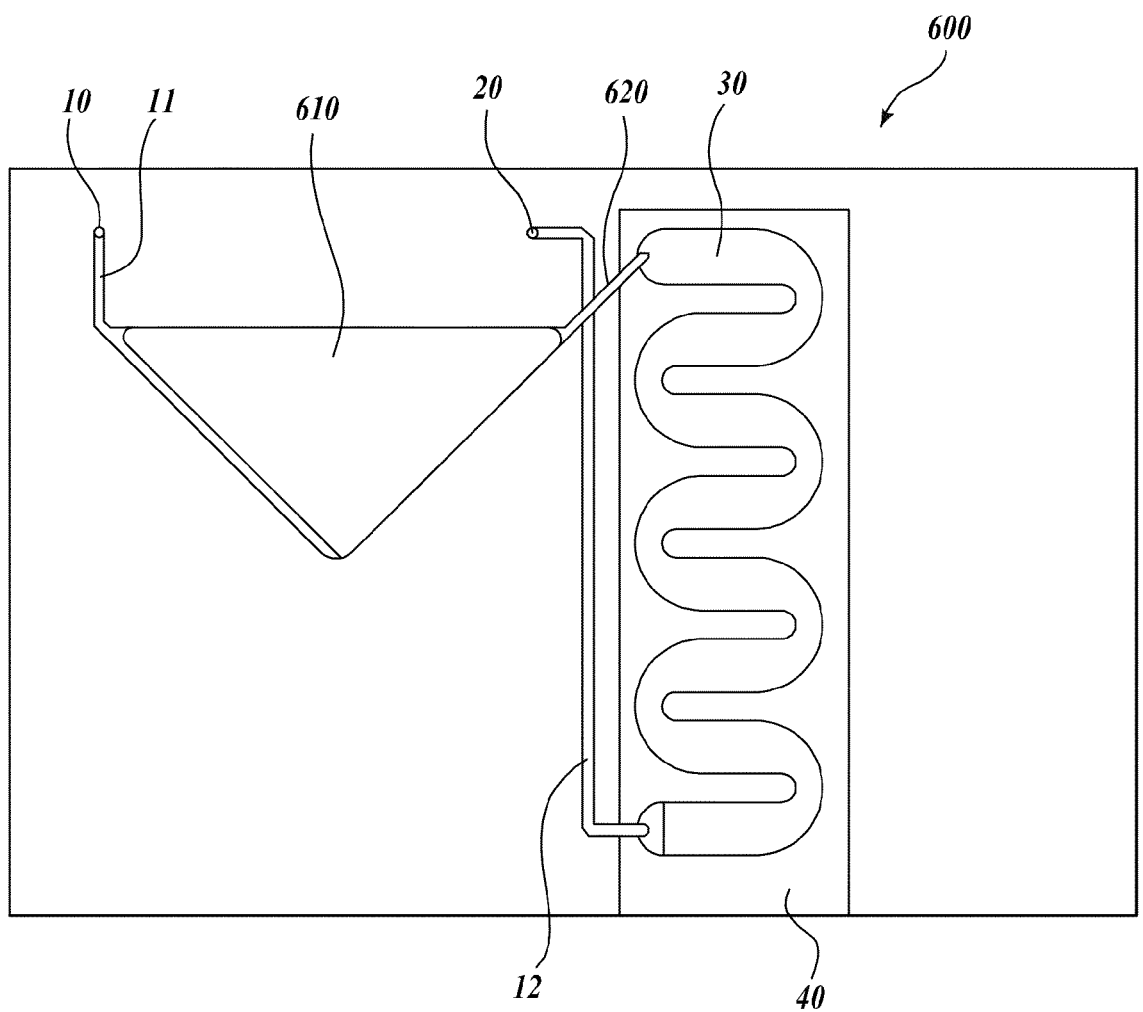
FIG. 9 is a schematic illustration of a representative device of the invention.

Devices of the present invention may further comprise additional chambers and channels. For example, device 600 shown in FIG. 9 includes first port 10, first channel 11, first chamber 610, intermediate channel 620, binding chamber 30, second channel 12, and second port 20. Glass slide 40 defines at least one surface of binding chamber 30. In certain embodiments, binding chamber 30 is defined by two glass slides (i.e., floor and ceiling of chamber 30). First chamber 610 is used for cell lysis and/or waste collection. Within device 600, cells from the sample can be lysed in the same vessel in which nucleic acid extraction and analysis is performed. In one embodiment, lysing the cells of the sample comprises contacting the cells with a chaotropic salt solution. Lysing the cells can also comprise sonicating or mechanically disrupting the cells in the sample in first chamber 610. Liquid can then be transferred from first chamber 610 into binding chamber 30 by rotating the device so that the liquid is transferred by gravity. Transferring the liquid may also include pumping. For example, after cell lysis and incubation device 600 is rotated clockwise 90 degrees and liquid is transported through intermediate channel 620 into binding chamber 30. Nucleic acids are captured on the glass surface of binding chamber 30, and wash solution is introduced into device 600 through second port 20. After washing, device 600 is tipped again to transport waste reagents back to first chamber 610, where they are stored for disposal.

Figure 10A:
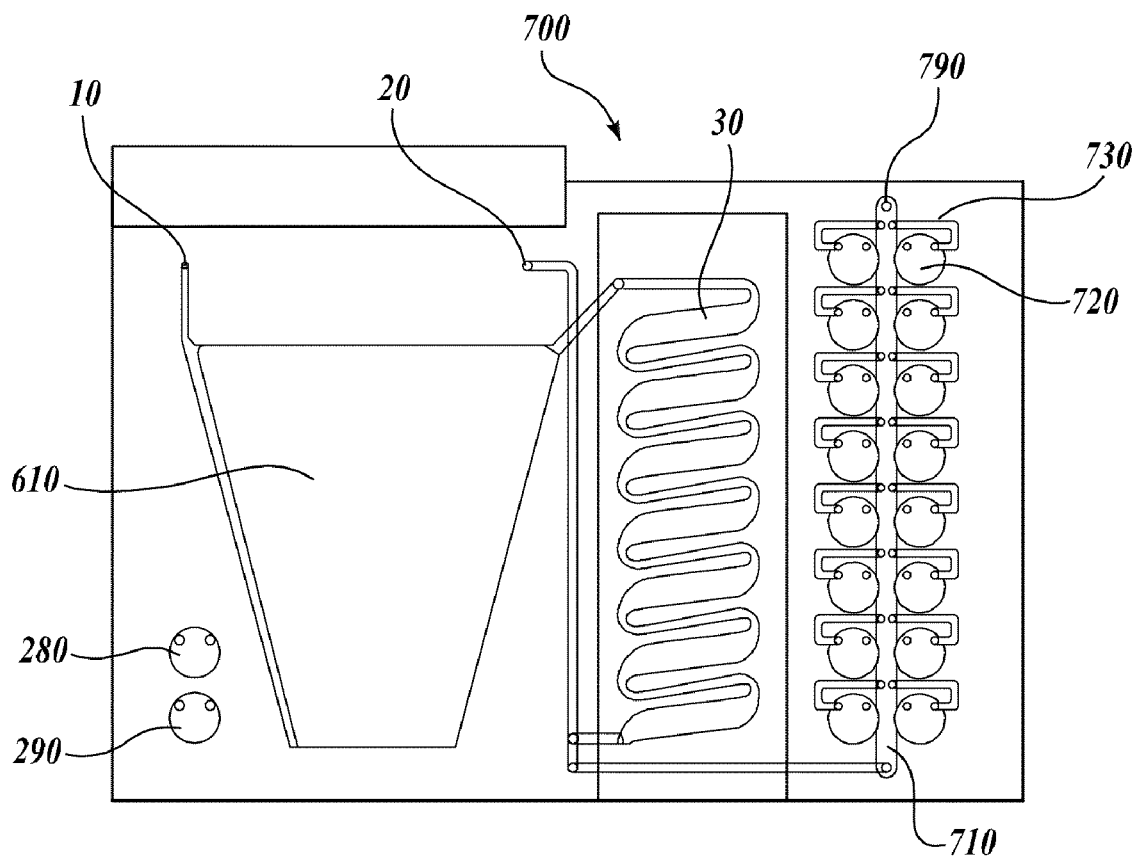
FIGS. 10A and 10B illustrate a device comprising a distribution channel and a plurality of capillary channels and assay wells.
Figure 10B:
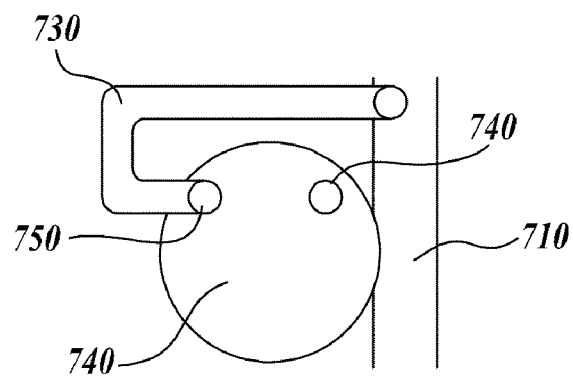

Devices of the invention can further comprise a distribution channel in fluid communication with the binding channel and a plurality of capillary channels in fluid communication with the distribution channel distal to the binding channel. The distribution channel and capillary channels provide a means for distributing fluid from the binding channel to assay wells either incorporated into the device or in a separate device. FIGS. 10A and 10B illustrate an example of a device comprising an integrated distribution channel and assay wells. The illustrated device 700 provides for distribution of extracted nucleic acid to multiple wells located on the device.

Referring to FIG. 10A, device 700 comprises first chamber 610, binding chamber 30, two calibration wells 280 and 290, distribution channel 710, and a plurality of assay wells 720. Although the illustrated device includes sixteen assay wells, devices containing more or fewer than sixteen wells can be constructed and are within the scope of the present invention. After nucleic acid is captured in binding chamber 30, washed, and eluted, it then flows in response to an applied pressure gradient to distribution channel 710 that is in fluid communication with assay wells 720. Each assay well is connected to distribution channel 710 by capillary channel 730 and further comprises a vent 740 as shown in FIG. 10B. Distribution channel 710 terminates in port 790. When port 790 is blocked, and if the surface energy of the capillary channels is sufficiently high, the eluent flows into and fills each capillary channel 730. Each capillary channel connects to an assay well through outlet via 750 cut through the plastic film layer separating capillary channel 730 from assay well 720. Due to a balance between the pressure forces causing fluid flow and the surface tension forces of the liquid meniscus, the liquid front in each capillary channel stops at its outlet via, instead of continuing to flow into its respective well. Once all the capillary channels are filled, any excess eluent is pushed from the distribution channel into first chamber 610 by applying air pressure to port 790 while port 20 is sealed (e.g., by covering them with tape). This ensures that each well will get the same volume of eluent. Then, an air pressure pulse is applied to distribution channel 710 via port 790 while ports 10 and 20 are sealed, and this pressure overwhelms the surface tension at each outlet via causing all the liquid eluent in each capillary channel to be emitted as droplets into its well. To ensure complete wetting of the capillary channels, the channel wall material should have a critical surface energy that is higher than the surface energy of the eluent. Critical surface energy (critical surface tension) can be determined by consulting material properties tables. Surface energy of the eluent is determined by measurement. See, Fox and Zisman, *J. Colloid. Science* 5:514, 1950; Zisman, "Relation of Equilibrium Contact Angle to Liquid and Solid Constitution", Chapter 1 in Contact Angle, Wettability, and Adhesion, R. F. Gould, ed., American Chemical Society, Washington D.C., 1964.

Elements illustrated in FIGS. 10A and 10B can be readily incorporated into devices of alternative design. For example, other such designs may omit first chamber 610 or calibration wells 280 and 290, may substitute a different binding chamber design, or may dispense the eluent to an external wellplate instead of to assay wells in the device. However, the basic concept of droplet distribution of the purified nucleic eluent remains the same.

Functions can be added to the devices of the present invention through attachment of additional modules. Such additional functions include, for example, cell lysis and automated distribution of purified DNA to a standard well plate or to multiple wells located on the device. An example of such device enhancement is disclosed with reference to FIG. 8A, although those skilled in the art will recognize that other device designs can be readily adapted to this system of functional modules. As shown therein, device 400 is provided with additional channels 490 in the form of vias that pass completely through the device. Thus, channels 490 can provide for passage of fluids between additional modules attached to the top and bottom surfaces of device 400. Use of these vias for expansion of device functionality allows continued use of existing layer patterns, thereby minimizing tooling costs and providing a modular assembly system. Additional modules are added during device fabrication by replacing individual layers or adding extra layers to the top and/or bottom surfaces. Typically, these additional layers are bonded to areas of the device containing ports to be used as manifold and pipette interfaces, and connect to first channel 11 and/or second channel 12 through other of the ports. Additional layers may further overlap glass slides 460. It is preferred that the overlapping material be clear to allow viewing through the device. Windows can be cut out of the overlapping material to facilitate use an optical reader. Additional modules introduce additional fluid pathways to the device. Control of fluid flow to choose the appropriate device function can be provided by valves.

High-throughput analysis outside the device may be facilitated via a microtiter plate format adapter. The adapter is of laminated construction with die-cut channels, and is preferably of the same or similar dimensions as the device of the invention. The channels include a main distribution channel and a series of capillary channels in fluid communication with the main channel in an arrangement similar to that illustrated in FIGS. 10A and 10B. This adapter is attached to the device of the invention through aligned ports to distribute a liquid solution (e.g., purified DNA elution or a common reagent) in equal amounts to each of the wells in a standard microtiter plate. The solution to be dispensed is moved through the main channel of the adapter as a bolus of liquid by a pump or by gravity. As the liquid bolus moves down the main channel it fills each capillary by capillary action. The liquid is then dispensed to the wells using a burst of air pressure as disclosed above. In an alternative configuration, each capillary is terminated by a capillary pore that is smaller in cross-section than the capillary itself and that serves to stop the fluid flow by surface tension at the end of the capillary. The small amount of liquid remaining at the end of the main channel wets a hydrophobic porous membrane and effectively seals the end of the channel, since liquid cannot pass through the membrane until forced by the air pressure. Micronozzles of this design can a predetermined quantity of liquid, typically 4-5 µL.

Devices of the present invention can further comprise one or more particles (beads) within the lysis chamber to facilitate disruption of cellular material. The use of beads in cell disruption is known in the art. For example, U.S. Pat. No. 6,235, 501 discloses methods of disrupting biological material to release nucleic acids wherein rapidly oscillating reciprocal mechanical energy is applied to the material. The biological material is suspended in a liquid medium with one or more particles, typically a spherical bead having a volume of about 5% to 80% of the liquid volume. Beads can be made from a variety of materials, including polytetrafluoroethylene, polypropylene, polyvinylchloride, ceramic, and stainless steel. In general, beads are selected for an appropriate size and hardness to disrupt the particular target cells.

Controlled oscillatory mechanical energy can be applied to the sample in the lysis chamber through an attached piezobuzzer. Piezobuzzers in the form of piezoceramic disks are known in the art and are available from commercial suppliers (e.g., Piezo Systems Inc., Woburn, Mass.). Such energy is applied to the sample for short periods of time (typically 5-60 seconds) to lyse the sample and release the DNA. Energy transfer and lysis are enhanced by including one or more particles as disclosed above. A piezobuzzer also facilitates mixing of liquids within the lysis chamber, such as mixing of blood and buffers. In the alternative, a sonicator probe or other device capable of introducing high frequency resonant vibrations through a wall of the device can be employed.

The devices can also be provided with one or more features to facilitate tracking of the device and nucleic acid products. Such features include bar coding and RF tracking elements.

Heating elements can be incorporated into the device in the form of electrical resistance heaters. Flexible heating elements constructed from a variety of materials, including silicone rubber, polyimide, mica, and polytetrafluoroethylene, are known in the art and are available from commercial suppliers (e.g., Minco, Minneapolis, Minn.) by attaching the heater directly to the outer surface of the device. In the alternative, separate, external heating elements can be pressed against the device to provide physical contact between the heating element and the device.

Liquid sensors in the form of electrical capacitance sensors can also be incorporated into the device. When two electrical conductors are separated by a dielectric material they form an electrical capacitor. By placing conductive films onto opposite outer surfaces of the device, one can form an electrical capacitor where the body of the device provides the dielectric material separating the two conductive films, and the overlapping areas of the two conductive films define the outer perimeter of the capacitor. Changes in dielectric properties due to liquids entering or leaving the region defined by the capacitor can be used to indicate the presence or absence of liquid. Electrical conductors can be imprinted onto the device surface by screen printing or other methods known in the art. In the alternative, electrical conductors can be provided by an external mechanism that is attached to the device to provide the electrical conductor portions of the capacitor.

In one embodiment, the device includes a pumping means effective for transporting fluids between the first port and the second port through the binding chamber. The pump is selected for its ability to meet the following criteria: (1) ability to dispense in the volumes in the range of 5 µl-1000 µl; (2) a low or zero dead volume to minimize cross contamination of fluids; (3) wetted surfaces made of materials compatible with the various reagents used (e.g., chaotropic salts and ethanol); (4) ability to effectively pump air as well as liquids; and (5) ability to operate in reverse. Peristaltic pumps offer a good working combination of all of these traits, but do not offer the most accurate volume dispensing of all pump options. When employing other pump styles, multiple pumps may be required for particular functions, thereby complicating the overall fluid management system. For example, syringe pumps can be used to deliver measured volumes of fluid into the device, but an additional means of pressurizing the system is required to move the fluid within the binding chamber and associated channels. In contrast, computer-controlled multi-channel peristaltic pumps (e.g., ISMATEC 12-channel pumps; Ismatec SA, Glattbrugg, Switzerland) will accommodate multiple devices simultaneously and can be programmed to start/stop/change flow rate or reverse direction of flow. Ordinarily, the pump is connected to the device port selected as the reagent inlet, and the port selected as the outlet is connected to a waste container, although other configurations are within the scope of the invention.

The device may further include fluid distribution control means in fluid communication with the pumping means. The fluid distribution control means comprises one or more valves that allow for a plurality of fluids to be sequentially pumped through the device, typically in the form of a valve-manifold block. It is preferred that manifold inputs and the exit pass through sterile filters to protect the valve-manifold assembly from contamination, and that the exit line have a check valve to prevent backflow from the pump tubing into the manifold. An exemplary fluid distribution control means is a model V-1241-DC 6-way selector valve manufactured by Upchurch Scientific, Oak Harbor, Wash. The fluid distribution control means may further comprise a programmable computer, either external to the valve mechanism or fully integrated therewith. In certain embodiments of the invention, the programmable computer is a desktop or laptop personal computer. In other embodiments, the programmable computer is a dedicated microprocessor device. In an exemplary system, control of fluid distribution is achieved using the above-disclosed selector valve in combination with a multi-channel peristaltic pump using an application written in Visual Basic for Microsoft Excel and running on a personal computer. Both the valve mechanism and the pump feature RS232 communication. These components are addressed using Excel through the USB port of the computer and a USB-to-Serial converter. As will be understood by those skilled in the art, custom firmware software may also be employed.

In addition, the device can be configured with high volume, low pressure air pump downstream of the pumping means disclosed above. This air pump is connected to the device by a two-position selector valve and is used to dry the interior of the device by evaporation.

Liquid reagents are conveniently stored in septum-sealed vials equipped with a sterile filter vent. The vials may be connected to the fluid distribution control means using a standard Luer-type needle inserted through the septum and connected to manifold inputs via microbore tubing.

The devices of the present invention can be constructed from the above-disclosed materials by conventional methods. For example, laminated plastic construction can be employed (e.g., as shown in FIG. 1A and FIG. 4B). For laminated assembly, individual layers are cut to shape. Methods for cutting polymeric materials (plastic) are known in the art and include, without limitation, laser cutting, CNC drag knife cutting, and die cutting. Adhesive layers are prepared to go between the layers of dry plastic. The adhesive layer will ordinarily be a pressure-sensitive adhesive available in a thin film that can be cut using the same method used for the plastic. Adhesives may be used in an Adhesive-Carrier-Adhesive (ACA) format where the carrier is preferred to be the same material as used in the other layers of the device. Other methods of applying liquid adhesives, such as screen printing, may also be employed. The several layers are registered to each other and pressed together. Features to assist in registration, such as alignment holes 15 shown in FIG. 1A, are advantageously incorporated into the final design. Pressure and temperature during the cure cycle are adhesive-dependent; selection of suitable conditions is within the level of ordinary skill in the art. In the alternative, the device can be assembled through the use of a compression seal as illustrated in FIGS. 3A and 3B.

After fabrication, the device is optionally treated with ethylene oxide or gamma sterilization to remove pathogens. Reagents for use with the device preferably pass a 0.2-micron cellulose filter on entry to remove bacterial and viral contaminants. Trace nucleic acid contaminants can be removed from reagents by ultrafiltration. For some applications, such as when isolating RNA or trace quantities of nucleic acids, it is beneficial to use nuclease-free reagents The reagent ports on the device may provide an interface to yellow (0.2 mL maximum) and blue (1.0 mL) pipette tips. A needle-septum interface can be provided.

Liquid samples are ordinarily introduced into the device at flow rate of approximately 0.1 mL/minute to approximately 5.0 mL/minute, although, as disclosed above, considerably higher flow rates can be used without disrupting laminar flow. The actual flow rate is design-dependent, taking into consideration the total volume of the fluid pathway and the shape of the binding chamber. As disclosed above, it is preferred to maintain laminar flow within the binding chamber. For devices comprising the larger volume S-Channel (FIG. 2A), a flow rate of approximately 2.5 mL/minute has been found to be satisfactory. For the smaller volume W-channel (FIG. 2B), the flow rate can be slowed to 0.5 mL/minute to 2.0 mL/minute, more preferably 1-1.5 mL/minute.

Dilute or concentrated samples can be prepared for input into the device. Lysis and digestion of intact cells releases DNA or RNA from residual proteins (for example histones). In the alternative, solid samples (e.g., bacterial spores or dried blood on cloth) or semisolid samples (e.g., mouse tails or sputum/stool) can be homogenized and lysed before input to the device to provide a homogeneous and non-viscous sample that will flow through the channels in the device.

Nucleic acids are bound to the glass surface(s) of the device in the presence of a salt (e.g., KCl) at a concentration of at least 0.5 M to about 2 M or more depending on solubility, or a chaotrope (e.g., guanidine HCl or guanidine thiocyanate) at a concentration of at least 1 M to about 6 M or the limit of solubility. Binding of nucleic acids is ordinarily done at a pH of approximately 5 to 8, preferably about 6. The binding chamber is then washed using buffered solutions of decreasing salt concentration. As salt concentration decreases, ethanol is added to the wash solution to retain the nucleic acid on the glass and to remove contaminants that may interfere with downstream processes such as nucleic acid amplification. Washing is carried out at pH 6-9, commonly pH 6-8. Nucleic acids are eluted from the device with a low-salt solution at basic pH, commonly pH 8-9.

In general, cells within the biological sample are lysed to provide a cell lysate from which the nucleic acids are extracted. A variety of methods of cell lysis are known in the art and are suitable for use within the invention. Examples of cell lysis methods include enzymatic treatment (using, for example, proteinase K, pronase, or subtilisin), mechanical disruption (e.g., by sonication, application of high pressure, or use of a piezobuzzer device), or chemical treatment. Lysing the cells of the sample by treating them with a chaotropic salt solution is particularly advantageous. Methods and reagents for lysing cells using chaotropic salts are known in the art, and reagents can be purchased from commercial suppliers. Specific reagent compositions and reaction conditions will be determined in part by the type of cell to be lysed, and such determination is within the level of ordinary skill in the art. Suitable chaotropic salts include guanidinium thiocyanate, guanidine hydrochloride, sodium iodide, and sodium perchlorate. Guanidine hydrochloride, which is preferred for lysing blood cells, is used at concentrations of 1M to 10M, commonly 1M to 5M, usually 1M to 3M. Higher concentrations of sodium iodide are required, approaching the saturation point of the salt (12M). Sodium perchlorate can be used at intermediate concentrations, commonly around 5M. Neutral salts such as potassium chloride and sodium acetate can also be used to obtain binding of DNA to glass surfaces, and may be used in place of chaotropic salts when cell lysis is not required or is achieved by other means (e.g., in the case of bacterial cell lysis). When using neutral salts, the ionic strength of the buffer should be at least 0.25M. An exemplary lysis buffer is a 2M solution of guanidinium thiocyanate (GuSCN) buffer at pH 6.4. Lysis in a chaotropic salt solution also removes histone proteins from the genomic DNA and inactivates nucleases. Lysis buffers will generally also contain one or more buffering agents to maintain a near-neutral to slightly acidic pH. A suitable buffering agent is sodium citrate. One or more detergents may also be included. Suitable detergents include, for example, polyoxyethylenesorbitan monolaurate (TWEEN 20), t-octylphenoxypolyethoxyethanol (TRITON X-100), sodium dodecyl sulfate (SDS), NP-40, CTAB, CHAPS, and sarkosyl. Alcohol, commonly ethanol, is included in the lysis and wash solutions, with the actual concentration selected to compensate for the lowered salt concentration in the washes. In the absence of salt, alcohol is included at a concentration of at least 50%, with 70% alcohol preferred in the final wash. If salt is included in the reagents, alcohol concentration will ordinarily range between 10% and 80%, often between 10% and 60%, usually between 20% and 50%. Optimization of buffers is within the level of ordinary skill in the art. Lysis is generally carried out between room temperature and about 95° C., depending on the cell type. Blood cells are conveniently lysed at room temperature. It is generally preferred that the use of silica particles in cell lysis be avoided, since silica particles may bind nucleic acids and reduce the efficiency of the extraction process. Although not necessary, DNA may be sheared prior to loading the lysate into the extraction device. Methods for shearing DNA are known in the art.

The nucleic acid-containing sample is introduced into the device via an one of the ports. Nucleic acid is captured on the flat glass surface(s) in the presence of a salt or chaotropic salt as disclosed above. Satisfactory binding of nucleic acids to glass is achieved at room temperature (15° C.-30° C., commonly about 20° C.), although the extraction process can be run at higher temperatures, such as up to 37-42° C. or up to 56° C., although higher temperatures may reduce recover of nucleic acids. The sample may be allowed to stand in the device for a period of time, and the sample solution may be pumped back and forth through the binding chamber. Wash buffers are then pumped into one port, such as by use of a peristaltic pump, a syringe, or a pipettor. Selection of wash buffers will depend in part on the composition of the sample loading solution. In general, salt concentration will be reduced during the washing process, and pH will be increased slightly. If the lysis buffer contains a chaotropic salt, the initial wash will commonly also contain that salt at the same or somewhat lower concentration (e.g., 1-3M GuSCN). The final wash should reduce the ethanol concentration to below 50%, preferably to about 10%-20%, to minimize inhibition of PCR amplification in downstream processing. The alcohol content of wash solutions will ordinarily range between 20% and 80%. Wash solutions containing at least 50% ethanol, preferably about 70% ethanol, have been found to improve nucleic acid capture. Complete removal of the final wash from the binding chamber is also needed in certain embodiments. Methods for this removal of the final wash include drying by passaging air over the surfaces of the chamber utilizing an air pump for one to three minutes. After washing, the nucleic acid is eluted from the binding chamber with a low salt buffer at higher pH than the final wash. Elution buffers are typically low ionic strength, buffered solutions at $pH \geq 8.0$, although nucleic acid can be eluted from the device with water. Elution can be carried out at ambient temperature up to about 56° C. The design of the device permits buffers to be pumped back and forth through the binding chamber to increase washing and elution efficiency, and air to be pumped through between washes to remove residual buffer. Buffers are ordinarily pumped through the binding chamber and out through the port selected as the device outlet.

As will be understood by those skilled in the art, actual working volumes will be determined by the size of the device, including binding chamber volume, as well as routine experimental design. For small-volume devices employing glass slides as the nucleic acid binding surface, volumes will ordinarily range from about 20 µl to 500 µl. Samples can be concentrated by reducing the volume of the elution volume buffer.

Quantitation of extracted nucleic acids is facilitated by the inclusion of a fluorescent compound within the elution buffer, thereby providing a rapid quality check on the extraction process while the extracted nucleic acids are still within the device. Thus, within one embodiment of the invention the nucleic acids are contacted with a fluorescent compound having a fluorescence intensity dependent on the concentration of nucleic acids, and the fluorescence of the fluorescent compound is measured. Fluorescent compounds having a fluorescence intensity dependent on the concentration of nucleic acids are fluorescent compounds that exhibit a conformation-dependent change in fluorescence intensity in the presence of nucleic acids. Useful fluorescent compounds include those compounds whose intensity increases in the presence of nucleic acids. Representative fluorescent compounds include fluorogenic minor groove binder agents such as bis-benzimide compounds, intercalating fluorogenic agents such as ethidium bromide, and commercially available fluorescent dyes (e.g., SYBR Green; Invitrogen Corp.). Fluorescent compounds can be introduced into the device in the elution buffer. Methods for immobilizing the fluorescent compound in the binding chamber and useful fluorescent compounds are described below and in Reed et al., US 2006/0166223 A1. The device of the invention allows for the interrogation of the binding chamber by fluorescence by having at least a portion of the chamber suitable for transmitting excitation energy to the fluorescent compounds in the binding chamber and for transmitting fluorescence emission intensity from the compounds in the binding chamber.

Although in principal any fluorogenic DNA-binding dye can be used in the invention, it is preferred to use a dye that is compatible with downstream processes such as PCR. A preferred dye is a bis-benzimide (BB) dye disclosed by Reed et al., US Patent Application Publication 20060166223 A1, which gives a strong fluorescent signal (detection at 460 nm, 40 nm filter slit width) when excited at 360 nm (40 nm slit width). The BB dye is selective for dsDNA but can also detect RNA. A popular green fluorescent dye, SYBR green (Invitrogen Corp.) is often used in so called "real time" PCR or quantitative PCR. Much like the BB dye, SYBR green can be used to both quantitate the extracted DNA before amplification and monitor the gene-specific increase during PCR. The use of fluorogenic DNA dyes or DNA probes in isothermal nucleic acid tests such as NASBA is also known.

The preferred bis-benzimide dye, although not as sensitive as some DNA-binding dyes, has been found to be well suited for measuring genomic DNA content of a sample after extraction from DNA-rich whole blood. The minor groove-binding BB dye emits blue fluorescence in the presence of double stranded DNA, and can be added directly to PCR amplification buffer. In contrast, DNA dyes with a higher binding affinity, such as PICOGREEN (Invitrogen), may inhibit PCR.

Preliminary evidence indicates that the BB dye can be used in existing PCR assays if the PCR primer extension is carried out at higher annealing temperature (61.5° C. vs. 60° C.). Inclusion of the BB dye directly in the elution buffer therefore allows DNA to be measured before, during, and after gene-specific amplification. The higher primer extension temperature required with addition of BB dye may be advantageous in PCR assays (acting as a PCR enhancer). Much like the MGB TaqMan system (U.S. Pat. No. 6,727,356), A/T rich primer/target interactions are stabilized by the BB in the PCR mix, and increased duplex stability allows shorter (more specific) DNA probes to be used. The blue emitting MGB dye will likely not interfere with the green to red fluorescence wavelengths that are widely used with 2-color fluorogenic DNA probes.

RNA-selective dyes such as Ribogreen (see Molecular Probes Handbook of Fluorescent Probes and Research Products, 9th edition, Chapter 8) can also be used in the device or elution buffer. RNA-selective dyes may have advantages for real time RNA assays such as NASBA. The caveats disclosed above about inhibition of the gene-specific DNA or RNA tests also apply to RNA detecting fluorogenic dyes.

If desired, the device can be re-used following removal of residual nucleic acids and/or reagents by washing. In many cases, satisfactory washing can be achieved by running several (typically 5-10) channel volumes of distilled sterile water through the binding chamber. In a preferred method, the device is first washed with 5-10 channel volumes of distilled sterile water, followed by a wash with 2-3 channel volumes of 70% EtOH, which is followed by another 2-3 channel volume wash with distilled sterile water. Wash solutions can be pumped through the device using a pump (e.g., a peristaltic pump), syringe, or the like. The cleaning protocol can be carried out in through a manifold using an automated pump. Following washing, the device is fully dried, such as in a vacuum dessicator for 5-30 minutes.

Bound nucleic acid can be stored in the device and used in later testing, including confirmation of test results. The device is rinsed with an ethanol-rich rinse and dried. Storage is at room temperature for up to several days or in a freezer for longer periods.

The present invention has multiple applications in laboratory research, human and veterinary medicine, public health and sanitation, forensics, anthropological studies, environmental monitoring, and industry. Such applications include, without limitation, bacterial and viral detection and typing, microbial drug resistance screening, viral load assays, genotyping, infection control and pathogen screening (of, e.g., blood, tissue, food, cosmetics, water, soil, and air), pharmacogenomics, detection of cell-free DNA in plasma, white cell counting, and other fields where preparation and analysis of DNA from biological samples is of interest. As disclosed above, nucleic acids extracted using the devices and methods of the invention are readily used in a variety of downstream processes, including amplification, hybridization, blotting, and combinations thereof. The devices and methods of the invention can be employed within point-of-care diagnostic assays to identify disease pathogens, and can be utilized in genetic screening. These devices and methods can also be used within veterinary medicine for the diagnosis and treatment of animals, including livestock and companion animals such as dogs, cats, horses, cattle, sheep, goats, pigs, etc.

Nucleic acids can be extracted from a wide variety of sources. For research and medical applications, suitable sources include, without limitation, sputum, saliva, throat swabs, oral rinses, nasopharyngeal swabs, nasopharyngeal aspirates, nasal swabs, nasal washes, mucus, bronchial aspirations, bronchoalveolar lavage fluid, pleural fluid, endotracheal aspirates, cerbrospinal fluid, feces, urine, blood, plasma, serum, cord blood, blood components (e.g., platelet concentrates), blood cultures, peripheral blood mononuclear cells, peripheral blood leukocytes, plasma lysates, leukocyte lysates, buffy coat leukocytes, anal swabs, rectal swabs, vaginal swabs, endocervical swabs, semen, biopsy samples, lymphoid tissue (e.g., tonsil, lymph node), bone marrow, other tissue samples, bacterial isolates, vitreous fluid, amniotic fluid, breast milk, and cell culture supernatants. Other starting materials for extraction of nucleic acids include water samples, air samples, soil samples, cosmetics, foods and food ingredients, medical supplies and equipment, and the like.

Nucleic acids prepared according to the present invention can be amplified by methods known in the art, including polymerase chain reaction (PCR) (see, e.g., Mullis, U.S. Pat. No. 4,683,202) and isothermal amplification methods. Real-time polymerase chain reaction (RT-PCR) is commonly used. See, for example, Cockerill, *Arch. Pathol. Lab. Med.* 127: 1112-1120, 2002; and Cockerill and Uhl, "Applications and Challenges of Real-Time Pcr for the Clinical Microbiology Laboratory," pp. 3-27 in Reischl et al, eds., *Rapid cycle real-time PCR methods and applications*, Springer-Verlag, Berlin, 2002. For a review of the use of RT-PCR in clinical microbiology, see Espy et al., *Clin. Microbiol. Rev.* 19:165-256, 2006. Instrumentation and chemistry for carrying out PCR are commercially available. Instruments include thermal cyclers (e.g., ABI7000, 7300, 7500, 7700, and 7900, Applied Biosystems, Foster City, Calif.; LIGHTCYCLER, Roche Applied Science, Indianapolis, Ind.; SMARTCYCLER, Cepheid, Sunnyvale, Calif.; ICYCLER, Bio-Rad Laboratories, Inc., Hercules, Calif.; ROBOCYCLER and MX3000P, Stratagene, La Jolla, Calif.), detection systems for use with fluorescent probes (e.g., MYIQ and CHROMO4, Bio-Rad Laboratories, Inc.), nucleic acid analyzers (e.g., Rotor-Gene 6000, Corbett Life Science, Concorde, NSW, Australia), and amplification and detection systems (e.g., BD PROBETEC ET, Becton Dickinson, Franklin Lakes, N.J.). Other PCR technologies include fluorescent dyes for quantitative PCR (e.g., SYBR, Invitrogen Corp.) and fluorogenic probes, including FRET (fluorescent resonance energy transfer) hybridization probes (Walker, *Science* 296:557-559, 2002), TAQMAN probes (Applied Biosystems, Foster City, Calif.; see, Kutyavin et al., *Nucl. Acids. Res.* 28:655-661, 2000), ECLIPSE probes (Nanogen, Bothell Wash.), and molecular beacons (U.S. Pat. Nos. 5,925,517 and 6,150,097. Isothermal amplification methods known in the art include nucleic acid sequence-based amplification (NASBA) (Malek et al., U.S. Pat. No. 5,130,238; Compton, *Nature* 350:91-92, 1991; Deiman et al., *Mol. Biotechnol.* 20:163-179, 2002), branched DNA (Alter et al., *J Viral Hepat.* 2:121-132, 1995; Erice et al., *J. Clin. Microbiol.* 38:2837-2845, 2000), transcription mediated amplification (Hill, *Expert. Rev. Mol. Diagn.* 1:445-455, 2001), strand displacement amplification (Walker, *PCR Methods and Applications* 3:1-6, 1993; Spargo et al., *Mol. Cell Probes* 10:247-256, 1996), helicase-dependent amplification (Vincent et al., *EMBO Rep.* 5:795-800, 2004), loop-mediated isothermal amplification (Notomi et al., *Nucl. Acids Res.* 28:E63, 2000), INVADER assay (Olivier et al., *Nucl.*

Acids Res. 30:e53, 2002; Ledford et al., *J. Mol. Diagn.* 2:97-104, 2000), cycling probe technology (Duck et al., *BioTechniques* 9:142-148, 1990; Cloney et al., *Mol. Cell Probes* 13:191-197, 1999), rolling circle amplification (Fire and Xu, *Proc. Nat. Acad. Sci. USA* 92:4641-4645, 1995; Liu et al., *J. Am. Chem. Soc.* 118:1587-1594, 1996), and Q-beta replicase (Shah et al., *J. Clin. Microbiol.* 32:2718-2724, 1994; Shah et al., *J. Clin. Microbiol.* 33:1435-1441, 1995). For a review of isothermal amplification methods, see Gill and Ghaemi, *Nucleosides Nucleotides Nucleic Acids* 27:224-243, 2008.

NASBA depends on the concerted action of three enzymes to amplify target nucleic acid sequences. While able to amplify double-stranded DNA, NASBA is particularly suited for amplification of RNA. Target RNA enters the cycle by binding to a first primer, which is then extended by reverse transcriptase to form a DNA/RNA hybrid. The RNA strand is removed by the action of RNase H to yield a single-stranded cDNA. This cDNA can bind to a second primer (which includes a T7 RNA polymerase promoter sequence) and then form a double-stranded intermediate by the action of the reverse transcriptase activity. The intermediate is then copied by the action of T7 RNA polymerase into multiple single-stranded RNA copies (10-1000 copies per copy of template). These RNA copies can then enter the cycle and continue generating more copies in a self-sustained manner. Based on the NASBA mechanism, two products can be detected: a double-stranded DNA intermediate and a single-stranded RNA product.

NASBA is conveniently used with the devices of the present invention since it is isothermal (i.e. temperature cycling is not required). A denaturation step is not necessary except when a DNA target is chosen. Two considerations when running NASBA in the devices of the present invention are heat transfer and protein adsorption. The reaction temperature should be within the range of 30° C. to 50° C., usually at least 37° C., and preferably 42° C. where primer binding is more specific. Room temperature does not support NASBA, so the channel temperature must be raised efficiently or the reaction will not work. In addition, proteins such as the NASBA enzymes readily stick to glass and some organic polymeric materials, inactivating them and stopping the NASBA cycle. Two methods to address this are (1) to preadsorb the glass with a carrier such as serum albumin, or (2) to add enough serum albumin to the NASBA reaction mixture to minimize loss of enzymes.

Additional methods of nucleic acid amplification are known in the art and can be applied to DNA prepared according to the present invention. Examples of such methods include ligase chain reaction (Wu and Wallace, *Genomics* 4:560-569, 1989; Barany, *Proc. Natl. Acad. Sci. USA* 88:189-193, 1991), polymerase ligase chain reaction (Garany, *PCR Methods and Applic.* 1:5-16, 1991), gap ligase chain reaction (Segev, WO 90/01069), repair chain reaction (Backman et al., U.S. Pat. No. 5,792,607), and rolling circle amplification (RCA) (Lisby, *Mol. Biotechnol.* 12:75-99, 1999).

As will be understood by those of ordinary skill in the art, nucleic acids prepared according to the present invention can also be detected and/or analyzed without amplification using methods known in the art. Suitable methods include, without limitation, hybridization, which can be coupled to fluorescence or immunoassay, including hybridization to oligonucleotide-nanoparticle conjugates (Park et al., U.S. Pat. No. 7,169,556) and DNA barcodes (Mirkin et al., US 2006/0040286 A1); microarray technology, which can be used for expression profiling by hybridization, diagnostics, gene identification, polymorphism analysis, and nucleic acid sequencing; hybridization protection assay (Arnold et al., *Clin. Chem.* 35:1588-1594, 1989); dual kinetic assay (e.g., APTIMA COMBO 2 assay, Gen-Probe Incorporated); and sequencing, including microsequencing (e.g., MICROSEQ 500 16s rDNA bacterial identification kit, Applied Biosystems). Methods of detecting polymorphisms include massively parallel shotgun sequencing (Nature 437:326-327, 2005), which can detect previously unknown features of cell-free nucleic acids such as plasma mRNA distributions and/or methylation and histone modification of plasma DNA (Fan et al., *Proc. Natl. Acad. Sci. USA* 105:16266-16271, 2005) Those of ordinary skill in the art will further recognize that these and other methods can be used in combination with nucleic acid amplification.

As noted above, extracted nucleic acids can be used within methods for detecting pathogens, including bacteria, viruses, fungi, and parasites. In addition, extracted nucleic acids can be analyzed to characterize drug resistance and drug sensitivity of infectious agents (e.g., methicillin or other antibiotic resistance in *Staphylocccus aureus*). Many such methods are known in the art, and a number of such tests have been approved by the US Food and Drug Administration for human diagnostic use and are commercially available. For example, Table 2 is a list of FDA-approved tests for *Chlamydia*. Additional tests are listed in Table 3. Other pathogens of interest for which nucleic acid-based tests are known include blood-borne pathogens, *Coccidioides immitis, Cryptococcus, Gardnerella vaginalis, Haemophilus* spp., *Histoplasma capsulatum*, influenza virus, *Mycoplasma* spp., *Salmonella* spp., *Shigella* spp., and *Trichomonas vaginalis*. Methods for the detection of microbial contaminants, including bacteria, viruses, fungi, and parasites, in samples of foods and other products using PCR are disclosed by, for example, Romick et al., U.S. Pat. No. 6,468,743 B1. The use of PCR in testing water samples for *Enterococcus* species is disclosed by Frahm and Obst, *J. Microbiol. Methods* 52:123-131, 2003.

TABLE 2

| PRODUCT | COMPANY | APPROVAL DATE | DESCRIPTION |
| --- | --- | --- | --- |
| AMPLICOR CT/NG TEST FOR *CHLAMYDIA TRACHOMATIS* | ROCHE DIAGNOSTICS CORPORATION | Apr. 16, 2007 | http://www.fda.gov/cdrh/pdf7/k070174.pdf |
| GEN-PROBE APTIMA ASSAY FOR *CHLAMYDIA TRACHOMATIS* | GEN-PROBE INC. | Jan. 22, 2007 | http://www.fda.gov/cdrh/pdf6/k063451.pdf |
| APTIMA CT ASSAY ON THE TIGRIS DTS SYSTEM | GEN-PROBE INC. | Oct. 13, 2006 | http://www.fda.gov/cdrh/pdf6/k061413.pdf |
| COBAS AMPLICOR CT/NG TEST | ROCHE DIAGNOSTICS CORP. | Aug. 10, 2006 | http://www.fda.gov/cdrh/pdf5/k053287.pdf |
| GEN-PROBE APTIMA ASSAY | GEN-PROBE INC. | Jul. 25, 2006 | http://www.fda.gov/cdrh/pdf5/k053446.pdf |
| GEN-PROBE APTIMA ASSAY | GEN-PROBE INC. | Jan. 27, 2005 | http://www.fda.gov/cdrh/pdf4/k043072.pdf |
| ROCHE AMPLICOR CT/NG TEST | ROCHE MOLECULAR SYSTEMS INC. | Aug. 4, 1999 | http://www.fda.gov/cdrh/pdf/k973707.pdf |

TABLE 2-continued

| PRODUCT | COMPANY | APPROVAL DATE | DESCRIPTION |
|---|---|---|---|
| ROCHE COBAS AMPLICOR CT/NG TEST | ROCHE MOLECULAR SYSTEMS INC. | Dec. 15, 1998 | http://www.fda.gov/cdrh/pdf/k973718.pdf |
| ROCHE COBAS AMPLICOR *CHLAMYDIA TRACHOMATIS* TEST | ROCHE MOLECULAR SYSTEMS INC. | Jun. 13, 1997 | http://www.fda.gov/cdrh/pdf/k964507.pdf |
| GEN-PROBE AMPLIFIED *CHLAMYDIA TRACHOMATIS* ASSAY K | GEN-PROBE INC. | Nov. 27, 1996 | http://www.fda.gov/cdrh/pdf/k962217.pdf |
| LCX *CHLAMYDIA TRACHOMATIS* ASSAY | ABBOTT LABORATORIES | Dec. 8, 1995 | Description for K934622 available from the Company |

TABLE 3

| Test | References/Products |
|---|---|
| General bacterial contamination of platelet concentrates | Dreier et al., *J.Clin.Microbiol.* 42: 4759-4764, 2004. Mohammadi et al., *J. Clin. Microbiol.* 41: 4796-4798, 2003 |
| *Bacillus anthracis* | Bell et al., *J. Clin. Microbiol.* 40: 2897-2902, 2002; Oggioni et al. *J. Clin. Microbiol.* 40: 3956-3963, 2002; Ellerbrok et al., *FEMS Microbiol. Lett.* 214: 51-59, 2002. |
| *Bartonella henselae* | Zeaiter et al. *J. Clin. Microbiol.* 41: 919-925, 2003. |
| *Bordetella pertussis* | Reischl et al., *J. Clin. Microbiol.* 39: 1963-1966, 2001; Anderson et al., *Clin. Microbiol. Infect.* 9: 746-749, 2003. |
| *Borrelia burgdorferi* | Makinen et al., "Genospecies-specific melting temperature of the recA PCR product for the detection of *Borellia burgdorferi* sensu lato and differentiation of *Borrelia garinii* from *Borrelia afzelii* and *Borrelia burgdorferi* sensu stricto," pp. 139-147 in Reischl et al., eds., *Rapid cycle real-time PCR methods and applications*, Springer-Verlag, Berlin, 2002 |
| *Borrelia garinii* | Pietila et al., *J. Clin. Microbiol.* 38: 2756-2759, 2000. |
| *Borrelia afzelii* | Pietila et al., *J. Clin. Microbiol.* 38: 2756-2759, 2000. |
| *Campylobacter* | Popovic-Uroic et al., *Lab Medicine* 22: 533-539, 1991; Tenover, *J. Clin. Microbiol.* 28: 1284-1287, 1990. |
| *Chlamydia* | Gaydos et al., *J. Clin. Microbiol.* 41: 304-309, 2003; Ikeda-Dantsuji et al., *J. Med. Microbiol.* 54: 357-360, 2005 |
| *Chlamydophila pneumoniae* | Apfalter et al., *J. Clin. Microbiol.* 41: 592-600, 2003; Tondella et al., *J. Clin. Microbiol.* 40: 575-583, 2002. |
| *Clostridium difficile* | Belanger et al., *J. Clin. Microbiol.* 41: 730-734, 2003. |
| *Ehrlichia chaffeensis* | Loftis et al., *J. Clin. Microbiol.* 41: 3870-3872, 2003. |
| *Enterococcus* Species | *E. faecalis*/OE PNA FISH assay, AdvanDx, Inc., Woburn, MA; see, Sloan et al., *J. Clin. Microbiol.* 42: 2636-2643, 2004. |
| *Escherichia coli* | Frahm and Obst, *J. Microbiol. Methods* 52: 123-131, 2003 |
| *Histoplasma capsulatum* | Hall et al., *J. Clin. Microbiol.* 30: 3003-3004, 1992. |
| *Legionella pneumophila* | Wellinghausen et al., "Rapid detection and simultaneous differentiation of *Legionella* spp. and *L. pheumophila* in potable water samples and respiratory specimens by LightCycler PCR," pp. 45-57 in Reischl et al. eds., *Rapid cycle real-time PCR methods and applications*, Springer-Verlag, Berlin, 2002; Welti et al., *Diagn. Microbiol. Infect. Dis.* 45: 85-95, 2003. |
| *Legionella* spp. | Herpers et al., *J. Clin. Microbiol.* 47: 4815-4816, 2003; Reischl et al., *J. Clin. Microbiol.* 40: 3814-3817, 2002. |
| *Listeria monocytogenes* | Okwumabua et al., *Res. Microbiol.* 143: 183-189, 1992. |
| *Mycobacterium* Spp. | Hall et al., *J. Clin. Microbiol.* 41: 1447-1453, 2003; Lumb et al., *Pathology* 25: 313-315, 1993 |
| *Mycobacterium tuberculosis* | e.g., AMPLICOR MTB, Roche Molecular Diagnostics, Pleasanton, CA. See, e.g., Stevens et al., *J. Clin. Microbiol.* 40: 3986-3992, 2002; Garcia-Quintanilla et al., *J. Clin. Microbiol.* 40: 4646-4651, 2002; Bruijnesteijn et al., *J. Clin. Microbiol.* 42: 2644-2650, 2004; Sedlacek et al., *J. Clin. Microbiol.* 42: 3284-3287, 2004. |
| Ethambutol resistance in *M. tuberculosis* | Wada et al., *J. Clin. Microbiol.* 42: 5277-5285, 2004. |
| Isoniazid resistance in *M. tuberculosis* | van Doorn et al., *J. Clin. Microbiol.* 41: 4630-4635, 2003; |
| Rifampin resistance in *M. tuberculosis* | Edwards et al., *J. Clin. Microbiol.* 39: 3350-3352, 2001; Piatek et al., *Nat. Biotechnol.* 16: 359-363, 1998. |
| *Mycobacterum ulcerans* | Rondini et al., *J. Clin. Microbiol.* 41: 4231-4237, 2003. |
| *Mycoplasma pneumoniae* | Welti et al., *Diagn. Microbiol. Infect. Dis.* 45: 85-95, 2003; Ursi et al., *J. Microbiol. Methods* 55: 149-153, 2003. |
| *Neisseria gonorrhoeae* | BD PROBETEC ET, Becton Dickinson, Franklin Lakes, NJ; APTIMA COMBO 2 assay, Gen-Probe Incorporated, San Diego, CA. Gaydos et al., ". |
| *Neisseria meningitides* | Guiver et al., *FEMS Immunol. Med. Microbiol.* 28: 173-179, 2000; Corless et al., *J. Clin. Microbiol.* 39: 1553-1558, 2001. |

TABLE 3-continued

| Test | References/Products |
| --- | --- |
| Penicillin resistance in *N. meningitides* | Stefanelli et al. *J. Clin. Microbiol.* 41: 4666-4670, 2003. |
| *Staphylococcus aureus* | *S. aureus* PNA FISH assay, Advandx, Inc., Woburn, MA |
| Fluoroquinolone resistance in *S. aureus* | Lapierre et al., *J. Clin. Microbiol.* 41: 3246-3251, 2003. |
| Methicillin Resistant *Staphylococcus aureus* | e.g., XPERT MRSA (Cepheid, Sunnyvale, CA); See, e.g., Reischl et al., *J. Clin. Microbiol.* 38: 2429-2433, 2000; Tan et al., *J. Clin. Microbiol.* 39: 4529-4531, 2002; Fang and Hedin, *J. Clin. Microbiol.* 41: 2894-2899, 2003; Francois et al., *J. Clin. Microbiol.* 41: 254-260, 2003; Ramakrishnan et al., US 20060057613 A1). |
| *Streptococcus pneumoniae* | Greiner et al., *J. Clin. Microbiol.* 39: 3129-3134, 2001. |
| Penicillin resistance in *S. pneumoniae* | Kearns et al. *J. Clin. Microbiol.* 40: 682-684, 2002. |
| Group A *Streptococcus* | Uhl et al., *J. Clin. Microbiol.* 41: 242-249, 2003. |
| Group B *Streptococcus* | CEPHEID SMART GBS ASSAY (Cepheid, Sunnyvale, CA); Bergeron et al., *N. Engl. J. Med.* 343: 175-179, 2000; Ke et al., "Rapid detection of group B *streptococci* using the LightCycler instrument," pp. 107-114 in Reischl et al, eds., *Rapid cycle Real-time PCR methods and applications*, Springer-Verlag, Berlin, 2002. |
| *Tropheryma whipplei* | Fenollar et al. *J. Clin. Microbiol.* 40: 1119-1120, 2002. |
| *Yersinia pestis* | Tomaso et al., *FEMS Immunol. Med. Microbiol.* 38: 117-126, 2003. |
| Fluoroquinolone resistance in *Y. pestis* | Lindler et al., *J. Clin. Microbiol.* 39: 3649-3655, 2001. |

Tests for detection and diagnosis of viruses are also known in the art. Examples of such tests are shown in Table 4.

TABLE 4

| Test | References/Products |
| --- | --- |
| Adenovirus | Houng et al., *Diagn. Microbiol. Infect. Dis.* 42: 227-236, 2002; Heim et al., *J. Med. Virol.* 70: 228-239, 2003; Faix et al., *Clin. Infect. Dis.* 38: 391-397, 2004; Lankester et al., *Clin. Infect. Dis.* 38: 1521-1525, 2004. |
| B19 virus | Koppelman et al., *Transfusion* 44: 97-103, 2004. |
| BK virus | Whiley et al., *J. Clin. Microbiol.* 39: 4357-4361, 2001. |
| Cytomegalovirus | Machida et al., *J. Clin. Microbiol.* 38: 2536-2542, 2000; Nitsche et al., *J. Clin. Microbiol.* 38: 2734-2737, 2000; Tanaka et al., *J. Med. Virol.* 60: 455-462, 2000; Gault et al., *J Clin. Microbiol.* 39: 772-775, 2001; Ando et al., *Jpn. J. Ophthalmol.* 46: 254-260, 2002; Aberle et al., *J. Clin. Virol.* 25 (Suppl. 1): S79-S85; Cortez et al., *J. Infect. Dis.* 755: 967-972, 2003; Hermann et al., *J. Clin. Microbiol.* 42: 1909-1914, 2004; Hall, U.S. Pat. No. 7,354,708. |
| Enterovirus | Read et al., *J. Clin. Microbiol.* 39: 3056-3059, 2001; Corless et al., *J. Med. Virol.* 67: 555-562, 2002; Kares et al., *J. Clin. Virol.* 29: 99-104, 2004. |
| Epstein-Barr Virus | Lo et al., *Clin. Cancer Res.* 7: 1856-1859, 2001; van Esser et al., *Br. J. Haematol.* 113: 814-821, 2001; Patel et al., *J. Virol. Methods* 109: 221-233, 2003; Balandraud et al., *Arthritis Rheum.* 48: 1223-1228, 2003; Jebbink et al., *J. Mol. Diagn.* 5: 15-20, 2003. |
| Hepatitis A virus | Costa-Mattioli et al., *J. Viral Hepat.* 9: 101-106, 2002; Rezende et al., *Hepatology* 35: 613-618, 2003. |
| Hepatitis B Virus | Abe et al., *J. Clin. Microbiol.* 37: 2899-2903, 1999; Ide et al., *Am. J. Gastroenterol.* 98: 2048-2051, 2003; Aliyu et al., *J. Clin. Virol.* 30: 191-195, 2004; Candotti et al., *J. Virol. Methods* 118: 39-47, 2004; |
| Hepatitis C Virus | VERSANT HCV RNA 3.0 Assay (Bayer Healthcare, Tarrytown NY), COBAS AMPLICOR HCV TEST (Roche Molecular Diagnostics); Enomoto et al., *J. Gastroenterol. Hepatol.* 16: 904-909, 2001; Schroter et al., *J. Clin. Microbiol.* 39: 765-768, 2001; Bullock et al., *Clin. Chem.* 48: 2147-2154, 2002; Candotti et al., "; Law et al., US 2007/0207455. |
| Hepatitis D Virus | Yamashiro et al., *J. Infect. Dis.* 189: 1151-1157, 2004 |
| Hepatitis E Virus | Orru et al., *J. Virol. Methods* 118: 77-82, 2004 |
| Herpes simplex virus | Espy et al., *J. Clin. Microbiol.* 38: 3116-3118, 2000; Kessler et al., *J. Clin, Microbiol.* 38: 2638-2642, 2000; Aberle and Puchhammer-Stockl, *J. Clin. Virol.* 25(Suppl. 1): S79-S85, 2002; Kimura et al., *J. Med. Virol.* 67: 349-353, 2002. |

TABLE 4-continued

| Test | References/Products |
|---|---|
| Human herpes virus subtypes | Aslanukov et al., US 2006/0252032 A1. |
| HIV-1 | Ito et al., *J. Clin. Microbiol.* 41: 2126-2131, 2003; Palmer et al., *J. Clin. Microbiol.* 41: 4531-4536, 2003; Candotti et al., ''; Gibellini et al., *J. Virol. Methods* 115: 183-189, 2004; |
| HIV-2 | Schutten et al., *J. Virol. Methods* 88: 81-87, 2000; Ruelle et al., *J. Virol. Methods* 117: 67-74, 2004 |
| Human Papillomavirus | King, US 2008/0187919 A1; Hudson et al., US 2007/0111200 A1. |
| JC virus | Whiley et al., ''. |
| Influenza Virus | van Elden et al., *J. Clin. Microbiol.* 39: 196-200, 2001; Smith et al., *J. Clin. Virol.* 28: 51-58, 2003; Boivan et al., *J. Infect. Dis.* 188: 578-580, 2003; Ward et al., *J. Clin. Virol.* 29: 179-188, 2004. |
| Metapneumovirus | Cote et al., *J. Clin. Microbiol.* 41: 3631-3635, 2003; Maertzdorf et al., *J. Clin. Microbiol.* 42: 981-986, 2004. |
| Orthopoxvirus | Espy et al., *J. Clin. Microbiol.* 40: 1985-1988, 2002; Sofi Ibrahim et al., *J. Clin. Microbiol.* 41: 3835-3839, 2003; Nitsche et al., *J. Clin. Microbiol.* 42: 1207-1213, 2004. |
| Parainfluenza Virus | Templeton et al., *J. Clin. Microbiol.* 42: 1564-1569, 2004; Templeton et al., *J. Clin. Virol.* 29: 320-322, 2004. |
| Respiratory Syncytial Virus | Borg et al., *Eur. Respir. J.* 21: 944-951, 2003; Gueudin et al., *J. Virol. Methods* 109: 39-45, 2003; Mentel et al., *J. Med. Microbiol.* 52: 893-896, 2003; Boivan et al., *J. Clin. Microbiol.* 42: 45-51, 2004. |
| Respiratory syncytial virus | Guedin et al., *J. Virol. Methods* 109: 39-45, 2003. |
| Severe acute respiratory syndrome coronavirus (SARS-CoV) | Poon et al., *Clin. Chem.* 50: 67-72, 2004; Drosten et al., *J. Clin. Microbiol.* 42: 2043-2047, 2004. |
| Varicella zoster virus | Espy et al., *J. Clin. Microbiol.* 38: 3187-3189, 2000; Furuta et al., *J. Clin. Microbiol.* 39: 2856-2859, 2001; Weidmann et al., *J. Clin. Microbiol.* 41: 1565-1568, 2003; Tipples et al., *J. Virol. Methods* 113: 113-116, 2003. |
| West Nile virus | Lanciotti et al., *J. Clin. Microbiol.* 38: 4066-4071, 2000 |

Examples of tests for detection and diagnosis of fungal pathogens are shown in Table 5.

TABLE 5

| Test | References/Products |
|---|---|
| *Aspergillus* | Loeffler et al., *J. Clin. Microbiol.* 40: 2240-2243, 2002; Kawazu et al., *J. Clin. Microbiol.* 42: 2733-2741, 2004 |
| *Blastomyces dermatitidis* | ACCUPROBE Blastomyces Dermatitidis Culture Identification Test, Gen-Probe Incorporated, San Diego, CA |
| *Candida* | Hsu et al., *J. Med. Microbiol.* 52: 1071-1076, 2003; Maaroufi et al., *J. Clin. Microbiol.* 42: 3159-3163, 2004 |
| *Coccidioides* | Bialek et al., *J. Clin. Microbiol.* 42: 778-783, 2004 |
| *Conidiobolus* | Imhof et al., *Eur. U. Clin. Microbiol. Infect. Dis.* 22: 558-560, 2003 |
| *Cryptococcus* | Bialek et al., *Clin. Diagn. Lab. Innumol.* 9: 461-469, 2002; Hsu et al., ''. |
| *Histoplasma* | Imhof et al., ''; Martagon-Villamil et al., *J. Clin. Microbiol.* 41: 1295-1298, 2003 |
| *Paracoccidioides* | Marques et al., *Mol. Genet. Genomics* 271: 667-677, 2004 |
| *Pneumocystis* | Larsen et al., *J. Clin. Microbiol.* 40: 490-494, 2002; Meliani et al., *J. Eukaryot. Microbiol.* 50(Suppl): 651, 2003 |
| *Stachybotrys* | Cruz-Perez et al., *Mol. Cell. Probes* 15: 129-138, 2001 |

Examples of known tests for detection and diagnosis of parasites are shown in Table 6.

TABLE 6

| Test | References |
|---|---|
| *Babesia* | Krause et al., *J. Clin. Microbiol.* 34: 2791-2794, 1996 |
| *Cryptosporidium* | Jiang et al., *Appl. Environ. Microbiol.* 71: 1135-1141, 2005 |
| *Encephalitozoon* | Wolk et al., *J. Clin. Microbiol.* 40: 3922-3928, 2002 |
| *Entamoeba* | Blessmann et al., *J. Clin. Microbiol.* 40: 4413-4417, 2002 |
| *Enterocyozoon* | Menotti et al., *J. Infect. Dis.* 187: 1469-1474, 2003 |
| *Giardia* | Verweij et al., *J. Clin. Microbiol* 42: 1220-1223, 2004 |
| *Leishmania* | Bossolasco et al., *J. Clin. Microbiol.* 41: 5080-5084, 2003Schulzetal., *J. Clin. Microbiol.* 41: 1529-1535, 2003. |
| *Plasmodium* | Lee et al., *J. Clin. Microbiol.* 40: 4343-4345, 2002; Farcas et al., *J. Clin. Microbiol.* 42: 636-638, 2004 |

TABLE 6-continued

| Test | References |
| --- | --- |
| *Toxoplasma* | Costa et al., *J. Clin. Microbiol.* 38: 2929-2932, 2000; Menotti et al. *J. Clin. Microbiol.* 41: 5313-5316, 2003 |
| *Trichomonas* | Hardick et al., *J. Clin. Microbiol.* 41: 5619-5622, 2003 |
| *Trypanosoma cruzi* | Cummings and Tarleton, *Mol. Biochem. Parasitol.* 129: 53-59, 2003 |

DNA prepared according to the present invention can also be used in genotyping, such as in prenatal screening, prediction of disease predisposition (e.g., hypertension, osteoporosis, early onset Alzheimer's, type I diabetes, and cardiovascular disease), toxicology, drug efficacy studies, and metabolic studies. Examples include tests for celiac disease, cystic fibrosis, HLA-B27, narcolepsy, and Tay-Sachs disease (Kimball Genetics Inc., Denver, Colo.). Tests to predict drug efficacy or dosing include, for example, ACE inhibitor responder assays, screening for DNA polymorphisms in CYP2D6 & CYP2C19 genes affecting rates of drug metabolism, screening for genes affecting tamoxifen metabolism, and genetic screening for irinotecan dosing. Genotyping of single nucleotide polymorphisms (SNPs) is disclosed by Hsu et al., *Clin. Chem.* 47:1373-1377, 2001 using a PCR-based assay and by Bao et al., *Nucl. Acids Res.* 33(2):e15, 2005 using a microarray platform. SNPs may be diagnostic of complex genetic disorders, drug responses, and other genetic traits. Tests used to guide cancer treatment include tests for BRCA-1, BRCA-2, and Her-2/Neu, including expression levels thereof. Min et al. (*Cancer Research* 58:4581-4584, 1998) disclose methods of screening sentinel lymph nodes for expression of tumor markers by RT-PCR. Identification of other cancer markers using nucleic acid technology is under investigation. Additional genetic tests are shown in Table 7.

TABLE 7

| Test | References/Products |
| --- | --- |
| Alpha hemoglobin | University of Washington Medical Center, Seattle, WA (www.labmed.washington.edu) |
| α-thalassemia | University of Washington Medical Center, Seattle, WA (www.labmed.washington.edu) |
| Beta hemoglobin | University of Washington Medical Center, Seattle, WA (www.labmed.washington.edu) |
| BRCA1 & 2 | Abbaszadegan et al., *Genet. Test.* 1: 171-180, 1997-98; Neuhausen and Ostrander, *Genet. Test.* 1: 75-83, 1997 |
| COL1A1 (osteoporosis risk) | Ralston et al., *PLoS Med.* 3: e90, 2006. |
| Cystic fibrosis | University of Washington Medical Center, Seattle, WA (www.labmed.washington.edu); INPLEX CF test, Third Wave Technologies, Inc., Madison, WI; Accola, U.S. Pat. No. 7,312,033 |
| Factor V Leiden Mutations | Roche Molecular Diagnostics, Pleasanton, CA; Nauck et al., *Clin. Biochem.* 33: 213-216, 2000. INFINITI System Assay for Factor V, AutoGenomics, Inc., Carlsbad, CA |
| Factor II Mutations | Roche Molecular Diagnostics, Pleasanton, CA; Nauck et al., *Clin. Biochem.* 33: 213-216, 2000. INFINITI Factor II assay, AutoGenomics, Inc., Carlsbad, CA |
| Fragile X | University of Washington Medical Center, Seattle, WA (www.labmed.washington.edu) |
| Friedreich ataxia | University of Washington Medical Center, Seattle, WA (www.labmed.washington.edu) |
| Growth hormone secretagogue receptor polymorphisms (obesity risk) | Kwitek et al., WO 2006/124664 |
| hemochromatosis | Hemochromatosis DNA Test, Kimball Genetics Inc., Denver, CO. |
| Hereditary hearing loss | University of Washington Medical Center, Seattle, WA (www.labmed.washington.edu) |
| Huntington disease screen | University of Washington Medical Center, Seattle, WA (www.labmed.washington.edu) |
| Myotonic dystrophy | University of Washington Medical Center, Seattle, WA (www.labmed.washington.edu) |
| Spinla dn bulbar muscular atrophy | University of Washington Medical Center, Seattle, WA (www.labmed.washington.edu) |
| Spinal cerebellar ataxia | University of Washington Medical Center, Seattle, WA (www.labmed.washington.edu) |
| Drug metabolism genes, e.g., UDP glucuronosyltransferase 1A1 alleles | INVADER UGT1A1 molecular assay (Third Wave Technologies, Inc.); Dorn, US 2008/0032305 A1. |
| p53 mutations | see U.S. Pat. No. 5,843,654 |
| rheumatoid arthritis: prediction of drug response & toxicity | Black et al. *Ann. Intern. Med.* 129: 716-718, 1998; van Ede et al., *Arthritis Rheum.* 44: 2525-2530, 2001 |
| Warfarin sensitivity | INFINITI Warfarin Assay and INFINITI Warfarin XP Assay (AutoGenomics, Inc., Carlsbad, CA); ESENSOR Warfarin Sensitivity Test (Osmetech Molecular Diagnostics, Pasadena, CA) |
| Prediction of anti-cancer drug sensitivity | Hayden et al., US 20080160533 A1; Muray et al., WO 2008/082643; Semizarov et al., WO 2008/082673 |

The present invention can also be used to detect cell-free DNA in plasma. Increased concentrations of cell-free genomic DNA are symptomatic of systemic lupus erythematosus, pulmonary embolism, and malignancy. Fetal DNA in maternal plasma or serum may be used for determination of gender and rhesus status, detection of certain haemoglobinopathies, and determination of fetal HLA status for potential cord blood donation. See, for example, Reed et al., *Bone Marrow Transplantation* 29:527-529, 2002. Abnormally high concentrations of circulating fetal DNA have been associated with trisomy 21 in the fetus (Lo et al., *Clin. Chem.* 45:1747-1751, 1999) and preeclampsia (Levine et al., *Am. J. Obstet. Gynecol.* 190:707-713, 2004). Methods for measuring fetal DNA in maternal plasma and serum are known in the art. See, for example, Lo et al., *Lancet* 350:485-487, 1997 and Lo et al., *Am. J. Hum. Genet.* 62:768-775, 1998. A particularly valuable application is the use of fetal DNA genotyping to determine fetal Rhesus D status using maternal plasma (Muller et al. *Transfusion* 48: 2292-2301, 2008).

DNA prepared according to the present invention can also be used for quantitation of residual white blood cells or WBC fragments in platelet concentrates by RT-PCR. See, for example, Lee et al., *Transfusion* 42:87-93, 2002; Mohammadi et al., *Transfusion* 44:1314-1318, 2004; and Dijkstra-Tiekstra et al., *Vox Sanguinis* 87:250-256, 2004.

The present invention is also applicable to veterinary medicine, including disease screening and diagnosis. For example, horses imported into Australia must be tested for equine influenza by PCR. Equine influenza can be transmitted to dogs (Crawford et al., *Science* 310:482-485, 2005).

The invention is further illustrated by the following non-limiting examples.

EXAMPLES

Example 1

A compression-sealed device was constructed as shown in FIGS. 3A and 3B. A silicone rubber block was die cut to create a serpentine channel (S-channel) that fit within the area of a standard glass slide. The channel had an overall footprint width of 25.3 mm and length of 75.5 mm. The device was assembled with glass microscope slides on both sides of the S-channel. Acrylic U-Channel was used to provide sufficient clamping pressure to prevent leaks between the glass and the silicone rubber. The two glass slides were separated by a distance of 62.5 mils (1587.5 µm), resulting in an S-channel volume (binding chamber volume)=1444 µL. The area covered by the S-channel was 910 mm$^2$. With two glass surfaces, the total glass area exposed to liquids=1820 mm$^2$, which is approximately equivalent to the area of one surface of a single glass slide (1910 mm$^2$). The exterior dimensions of the device without added fittings were approximately 76 mm by 30 mm by 10 mm (thickness).

Fluid is ported directly in and out of the S-channel using blunt-ended hypodermic needles inserted between the glass slides as shown in FIGS. 3A and 3B. In the alternative, 20-gauge thinwall tubing is inserted through pre-cored holes in the silicone rubber block to provide a leak proof seal (not shown).

Example 2

Twenty µL Subtilisin protease (10 mg/mL stock; obtained from Sigma-Aldrich) is mixed with 200 µL whole blood. 200 µL lysis reagent (6M guanidine hydrochloride, 50 mM citric acid pH 6.0, 20 mM EDTA, 10% Tween-20, 3% TRITON X-100) is added. The solution is mixed well using a pipettor, incubated at room temperature for 15 minutes, and 200 µL pure ethanol is added. The contents of the tube are mixed well.

Using a pipette, the entire sample is slowly loaded in to extraction device through one port. The sample is allowed to remain in contact with the glass surfaces for at least 1 minute and up to 20 minutes (most binding occurs in the first minute). The sample then is removed from the device. The binding chamber is filled with wash buffer 1 (lysis buffer without detergents diluted with equal volumes of water and 100% ethanol). The buffer is removed, and the wash is repeated two more times for a total of 3 washes. The binding chamber is then filled with wash buffer 2 (20 mM Tris-Cl pH7.0, 70% EtOH), then the buffer is removed. The wash 2 step is repeated 5 more times for a total of 6 washes.

To elute the bound DNA, 75-400 µL of TE (10 mM Tris pH 8.0, 1 mM EDTA) is loaded into the device and slowly swept through the binding chamber to its distal end, then back, and is then collected. The elution step may be repeated up to two times to recover additional nucleic acid. Multiple eluates can be combined or used separately.

Extracted DNA is functionally tested using a human GAPDH (Glyceraldehyde-3-Phosphate Dehydrogenase) PCR assay. A 10×PCR buffer is first prepared by mixing 0.1 mL 1 M Tris-Cl pH8.0, 0.03 mL 1 M MgCl$_2$, 0.5 mL 1M KCl, and 0.37 mL water. Primers (unpurified) G3001 (GAGATC-CCTCCAAAATCAAG; SEQ ID NO:6) and G3002 (CAAAGTTGTCATGGATGACC: SEQ ID NO:7) (obtained from Operon Biotechnologies, Inc., Huntsville, Ala. as dry powders) are resuspended in TE buffer to a concentration of 100 µM. Each PCR reaction contains 5 µL 10× buffer, 1 µL 10 mM dNTP mix (obtained from New England Biolabs, Ipswich, Mass.), 0.5 µL G3001 primer (SEQ ID NO:6), 0.5 µL G3002 primer (SEQ ID NO:7), 0.2 µL (5 units/µL) Taq polymerase (New England Biolabs), and water to 45 µL. A 5-µL sample of each eluate from the device being used is generally tested in each PCR reaction. More or less of each sample may be used by adjusting the amount of water added to the PCR reaction mix so that the final total volume of each reaction mix is 50 µL. PCR amplification is carried out in 0.2-mL thin-walled tubes. The temperature cycling profile consists of 1 minute at 94° C. (initial denaturation); 35 cycles of 1 minute 94° C., 1 minute 54° C., 1 minute 72° C.; with a final 2 minute 72° C. step. 7.5 µL of each sample is electrophoresed on a 2% agarose gel in 1×TAE (0.04M Tris, 0.02M Acetic Acid, 0.00M EDTA pH8.0) containing 0.2 µg/mL ethidium bromide. A 50-bp DNA ladder (New England Biolabs) is also run on the gel together with the PCR samples as a mobility marker. The GAPDH PCR appears as a band that is 267 bp in length.

Example 3

DNA extraction from whole blood and platelet-rich plasma were compared using glass slides (Nanassy et al., *Anal. Biochem.* 365:240-245, 2007) and a commercially available spin column kit comprising a glass fiber binding matrix mounted in a small column that fits in a microfuge tube (obtained from Qiagen). Commercially available buffers (Qiagen) were used in most of these studies except as noted for the platelet-rich plasma samples. Platelet rich plasma was prepared from whole blood by the Puget Sound Blood Center (PSBC) according to routine blood center protocols, and the whole blood was also drawn at the PSBC.

To isolate DNA on glass slides, 200-µL samples of whole blood or platelet-rich plasma were mixed with 400 µg of Proteinase K and 200 µL Buffer AL (which contains guanidine hydrochloride) and incubated at 55° C. for 15 minutes. After the incubation, 200 µl of 100% ethanol was added resulting in a total lysate volume of 600 µl. For some experiments the proportions of the input sample and of all other reagents were changed equally (e.g., if 400 µL of blood were being extracted instead of 200 µL, twice as much of all the other reagents was used in those preparations as well). For glass slide binding, 300 µL was layered onto a glass slide and incubated for 5 to 30 minutes at room temperature. For the higher volume lysates the incubation was repeated with 300 µL portions of the remaining lysate until all the lysate had been incubated onto the glass slides. The slides were then rinsed 2× with 0.5 mL Buffer AW1, and 2× with 0.5 mL Buffer AW2 (whole blood) or wash buffers 1 and 2 (PRP). After a brief centrifugation, the bound nucleic acid was eluted with 200 µL AE buffer (whole blood) or TE (PRP). All DNA concentrations were determined using the commercial PICOGREEN assay (Invitrogen Corp.) as per the manufacturer's instructions.

Figure 6B:
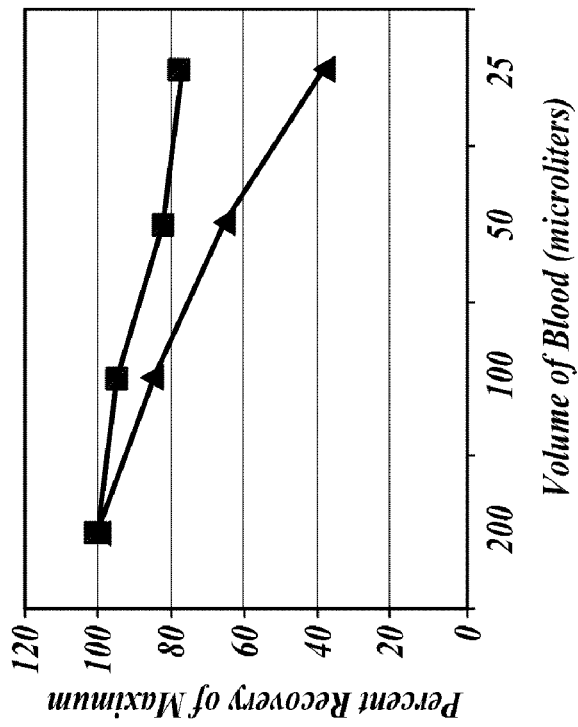
FIGS. 6A and 6B illustrate the recovery of DNA from glass slides (▲-▲) as compared to commercially available spin columns (■-■). DNA was isolated from platelet-rich plasma (FIG. 6A) or whole blood (FIG. 6B).
Figure 6A:
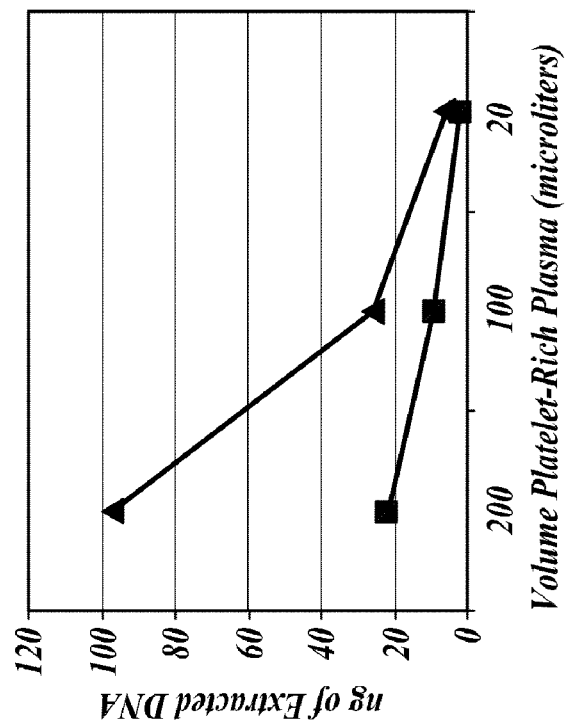

The glass slide technology was evaluated in comparison to the commercially available kit for performance in purification of DNA from blood samples, yield of purified DNA, and the ability to amplify the purified DNA by PCR. As shown in FIGS. 6A and 6B, flat glass slides gave a better yield from platelet-rich plasma, while porous glass gave a better yield from whole blood. Neither system extracted DNA in a purely linear fashion to the amount of input whole blood (i.e., 200 µL of blood did not yield twice as much DNA as 100 µL of blood).

The glass slide technology worked very successfully and reproducibly with platelet-rich plasma, with yields up to four times as high as those obtained with the spin column system (FIG. 6A). While not wishing to be bound by theory, it is believed that (despite their smaller surface area) the glass slides bind leukocyte DNA efficiently. Recovery from the flat surfaces may be improved in comparison to the thick porous substrate of the spin column. These results suggest that the glass slide system may actually be a more effective DNA purification tool when dealing with samples extracted from less complex blood fractions such as platelet-rich plasma.

DNA from both purification methods could be amplified by PCR using the HLA-DQ model system of Mohammadi et al. (*J. Clin. Microbiol.* 41:4796-4798, 2003). In general, the intensity of the gel bands obtained from the glass slide purification were darker than those of the spin column system, with the difference becoming more apparent at the higher volumes of eluate added to the PCR reaction. While 30 µL of the spin column eluate virtually completely inhibited PCR, an amplification product could still be obtained from the glass slide technology.

A number of PCR inhibitors from blood have been identified that may or may not be efficiently removed from blood by both methods. However, both methodologies use guanidine-based reagents for cell lysis. Guanidine is a potent inhibitor of PCR, and the level of inhibition seen may be a reflection of the contamination of the purified samples with guanidine. Samples of DNA from the flat glass surfaces were less contaminated than samples from column purification. Columns may trap lysis reagents which may be difficult to remove efficiently during the wash steps. In contrast, the flat glass surfaces do not trap lysis reagents. Washes can be done quickly and efficiently by flowing wash solutions over the entire surface of the slide.

Example 4

To characterize the X-channel device functionality, 20 µL Proteinase K was first mixed with 200 µL whole blood. 200 µL lysis reagent (28.7 g guanidine hydrochloride, 25 mL 0.1M sodium citrate pH 6.5, 2.5 mL 0.2M EDTA, 1 mL TRITON X-100, 3 mL TWEEN-20) was added. The solution was mixed well and incubated at 56° C. for 15 minutes. The solution was then cooled, and 200 µL ethanol was added. The contents of the tube were mixed, and the tube was centrifuged to spin down the condensate. A control extraction was also carried out essentially as described below except with commercially available reagents (obtained from Qiagen, Inc.). A third extraction was carried out using an S-channel device and QIAGEN reagents.

Starting with the X-channel device connected to a manifold assembly, the entire lysate as prepared above was slowly loaded into the device using a pipette tip (Rainin) sized to fit snugly into the first port. The first port was then covered with tape, and the sample was run through the device using an automated pumping protocol enabled by a peristaltic pump (Ismatec SA, Glattbrugg, Switzerland), a switching valve connected to the wash and elution reagents, and a computer program to control these devices. The binding chamber was then filled with wash buffer 1 (lysis reagent without detergents diluted with equal volumes of water and 100% ethanol). The buffer was removed, and the wash was repeated. The binding chamber was then filled with wash buffer 2 (prepared by mixing 50 parts wash 2 concentrate (10 mL 1M Tris, 5 mL 0.5M EDTA, and 2.93 g NaCl adjusted to pH 7.4 with 5N HCl) with 30 parts water and 20 parts 100% ethanol), and emptied thereafter. This wash was repeated four times. The channel was then subjected to air pumping over it as it was incubated at a slightly elevated temperature (37° C. or 42° C.) for up to 10 minutes to evaporate remaining wash 2 solution.

To elute the bound DNA, 75-200 µL of TE (10 mM Tris pH 8.0, 1 mM EDTA) was loaded into the device and slowly swept through the chamber to its distal end, then back. This eluate was collected for quantitation. Two initial studies with one X-channel device were performed on subsequent days, the first as described above except utilizing QIAGEN commercial reagents, and the second using the reagents disclosed above. The two preparations yielded quantities of 45 and 21 ng of DNA, respectively. The preparation with the S-channel device and the QIAGEN reagents yielded 24 ng of DNA.

To determine whether the DNA samples obtained from the X-channel device were of sufficient quantity and quality to be amplified by PCR, the DNA samples extracted above were used to amplify a portion of the HLA-DQA locus. As a control for DNA not purified on an X-channel device, another DNA sample extracted from 200 µL of whole blood using a commercially available kit (QIAMP Blood DNA Purification Kit; Qiagen, Inc.) according to the manufacturer's instructions was tested. The amplification was carried out using 1 to 2 ng of human genomic template DNA purified using the two different extraction methods (X-Channel and QIAGEN reagents and columns). The amplification protocol used was a standard published method, and the temperature cycles were 95° C. 15 seconds, 61.5° C. 1 minute for 35 cycles after an initial 2-minute, 95° C. denaturation cycle.

Figure 7:
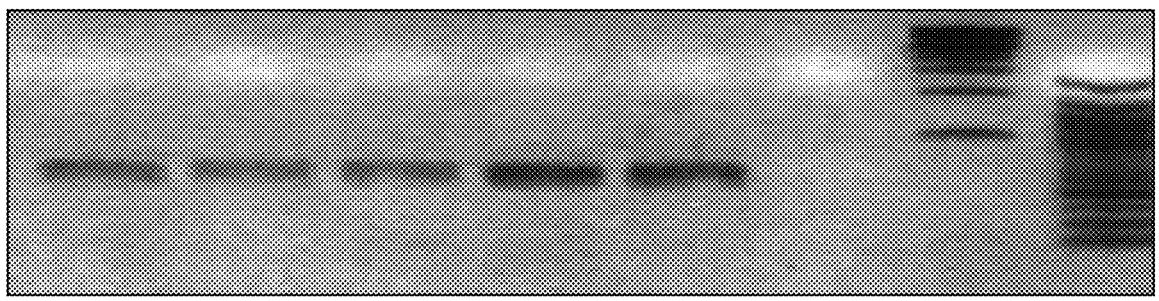
FIG. 7 illustrates the results of polymerase chain reaction amplification of DNA prepared using devices of the invention and a control extraction process.

Results of the amplification reactions are shown in FIG. 7. All visible PCR products represent amplified regions of the HLA-DQA locus. Lanes 7 and 8 are size markers (1 Kb and 50 bp ladders respectively). Lane 6 is a negative (no template) control lane where there should be no product. Template DNA used was as follows: Lane 1, 1 ng of DNA purified from an S-channel device; lanes 2 and 3, 2 ng and 1 ng of X-Channel purified DNA, respectively; lanes 4 and 5, 1 ng and 2 ng of QIAGEN column DNA, respectively.

In conclusion, the X-channel and S-channel devices purified DNA of sufficient quality to carry out PCR using standard methods and performed equivalently with respect to DNA amplification of DNA extracted using the commercial system.

Example 5

Experiments were carried out to optimize binding chamber width. In an initial study, six DNA capture devices were fabricated to test the effect of binding chamber width on yield. Each design consisted of a single, straight DNA binding chamber, rectangular in cross-section and of fixed width (2, 4, and 6 mm), and each design differed from the others only in the chamber width. During manufacturing and prior to addition of the glass slides, the devices were either left to cure at room temperature or heat treated at 42° C. on a hot plate for approximately 2-4 hours to test the effect of pre-heating the adhesive.

The six test devices (designated "R2," "R4," and "R6") were subsequently used to extract DNA from a single (larger volume) whole blood lysate in a side-by-side test with a device as shown in FIG. 5 ("v3.2") as disclosed below. The six test devices were vacuum degassed for approximately ten hours to explore the possibility of removing fouling material from the inside of each device. This vacuum degassing procedure had no effect on the performance of the v3.2 device, which was manufactured with an acrylic adhesive (8141; 3M Company), indicating that this adhesive may be viewed as a neutral variable. In contrast, post-manufacturing treatment of at least 8 hours vacuum degassing increased the yield of recovered DNA in devices manufactured using a different acrylic adhesive (467; 3M Company). Later studies showed that longer (>8 hours or so) vacuum degassing produced improved performance of the test devices with respect of DNA yield from whole blood DNA extractions.

In an initial test, the six vacuum-degassed test devices recovered between 8- and 35-fold more ng of DNA per $mm^2$ glass area compared to v3.2 design tested in parallel (Table 8). DNA recovered from the test devices ranged between 11 ng (narrow chamber) and 136 ng (wide chamber), values that represented a much better DNA yield per $mm^2$ glass area, at least for the latter. Both wider chambers also performed better than all the narrower ones. DNA purified from all of these devices was of good quality for PCR and homogeneous in amplification efficiency as tested using 2.5% of the first elution from each device (data not shown). Heat treatment of the adhesive during manufacturing did not appear to significantly affect recovery.

Example 6

The v3.2 device (FIG. 5) was compared to a commercially available spin column DNA extraction system (obtained from Qiagen, Inc.) for extracting DNA from apheresis platelets and plasma. Commercially available reagents (Qiagen, Inc.) were used throughout, and washes were carried out with 550-µL volumes two times for Assay Wash 1 and four times 550-µL volumes for Assay Wash 2 using an automated pumping system.

For extraction of DNA from apheresis platelets, 24 lysates were prepared essentially as disclosed in Example 15, each using 400 microliters of apheresis platelets. Each lysate was split, and half was applied to a spin column and half to a v3.2 device. Elutions were carried out with 200 µL Tris EDTA (10 mM/1 mM), and 0.1 µg/mL bisbenzimide dye was subsequently used to carry out DNA concentration measurements within the v3.2 device. Calibration curves were successfully defined by using the device as a cuvette to hold DNA standards with fluorescent bisbenzimide dye added. On-the-device DNA measurements did not work in this study after the extraction due to the presence of a substance that interfered with bisbenzimide dye fluorescence. Instead, measurement was carried out off the device using a commercially available dye (PICOGREEN, Invitrogen Corporation) according to the manufacturer's instructions. Fluorescence was determined using a bench top fluorimeter (SYNERGY HT Microplate Reader; BioTek Instruments, Inc., Winooski, Vt.). Subsequent amplification by PCR was carried out in the presence of the bisbenzimide dye, and amplification products were examined directly on agarose gels.

Twenty-two of twenty-four spin column preps extracted DNA with an average yield of 2.05±1.0 ng. Twenty-one of 24 v3.2 device preps extracted DNA with an average yield of 2.75±2.2 ng. PCR results reported below are based on amplification of 1% and 0.1% of total extracted DNA and were carried out using primers specific for the GAPDH gene as disclosed in Example 2. 22 of 24 spin column preparations successfully amplified based on endpoint agarose gel electrophoresis. Twenty-one of twenty-four v3.2 preparations successfully amplified.

For extraction of DNA from plasma, 14 lysates were prepared as disclosed above, each using 400 microliters of

TABLE 8

| Device | Post-manufacturing treatment | Number | ng DNA recovered | glass area $mm^2$ | ng recovered/ glass area | Volume (mL) |
| --- | --- | --- | --- | --- | --- | --- |
| untreated 2 mm | vacuum degas | 1 | 22 | 302 | 0.074 | 0.092 |
| untreated 4 mm | vacuum degas | 1 | 36 | 550 | 0.066 | 0.168 |
| untreated 6 mm | vacuum degas | 1 | 125 | 798 | 0.156 | 0.243 |
| heat treated 2 mm | vacuum degas | 1 | 11 | 302 | 0.037 | 0.092 |
| heat treated 4 mm | vacuum degas | 1 | 38 | 550 | 0.068 | 0.168 |
| heat treated 6 mm | vacuum degas | 1 | 136 | 798 | 0.170 | 0.243 |
| AC 08111 v3.2 | vacuum degas | 2 | 8 | 1256 | 0.006 | 0.526 |
| AC 08111 v3.2 | untreated | 4 | 7 | 1256 | 0.007 | 0.526 |

While not wishing to be bound by theory, although the volume of the devices was different, the DNA in the lysed blood was likely saturating the glass surfaces. If the DNA concentration to surface area was not saturating, then the larger volume devices would have been expected to extract more DNA. It was encouraging that these straight-channel designs gave purified DNA from whole blood that was suitable for use in PCR.

plasma. Each lysate was split, and half was applied to a spin column and half to a v3.2 device. Elutions were carried out with 200 µL Tris EDTA (TE; 10 mM/1 mM). A fluorescent dye (1×SYBR Green; Invitrogen Corporation) was then added to six of the samples to carry out on-the-device DNA concentration measurements. A second elution was also carried out for the v3.2 devices in the same manner as the first except no dye was added to any of the elution buffer. Calibration curves were successfully defined by using the device as a cuvette to hold DNA standards with fluorescent dye (SYBR Green) added. On-device DNA measurements did not work in this study and had to be carried out off the device using a commercially available dye (PICOGREEN, Invitrogen Corporation) according to the manufacturer's instructions.

Thirteen of the fourteen spin column preps extracted DNA with an average yield of 0.2±0.3 ng. Twelve of the fourteen v3.2 device preps extracted DNA with an average yield of 3.6±1.4 ng DNA. PCR results reported below are based on amplification of 2.5% of the total extracted DNA in either the first or second elutions and were carried out using primers specific for the GAPDH gene. For the spin column preparations, 13 out of 14 preparations successfully amplified based on amplification of 2.5% of the total extracted DNA carried out using primers specific for the GAPDH gene. For the v3.2 preparations, 12 out of 14 preparations successfully amplified based on amplification of 2.5% of the total extracted DNA in either the first or second elutions carried out using primers specific for the GAPDH gene. In this experiment, there was greater variability in amplification efficiency for the v3.2 device compared to spin columns. The PCR product bands if compared between the v3.2 devices and the spin columns qualitatively seemed less bright, and the failure rate of the PCR also seemed greater for these v3.2 preparations. Another observable trend when analyzing the two elutions using the same DNA concentration indicated poorer PCR performance in the second elution compared to the first elution for PCR amplification reactions with DNA extracted using the v3.2 devices.

Example 7

Two studies were carried out to compare side-by-side the DNA extraction capacity of two different device designs. Device v3.2 is illustrated in FIG. 5. Device B22 was of similar design but had a 6-mm wide binding channel with seven 180-degree bends and a volume of 0.712 mL. Second, it was important to test the ability to carry out on-device measurements of DNA concentration following DNA extraction. The samples were 0.2 mL of whole blood in the first study. In the second study the samples were either 0.2 mL whole blood or 500 ng of purified human DNA in phosphate buffered saline (PBS, pH 7.4).

Cell lysis and DNA capture were performed essentially as disclosed in Example 8, except commercially available reagents (obtained from Qiagen Inc.) and in-house reagents (essentially as disclosed in Example 5 using a 70% EtOH Assay Wash 2) were used. Prior to DNA purification some devices had been used as cuvettes (in an earlier study) to generate calibration curves specific for each device design. Fluorescence blank reads were carried out using fluorescent dye (SYBR Green; Invitrogen Corp.) and Tris-EDTA buffer with the devices used for on-device quantification. Commercially available spin columns (obtained from Qiagen Inc.) were used as a control with both reagent sets. Elution conditions are shown in Table 9.

DNA yields were quantified using 100 μL of each preparation and a commercially available quantitation kit (PICOGREEN dsDNA quantitation kit; Invitrogen Corp.) according to the manufacturer's instructions. This constituted the off-device quantification part of the experiment. The reagent type used did not seem to affect yields when used with either the B22 or the v3.2 device, however yields were better with the spin column when the QIAGEN reagents were used (Table 9).

TABLE 9

| Prep # | Device | Elution Volume | Elution Conditions | DNA Recovered (ng) |
|---|---|---|---|---|
| 338b | v3.2 | 200 μl | SYBR Green QIAGEN Reagents | 12 |
| 339b | v3.2 | 200 μl | no dye | 15 |
| 340 | B22 | 200 μl | SYBR Green | 15 |
| 341 | B22 | 200 μl | no dye | 15 |
| 342 | v3.2 | 200 μl | SYBR Green In-house Reagents | 11 |
| 343 | v3.2 | 200 μl | no dye | 16 |
| 344 | v3.2 | 200 μl | SYBR Green | 21 |
| 345 | B22 | 200 μl | no dye | 20 |
| 346 | Spin Column | 200 μl | no dye QIAGEN Reagents | 519 |
| 347 | Spin Column | 200 μl | no dye In-house Reagents | 372 |

In order to carry out on-device quantitation of the DNA samples, four devices from the same build lots (used in earlier preparations 330, 331, 336, and 337 as described below) were initially used as cuvettes and read in a bench top fluorimeter (SYNERGY HT Microplate Reader; BioTek Instruments, Inc., Winooski, Vt.). In order to generate standard curves specific to each device type, various DNA standards were quantified in the presence of 1× concentration fluorescent dye (SYBR Green) on-device using the fluorimeter by simply loading each device with the particular DNA standard or blank buffer sample (data not shown). By choosing one of the DNA calibration curves (device 336), the following correlations could be obtained between the on-device reads and the off-device reads (Table 10). It can be noted that using a "typical" calibration curve may not be a good approach towards calibrating the on-device reads since the reads for devices 342 and 344 were close to those obtained off-device but those for devices 338 and 340 were not as close.

TABLE 10

| Prep. No. | Device | Blank Reading (RFU) | Eluted Sample (RFU) | Off-device Quantitation (ng DNA) | On-device Quantitation (ng DNA) |
|---|---|---|---|---|---|
| 338 | v3.2 | 8559 | 16672 | 12 | 38 |
| 340 | B22 | 7641 | 17432 | 15 | 43 |
| 342 | v3.2 | 8855 | 12218 | 11 | 12 |
| 344 | v3.2 | 7343 | 13102 | 21 | 17 |

A second study was conducted to compare in side-by-side studies the capacity of the v3.2 and B22 devices with the same chamber height. Commercially available reagents (Qiagen Inc.) were used throughout. Prior to DNA purification some of the devices were used as cuvettes to generate DNA concentration fluorescence standard curves using fluorescent dye (either SYBR Green or BB dye).

Prior to DNA purification some devices had been used as cuvettes as disclosed above to generate calibration curves specific for each device design. Also, fluorescence blank reads were carried out using fluorescent dye (SYBR Green) and Tris-EDTA buffer with the devices used for on-device quantification. Spin columns (Qiagen Inc.) were used as a control with both reagent sets. The samples were read off-device on a 96-well black plate (COSTAR). A control set that was never input onto a device was included. There seemed to be no significant differences from the samples that were kept off the device to those that were read on-device for generation of calibration curve data (data not shown).

DNA yields were quantified using 100 μl of each preparation and a DNA binding fluorescent dye (SYBR Green). This constituted the off-device quantification part of the experiment. The yields obtained with the B22 devices may have been slightly higher for whole blood compared to the v3.2 devices (Table 11).

TABLE 11

| Prep. No. | Device | Analyte | RFU | ng/mL DNA per 200 μL analyzed | Recovered DNA (ng) |
|---|---|---|---|---|---|
| 330 | v.3.2 | human DNA | 2016 | 416 | 83 |
| 331 | B22 | human DNA | 2482 | 533 | 107 |
| 336 | v.3.2 | whole blood | 628 | 68 | 14 |
| 337 | B22 | whole blood | 906 | 138 | 28 |

By using the DNA calibration curves specific to each device, the following correlations could be obtained between the on-device reads (SYBR Green) and the off-device reads (Table 12).

TABLE 12

| Device | Post-extraction, on-device read | concentration (ng/mL) | DNA recovered (ng) | Off-device plate reads, DNA recovered (ng) |
|---|---|---|---|---|
| Re-purification of Human DNA | | | | |
| 330 | 43417 | 260 | 52 | 69 |
| 331 | 52902 | 362 | 72 | 91 |
| Extraction of DNA from blood | | | | |
| 336 | 19083 | 53 | 11 | 14 |
| 337 | 20840 | 103 | 21 | 28 |

By comparing the DNA concentration values obtained on and off the devices, the greatest difference measured in this experiment was about 2-fold. It is believed that there may be some degree of interference with fluorescence readings carried out following DNA extractions and that the accuracy of the on-device measurements can be increased by eliminating the interfering substance(s). Nonetheless, the object of obtaining an accurate measurement following DNA extraction was achieved by carrying out on-device readings with and without prior generation of calibration curves after elution of the DNA with buffer containing the DNA binding fluorescent dye (SYBR Green).

Example 8

An S-channel device constructed as shown in FIGS. 8A and 8B for device 400 and further comprising calibration wells (not shown) (designated "v4.0") was compared to commercially available spin column DNA extraction systems (QIAMP DNA Blood Mini Kit from Qiagen, Inc; NUCLEOSPIN Plasma XS from Macherey-Nagel GmbH & Co. KG) for extracting DNA from apheresis platelets and plasma. Commercially available reagents (obtained from Qiagen, Inc. and Macherey-Nagel) were used for each spin column system, and extractions were carried out according to the manufacturer's instructions. Reagents and extraction conditions disclosed in Example 12 were used for the v4.0 devices. Device washes were carried out with 1000 μl volumes three times for Assay Wash 1 and six times 1000 μl volumes for Assay Wash 2 using an automated pumping system. Drying times were 3 to 4 minutes for each device, and elution volumes were 100 μL for the spin column systems and 200 μL for the v4.0 devices, respectively. Only one elution was collected and subsequently analyzed for each extraction system.

For extraction of DNA from apheresis platelets, 22 lysates were prepared, sixteen using 400 microliters of apheresis platelets for extraction on the v4.0 devices and the Qiagen columns, and six using 240 microliters for extraction on the Machery-Nagel columns. All samples were lysed using subtilisin. V4.0 device elutions were carried out with 200 μL Tris EDTA (10 mM/1 mM), and fluorescent dye (1×SYBR Green) which was subsequently used to carry out DNA concentration measurements within the channel of the v4.0 device. Calibration wells built onto the v4.0 devices were successfully used to measure fluorescence from reference solutions of Tris EDTA (10 mM/1 mM) with fluorescent dye (1×SYBR Green) containing 0 and 100 ng/mL of purified human DNA by using the device as a cuvette to hold the DNA standards with fluorescent dye added. Measurements of DNA concentration in samples of the eluted nucleic acid for all three extraction systems were also carried out following extraction using the same fluorescent dye and human DNA for the standard curve. Subsequent amplification by PCR for the v4.0 device sample was carried out in the presence of the fluorescent dye, albeit at lower than 1× concentration, for the v4.0 device DNA samples.

The 6 Qiagen spin column preps extracted DNA from the apheresis platelets with an average yield of 1.2±0.4 ng DNA, or approximatively 171 white blood cell genome equivalents, assuming that one mammalian DNA genome equivalent equals 7 picograms (Wen et al., *Anal. Chem.* 80(17):6472-6479, 2008. The 6 Macherey-Nagel spin column preps extracted DNA from the apheresis platelets with an average yield of 0.3±0.3 ng DNA or approximatively 43 white blood cell genome equivalents. The 10 v4.0 device preps extracted DNA from the apheresis platelets with an average yield of 21.2±8.7 ng DNA or approximatively 3029 white blood cell genome equivalents.

PCR results reported here are based on amplification of described quantities of extracted DNA and were carried out using primers specific for the GAPDH gene as disclosed in Example 2. As disclosed above, an assumption was made for the calculation of genome equivalent values that one white blood cell has a DNA content of 7 picograms. We deduce that the lower the concentration of DNA amplified in the PCR reaction, the higher the purity of the extracted DNA with respect to the presence of PCR inhibitors. The number of white blood cell genome equivalent DNA concentrations tested by PCR for the v4.0 devices and Qiagen columns that amplified successfully are shown in Table 13.

TABLE 13

| v4.0 Device | Spin Column |
|---|---|
| 148 | 7 |
| 27 | 7 |
| 7 | 7 |
| 7 | 7 |
| 7 | |
| 27 | |
| 106 | |

For extraction of DNA from plasma, 19 lysates were prepared, each using 400 microliters of plasma. Nine preparations were carried out using the v4.0 device, 7 preparations were carried out using the Qiagen column system, and 3 preparations were carried out using the Macherey-Nagel column system. Commercially available reagents (obtained from Qiagen, Inc. and Macherey-Nagel) were used for each spin column system according to the respective manufacturer's instructions, and reagents disclosed in Example 12 were used for the v4.0 devices. Device washes were carried out with 1000 µl volumes three times for Assay Wash 1 and six times 1000 µl volumes for Assay Wash 2 using an automated pumping system. Drying times were 3 to 4 minutes for each device, and elution volumes were 200 µL Tris EDTA (10 mM/1 mM) for each spin column system or as described below for the v4.0 devices. Only one elution was collected and subsequently analyzed for each extraction system.

V4.0 device elutions were carried out with 200 µL Tris EDTA (10 mM/1 mM), and fluorescent dye (1×SYBR Green). which was subsequently used to carry out DNA concentration measurements within the channel of the v4.0 device. Calibration wells built onto the v4.0 devices were successfully used to measure fluorescence from reference solutions of Tris EDTA (10 mM/1 mM) with dye (1×SYBR Green) containing 0 and 100 ng/mL of purified human DNA by using the device as a cuvette to hold the DNA standards with fluorescent dye added. Measurement of DNA concentration in samples of the eluted nucleic acid for all three extraction systems were also carried out following extraction using the same fluorescent dye and human DNA for the standard curve. Subsequent amplification by PCR for the v4.0 device samples was carried out in the presence of the fluorescent dye, albeit at lower than 1× concentration.

The 7 Qiagen spin column preps extracted DNA from the plasma with an average yield of 3.9±0.4 ng DNA or approximatively 553 white blood cell genome equivalents. The 3 Macherey-Nagel spin column preps extracted DNA from the plasma with an average yield of 2.3±0.25 ng DNA or approximatively 333 white blood cell genome equivalents. The 9 v4.0 device preps extracted DNA from the plasma with an average yield of 17.3±5.8 ng DNA or approximatively 2472 white blood cell genome equivalents.

PCR results reported here are based on amplification of total extracted DNA from the plasma and were carried out using primers specific for the GAPDH gene as disclosed in Example 2. We deduce that the lower the concentration of DNA amplified in the PCR reaction, the higher the purity of the extracted DNA with respect to the presence of PCR inhibitors. The number of white blood cell genome equivalent DNA concentrations tested by PCR for the v4.0 device and Qiagen columns respectively that amplified successfully are shown in Table 14. High values shown for two of the v4.0 devices resulted from a pump malfunction that caused improper accumulation and subsequent drying of guanidine-containing wash buffers within the binding chambers of the devices. The remaining devices produced DNA of higher quality for amplification than the comparative spin columns.

TABLE 14

| v4.0 | Spin Column |
|---|---|
| 675 | 230 |
| 658 | 213 |
| 27 | 214 |
| 27 | 203 |
| 27 | |
| 7 | |
| 7 | |

Example 9

Three studies were carried out to demonstrate the quantification of extracted DNA directly on the v4.0 devices. It was important to test the ability to carry out on-device measurements of DNA concentration following DNA extraction. The sample was 0.4 mL of apheresis platelets in the first study. In the second study the sample was 0.4 mL plasma. In the third study 1000 ng of purified human DNA or no DNA (negative control) were offered for binding in Tris-EDTA buffer.

In-house reagents were used to carry out the purification on these devices essentially as described in Example 8, above. V4.0 device elutions were carried out with 200 µL Tris EDTA (10 mM/1 mM), and fluorescent dye (1×SYBR Green) which was subsequently used to carry out DNA concentration measurements within the channel of the v4.0 device. Measurement of DNA concentration in samples of the eluted nucleic acid for all three extraction systems were also carried out following extraction using the same fluorescent dye and human DNA for the standard curve. Fluorescence reads on the v4.0 devices were carried out using fluorescent dye and Tris-EDTA buffer in a bench top fluorimeter (SYNERGY HT Microplate Reader; BioTek Instruments, Inc., Winooski, Vt.). The v4.0 devices were fitted within a specially fabricated microtiter plate such that the top surface of the glass plate of the device was positioned evenly across the top of the microtiter plate. This arrangement allowed the binding chamber and calibration wells to align with plate reader.

Prior to carrying out actual DNA purifications, other v4.0 devices had been used as cuvettes (in an earlier study) to generate calibration curves specific for this device design. Two calibration wells built into the v4.0 devices were successfully used to measure fluorescence from reference solutions of Tris EDTA (10 mM/1 mM) with fluorescent dye (1×SYBR Green) containing 0, 50, 100, 200, 400, 600, 800, and 1000 ng/mL of purified human DNA by using the device as a cuvette to hold the DNA standards with fluorescent dye added. One calibration well always contained 0 ng/mL of DNA (blank), while the second calibration well usually contained a DNA solution of 100 ng/mL, except for the pilot calibration study where several DNA concentrations were studied as mentioned above. Each reading of the devices and the calibration wells was also performed at the same time as three independent positions within the binding chamber were read containing the same DNA solution and concentration as tested in the second calibration well. The DNA samples were also read off-device on a 96-well black plate (COSTAR). A control set that was never input onto a device was included for that measurement. The data shown below (Table 15; values are relative fluorescence units) indicate that the fluorescence values obtained on the devices within the calibration wells or at three independent positions within the binding chamber corresponded closely to the fluorescence values obtained off the devices. Moreover, the calibration blank reported a low background fluorescence value throughout the experiment as a negative control. These results demonstrate that device can be used as optical cuvette for quantitating nucleic acids.

TABLE 15

| Calibration Well | Blank Well | Analytical Wells Average (+/− SD; n = 3) | Off-device Readings |
|---|---|---|---|
| 1298 | 1356 | 1195 +/− 1.4 | 243 |
| 4411 | 2776 | 3506 +/− 22.1 | 2280 |
| 6243 | 2808 | 5105 +/− 38.8 | 3723 |
| 10686 | 2939 | 9174 +/− 198.0 | 7306 |

TABLE 15-continued

| Calibration Well | Blank Well | Analytical Wells Average (+/− SD; n = 3) | Off-device Readings |
|---|---|---|---|
| 15804 | 3072 | 14337 +/− 362.4 | 9047 |
| 20976 | 3225 | 19434 +/− 471.6 | 16082 |
| 30254 | 3275 | 28851 +/− 425.2 | 25185 |

DNA yields for extracted DNA from the three studies as outlined above were quantified using 25 µL of each preparation and fluorescent dye essentially as described in Example 8, but with the substitution of 1×SYBR Green dye for PICOGREEN dye. This constituted the off-device quantification part of the experiment. Immediately following each extraction the devices containing the 200 µL of Tris-EDTA elution buffer with fluorescent dye were read in a bench top fluorimeter (SYNERGY HT Microplate Reader; BioTek Instruments, Inc., Winooski, Vt.). The calibrator wells containing 100 ng/mL of DNA and a 0 ng/mL (blank) solution in the same Tris-EDTA elution buffer with fluorescent dye were used to calculate the DNA concentration of the elution buffer following extraction.

The apheresis platelet extraction experiment yielded the values shown in Table 16 on and off the device. For off-device quantitation ("Plate Read"), a 25-microliter aliquot was removed from the device, put into a microtiter plate well, and read with fluorescent dye (1×SYBR Green) as previously disclosed.

TABLE 16

| On-device Calculated Concentration (ng/ml) | Plate Read Concentration (ng/ml) |
|---|---|
| 223 | 131 |
| 331 | 162 |
| 179 | 90 |
| 269 | 148 |
| 87 | 27 |
| 332 | 207 |
| 139 | 276 |
| 231 | 265 |
| 219 | 157 |
| 193 | 124 |

As shown in Table 17, the plasma extraction experiment yielded the following values on and off the device:

TABLE 17

| On-device Calculated Concentration (ng/ml) | Plate Read Concentration (ng/ml) |
|---|---|
| 263 | 126 |
| 182 | 86 |
| 119 | 71 |
| 106 | 73 |
| 97 | 57 |
| 159 | 74 |

TABLE 17-continued

| On-device Calculated Concentration (ng/ml) | Plate Read Concentration (ng/ml) |
|---|---|
| 111 | 44 |
| 276 | 124 |

The pure DNA extraction or re-purification experiment and negative control (mock) extraction experiment yielded values of 177 ng/mL and 147 ng/mL on and off the device, respectively. The mock extraction experiment yielded a fluorescence value of 318 units when measured off the device versus the blank value of 259 units obtained from the standard curve in the standard microtiter plate-based fluorescence assay. On-device reads with the mock extraction experiment yielded a fluorescence value of 1790 units versus a blank value of 1819 units obtained from the calibration well with a 0 ng/mL DNA solution. These values do not rule out that these eluates may contain an interfering substance that could be affecting the dye solution. However, the expected error from any such interfering substance is low as the data above indicate.

By comparing the DNA concentration values obtained on and off the devices, the greatest difference measured in this experiment was about 2-fold. The object of obtaining a quantitative measurement following DNA extraction is achieved by carrying out on-device reads, without prior generation of calibration curves, after elution of the DNA with buffer containing the fluorescent dye.

Example 10

Experiments were conducted to develop methods for detecting the presence of pathogens (whether bacterial, viral, or other) in samples wherein only trace amounts of pathogen nucleic acids are present. A model assay for detecting *E. coli* DNA in water was based on a published (Frahm and Obst, *Journal of Microbiological Methods* 52:125, 2003) real-time PCR assay for the detection of *E. coli* DNA. The assays utilized probe-based (using dual labeled probes (TAQMAN probes; obtained from Applied Biosystems, Foster City, Calif.) or real-time fluorescence-based (using SYBR Green; Invitrogen) detection of amplification. This assay was modified to test the lower limit of detection when an S-channel device was used to re-purify bacterial DNA.

*E. coli* bacterial DNA from strain ATCC11303 type B was obtained from MP Biomedicals, Solon, Ohio, catalog number 101503, with original concentration of 1 mg/mL in water. The *E. coli* DNA was diluted directly with DEPC-treated water (FLUKA: Sigma-Aldrich, St. Louis, Mo.). Ten-fold serial dilutions were prepared ranging from 1 mg/mL to 1 pg/mL prior to amplification.

DNA was extracted on a v4.0 device essentially as disclosed in Example 12 with the omission of protease.

Primers and probes (Table 18) were obtained from Integrated DNA Technologies, Coralville, Iowa. Tm shown for primers 784F and 866R were specified by the manufacturer. For probe EC87, Tm was determined experimentally using a complementary oligonucleotide to the probe sequence.

TABLE 18

| Function | Name | Sequence (5'-3') and Labels | Conc. (nM) | Tm (° C.) |
|---|---|---|---|---|
| Forward Primer | 784F | GTG TGA TAT CTA CCC GCT TCG C (SEQ ID NO: 1) | various | 61.7 |
| Reverse Primer | 866R | AGA ACG GTT TGT GGT TAA TCA GGA (SEQ ID NO: 2) | various | 61.7 |

TABLE 18-continued

| Function | Name | Sequence (5'-3') and Labels | Conc. (nM) | Tm (° C.) |
|---|---|---|---|---|
| Fam probe | EC807 | TCG GCA TCC GGT CAG TGG CAG T (SEQ ID NO: 3)* | 200 | 73.8 |

*Probe EC807 (SEQ ID NO: 3) was labeled at the 5'-end with FAM, a tetrachlorofluorescein moiety, and at the 3'-end with a non-fluorescent quencher (BLACK HOLE QUENCHER from Biosearch Technologies, Novato, CA) to quench the FAM moiety. See, Frahm and Obst, ".

For the probe-based quantification, probes and primers were used at the following concentrations: 784F (SEQ ID NO:1), 900 nM; 866R (SEQ ID NO:2), 300 nM; and EC807 probe (SEQ ID NO:3), 200 nM. For fluorescent dye-based detection of amplification, the primers were used as follows: 784F (SEQ ID NO:1), 900 nM; 866R (SEQ ID NO:2), 900 nM with the fluorescent dye used at a 0.5× concentration.

PCR reactions comprised primers and templates as disclosed above. PCR reagent mixes were obtained from commercial suppliers. Reactions were run with a denaturing step at 95° C. for 10 minutes, followed by 40 cycles of 95° C. for 15 seconds and 60° C. for 1 minute.

PCR products were detected by measuring the value of the relative amount of the reporter's (probe or dye) fluorescence, caused by template-dependent nucleolytic degradation of the internally quenched probes. A threshold cycle Ct was defined for each PCR reaction as the amplification cycle where the increasing fluorescence signal first exceeded the background fluorescence (baseline); or as the fluorescent signals in the standard quantitation curve were closer to a straight line. Different amplification profiles for given DNA concentrations were then compared by their respective Ct, and the value of the relative DNA amount input into the PCR reaction was thereby determined. Verification of endpoint PCR results was also performed by electrophoresis on agarose gels (REDTRACK Precast Agarose Gels obtained from Biomoles, Seattle, Wash.). The agarose concentration used was usually 3% or 2%.

The specificity of the probe-based detection assay and dye-based assay was determined by using a 10-fold series dilution of pure *E. coli* DNA with concentrations ranging from 1 pg/mL1 mg/mL. The sensitivity of the assay when using probe EC807 (SEQ ID NO:3) was 10 pg/mL.

The Ct values detected were mostly ranging from 13-33. The Ct value of the negative control sample was usually more than 33 and could be affected by contaminating *E. coli* DNA levels in the various commercially obtained PCR reagent mixtures (TAQ SUPERMIX; obtained from Bio-Rad Laboratories, Hercules, Calif. or Quanta Biosciences, Inc., Gaithersburg, Md.) used.

Initial realtime PCR results testing for bacterial DNA using a PCR reagent mix obtained from Dr. John Meschke, University of Washington, showed the lower limit of detection of the assay to be 10 pg/mL. A separate test with a commercially obtained reagent mix (Bio-Rad Laboratories) showed lesser sensitivity of the assay at 100 pg/mL, presumably due to contaminating *E. coli* DNA present in the commercial reagents. Supporting data for this presumption is that the Ct value of the negative control sample is zero in realtime PCR and negative in agarose gel analysis when a cleaner reagent mix (obtained from Dr. Meschke and confirmed as being DNA-free) was used. A verification test was performed by filtering commercial Taq Supermix (Bio-Rad Laboratories) through a cellulose membrane filter (MICROCON YM-100 centrifugal filter unit; Millipore, Billerica, Mass.) according to the manufacturer's instructions followed by agarose gel qualification analysis. This verification test of resultant no-template-control (NTC) PCR product bands showed qualitatively less PCR product DNA and significantly reduced nonspecific reaction. The NTC controls obtained from two commercial reagent mixes (obtained from Bio-Rad Laboratories and Quanta Biosciences) both exhibited nonspecific reactions with $Ct \leqq 33$ and product bands by agarose gel analysis.

The use of carrier nucleic acid in detection of low levels of DNA was examined in the real-time PCR reaction. Fish DNA, human DNA, yeast tRNA (obtained from Sigma-Aldrich), and synthetic dA/dT (obtained from Sigma-Aldrich) were used at final concentrations ranging from 1 ng/mL to 1 mg/mL. The appropriate dA/dT concentration to be used in this assay was determined to be 30 ng/ml, and for tRNA, 10 ng/ml. The use of the carrier DNA was expected to normalize fluorescence signals during probe-based detection reactions where various quantities of DNA are amplified and to allow for direct, in-process quantification of the extracted nucleic acids on the device. Different carrier molecules were tested at set concentrations by titrating in carrier DNA along with the template, and a standard curve (dilution series) of *E. coli* DNA was run with the probe for each of the individual concentrations. The carrier concentration that least affected the standard curve was chosen as the preferred concentration with the understanding that as much as 50-100 ng/ml concentrations of carrier coming out of the extractions would simplify the on-device measurements from a signal-to-noise perspective. The dA/dT and tRNA carrier molecules were used at concentrations of 10 ng/ml and 30 ng/ml. The higher concentration used here allowed on-device quantitation of the extracted (carrier) DNA as shown in examples above. Genomic DNA was found to interfere with the PCR assays, probably due to non-specific binding of the primers resulting in greatly reduced sensitivity to *E. coli* DNA.

A protocol for washing the v4.0 device was implemented prior to using the device to re-purify bacterial DNA. The device was washed with 2-3 channel volumes of 70% EtOH, followed by another 2-3 channel volume wash with distilled sterile water. After washing, the device was dried for 5-10 minutes in a vacuum dessicator pumped with a standard oil lab vacuum pump.

The *E. coli* DNA standard curve generated using probe EC897 (SEQ ID NO:3) showed the lower limit of detection of the assay to be as low as 18 pg/mL. (The analysis of Ct value in this example was based primarily on locating the threshold slightly above the noise signals.) DNA isolated from the v4.0 device after washing as described previously was tested. The lower limit of detection of the assay was very similar to that of the DNA before purification on the v 4.0 device, and was as low as 18 pg/mL.

The assays described above point to the feasibility of using a synthetic carrier DNA molecule to track the DNA extraction process using fluorescent dye followed by direct downstream processing by real-time PCR for pathogen detection in the extracted water samples. Since the pathogen DNA would only be present in trace amounts, the carrier DNA helps validate the successful extraction of nucleic acids on the v4.0 device.

These experiments also showed that the *E. Coli* DNA contamination commonly found in commercial reagents affected the sensitivity of the assay. Simple mitigation methods were used, which enabled the researchers to achieve the desired sensitivity in this type of test. These mitigation methods included the use of RT-PCR grade water and purification of all reagents by ultrafiltration as disclosed by Reed et al., WO 2008/002882. The best results obtained over the course of these studies resulted in the sensitivity of the assay being measured down to 10 *E. coli* genome equivalents, which would translate to 10 colony forming units of bacteria if the bacterial DNA extraction protocols lyse and capture nucleic acid from every cell in that range.

Example 11

Nucleic acid sequence-based amplification was run on an S-channel device using a PCR fragment of the human GAPDH gene as a template. The template was generated using primers G3 Amp004 (AATTTAATACGACTCACTAT-AGGGATCATGAGTCCTTCCACGATACC; SEQ ID NO:4) and G3003 (AGCGAGATCCCTCCAAAATC; SEQ ID NO:5). Primer G3 Amp004 (SEQ ID NO:4) includes a T7 RNA polymerase promoter. Oligonucleotides were purified by HPLC and dissolved in TE at a concentration of 100 µM. A primer stock was prepared by mixing 5 µL or each primer solution, 375 µL of DMSO, and 115 µL or 50 mM Tris, pH 8.0.

A first set of experiments were run to determine if an S-channel device could be used as a reaction vessel for a NASBA reaction. All reagents were loaded onto and removed from the device with a 1-mL pipettor. An S-channel was filled with a bovine serum albumin (BSA; molecular biology grade obtained from Sigma-Aldrich, St. Louis, Mo.) solution at 1 mg/ml in TE to block the glass surface. After sitting for 30 minutes at room temperature, the blocking solution was removed and the channel was dried in a vacuum dessicator for 30 minutes at room temperature. After the drying period, no residual reagents were visible. A NASBA reaction mix (40 mM Tris-HCl pH 8.0, 12 mM $MgCl_2$, 70 mM KCl, 15% v/v DMSO, 5 mM DTT, 75 mM Sorbitol, 0.2 µM G3 Amp004 primer (SEQ ID NO:4), 0.2 uM G3003 primer (SEQ ID NO:5), 2 mM ribonucleotide mix, 1 mM deoxyribonucleotide mix, 80 µg/mL BSA (obtained from Sigma-Aldrich), 0.16 units *E. coli* RNaseH (obtained from New England Biolabs), 11 units AMV reverse transcriptase (obtained from Invitrogen Corp.), 60 units T7 RNA polymerase (obtained from New England Biolabs)) was then prepared that contained all of the NASBA components with or without the addition of 80 ng of the PCR fragment template, in a total volume of 50 µL. The reaction mix was carefully loaded into an S-channel device. The device was clamped into a heating block consisting of two heating elements mounted on a clamp and attached to a temperature controller, with the blocks positioned over the reaction mix in the channel. Internal channel temperature equilibrated to the set temperature in about 16 seconds. The reaction mix was incubated for 30 minutes at 42° C. As controls, equivalent NASBA reactions were run in standard 0.2-mL PCR tubes. When done, 7.5 µL of each reaction mix was run on a 2% agarose gel. Controls (no enzymes or no template) produced no visible reaction products. Complete reactions run in a tube or an S-channel device produced clearly visible reaction products (data not shown). The expected size double-stranded amplification product of 320 bp was obtained along with a faster migrating single-stranded RNA product that ran at around 200 bases. The RNA product ran somewhat anomalously in this gel system as its expected size was approximately 150 bases.

In a second set of experiments, the PCR template was first bound to the glass surface of the S-channel device. All reagents were loaded onto and removed from the device with a 1-mL pipettor. A NASBA reaction mix was then loaded into the channel to elute the bound template and amplify it. Controls included (1) a standard NASBA reaction without added template run in a standard 0.2-mL PCR tube in a total volume of 50 µL, (2) a standard NASBA reaction run in the presence of template run in a standard 0.2-mL PCR tube in a total volume of 50 µL, and (3) an S-channel device run as in the first set of experiments, above. Tube controls were incubated in a standard thermocycler set at 42° C. for 45 minutes.

To bind the template to the glass surface, 200 ng PCR template was mixed with 0.2 mL of a binding mix prepared by mixing 0.5 mL lysis buffer (6M Guanidine hydrochloride, 50 mM Citric acid pH6.0, 20 mM EDTA, 33% ethanol, 10% Tween-20, 3% Triton X-100), 0.5 mL water, and 0.5 mL ethanol. The template in the binding mix was loaded into the S-channel, and the template was allowed to bind to glass for 30 minutes at room temperature. The binding mix was removed, and a post-binding block was carried out by loading on a solution of the binding mix with BSA at 1 mg/mL. A second reaction was run under the same conditions but without added BSA. The post-block was allowed to sit for 15 minutes at room temperature and removed. The channel was then washed three times with Wash 1 (2M Guanidine HCl, 16 mM Citric Acid pH6.0, 6 mM EDTA, and 33% ethanol) and six times with Wash 2 (20 mM Tris pH7.0 and 70% ethanol). The channel was then dried under vacuum. A complete NASBA reaction mix (as above, but containing an additional 800 µg/mL BSA) without any added DNA and in a total volume of 50 µL was then loaded onto the device. The device was then incubated at 42° C. for 45 minutes. From each reaction, 7.5 µL was run on a gel. Control 1 (negative control, no template) produced no visible reaction products. Control 2 (positive control) showed a positive amplification reaction with the expected distribution of products. Control 3 (S-channel with added BSA) showed amplification. The NASBA reaction run on captured template without added BSA produced no amplification signal. The complete NASBA reaction run on captured template in the presence of 800 µg/mL BSA showed amplification, although at a lower intensity than the positive control. These results suggest that some loss of enzyme was still occurring and that a higher concentration of BSA is required to fully block enzyme adsorption to the glass.

Example 12

The binding capacity of the v4.0 device was studied. Lysis and wash buffers were as disclosed in Example 11. Samples were prepared by combining 400 µL of lysis buffer with 400 µL of water, 400 µL pure ethanol, and various amounts of purified human DNA (SIGMA; Sigma-Aldrich, St. Louis, Mo.). The samples were loaded with a pipette into v4.0 devices and incubated at room temperature for 30 minutes. The devices were then attached to an automated pumping system and washed three times with 1 mL each of wash 1, and six times with 1 mL each of wash 2. The devices were then dried under vacuum in a vacuum dessicator to remove residual ethanol. Bound DNA was eluted with three successive 200-µL washes with TE buffer. DNA in each sample was quantitated using a commercially available assay (PICOGREEN assay; Invitrogen Corp.) with minor modification. Reference DNA for quantitation was human DNA (SIGMA). Ten μL of each sample was analyzed.

Results are shown in Table 19. Total elution yields are the sum of the amount of recovered DNA in three successive 200-μL elutions of each device. The difference between the first elution volume and the total yield indicates that a significant amount of DNA was left on the device after the first elution step. Further, the total yield of DNA was linear over a wide input DNA concentration range (100 to 2000 ng). However, the first elution samples did not show a linear response in yield. The reason for this is unclear. The data further show that percent recovery may be higher at lower DNA concentrations, suggesting that dilute DNA concentrations may be more effectively purified than more highly concentrated samples.

TABLE 19

|  | DNA Recovered (ng) | | |
|---|---|---|---|
| Input DNA (ng) | First Elution | Total | % Recovery |
| 100 | 14 | 34 | 34 |
| 250 | 48 | 86 | 34 |
| 500 | 93 | 148 | 30 |
| 1000 | 183 | 259 | 26 |
| 2000 | 294 | 497 | 25 |

A similar experiment was performed using S-channel devices fabricated with 1"×3" glass slides. The experiment was carried out as above, except half the sample volume was used. Results are shown in Table 20. As opposed to the longer channel v4.0 devices, the shorter channel devices have a relatively flat response to input DNA. The reason for this is not known. However, this response may provide an advantage in situations where the amount of DNA needed for a downstream application may need to be limited.

TABLE 20

| Input DNA | Yield in Each Elution (ng) | | | |
|---|---|---|---|---|
| (ng) | First | Second | Third | Total (ng) |
| 50 | 8.7 | 3.5 | 0.8 | 13.0 |
| 125 | 8.3 | 2.9 | 1.3 | 12.6 |
| 250 | 7.3 | 4.0 | 0.8 | 12.1 |
| 500 | 8.6 | 1.8 | 1.4 | 11.8 |
| 1000 | 6.6 | 1.6 | 1.0 | 9.2 |

Example 13

DNA from whole blood was isolated using the v4.0 device and buffers disclosed in Example 12. Various amount of whole blood were mixed with water to a total volume of 400 μL. Then, 40 μL of 10 mg/mL Subtilisin (SIGMA) in TE was added, followed by 400 μL of lysis buffer. The mixture was incubated at room temperature for 15 minutes, then 400 μL of pure ethanol was added. The samples were then loaded into v4.0 devices by pipette. The devices were incubated for 10 minutes at room temperature to allow DNA binding. The devices were attached to an automated pumping system and washed three times with 1 mL each of wash 1, and six times with 1 mL each of wash 2. The devices were then dried under vacuum. Bound DNA was eluted with three successive 200-μL elutions using TE buffer. Ten μL of each eluate was quantitated using a commercially available assay (PICOGREEN assay; Invitrogen Corp.). Results are summarized in Table 21.

TABLE 21

| Input Amount of | Yield in Each Elution (ng) | | | Total |
|---|---|---|---|---|
| Blood (μL) | First | Second | Third | (ng) |
| 200 | 167 | 100 | 62 | 329 |
| 100 | 98 | 74 | 51 | 223 |
| 50 | 100 | 58 | 31 | 189 |
| 20 | 57 | 32 | 20 | 109 |

The data show that, as expected, lower amounts of input led to lower total yields. In order to gain some insight into the relative efficiency of capture, the total DNA yields were normalized to the input amount of blood. Table 22 summarizes the data.

TABLE 22

| Input Amount of Blood (μL) | Total Yield (ng) | Yield/ml of Whole Blood (ng) |
|---|---|---|
| 400 | 243 | 607 |
| 200 | 329 | 1644 |
| 100 | 223 | 2228 |
| 50 | 189 | 3771 |
| 20 | 110 | 5495 |

The normalized values increased with decreasing input amounts of blood. These data strongly suggest that the version 4 devices isolate DNA more efficiently at lower blood concentrations. The data suggest that an approximate linear response of yield is obtained in response to amount of blood input. The data in this example show that the v4.0 device efficiently isolated DNA from blood. As can be seen from Table 21, the second and third elutions contained significant amounts of DNA, making the total yield of DNA even more significant.

An undiluted 5-μL portion of each sample was tested in a GAPDH PCR assay, and all samples yielded the correct 267-bp PCR product.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A device comprising:
(i) a body member having a plurality of external surfaces and fabricated to contain a single continuous fluid pathway therethrough, the pathway consisting essentially of:
a first channel;
a second channel;
a binding channel between the first channel and the second channel, wherein the binding channel is open to one of the external surfaces of the body member;
a plurality of ports, wherein at least one of the ports is in fluid communication with the first channel distal to the binding channel, and wherein at least another of the ports is in fluid communication with the second channel distal to the binding channel; and
(ii) a glass member affixed to said one of the external surfaces of the body member to provide a first unmodified flat glass surface in fluid communication with the binding channel,
wherein the binding channel and glass member define a binding chamber effective for binding a heterogeneous population of nucleic acids, wherein the binding channel is a planar serpentine channel comprising a series of linear segments connected by curved segments having a narrower cross-section than the linear segments, and wherein the fluid pathway is essentially free of nucleic acid-specific binding sites.

2. The device of claim 1 wherein the binding channel is open to a second of the external surfaces of the body member and wherein the device further comprises a second glass member affixed to the second external surface of the body member to provide a second unmodified flat glass surface in fluid communication with the binding channel.

3. The device of claim 1 wherein the body member comprises a plurality of layered sheets of solid material selected from the group consisting of organic polymeric materials and glass.

4. The device of claim 1 wherein the body member comprises a plurality of layered sheets of solid material selected from the group consisting of polyethylene terephthalate, cellulose acetate, acrylic, polycarbonate, polypropylene, and polyvinylchloride.

5. The device of claim 1 wherein at least one of the ports comprises a Luer-lock fitting, an O-ring, a gasket, a tubing stub, or an elastomeric septum.

6. The device of claim 1 wherein the binding chamber is rectangular in cross-section.

7. The device of claim 1 further comprising a pump in fluid communication with the first port.

8. The device of claim 7 further comprising fluid distribution control means in fluid communication with the pump.

9. The device of claim 8 wherein the fluid distribution control means comprises a programmable computer.

10. The device of claim 1, consisting essentially of:
(i) a body member having a plurality of external surfaces and fabricated to contain a single continuous fluid pathway therethrough, the pathway consisting essentially of:
a first channel;
a second channel;
a binding channel between the first channel and the second channel, wherein the binding channel is open to first and second external surfaces of the body member; and
a plurality of ports, wherein at least one of the ports is in fluid communication with the first channel distal to the binding channel, and wherein at least another of the ports is in fluid communication with the second channel distal to the binding channel;
(ii) a first glass member affixed to the first external surface of the body member to provide a first unmodified flat glass surface in fluid communication with the binding channel; and
(iii) a second glass member affixed to the second external surface of the body member to provide a second unmodified flat glass surface in fluid communication with the binding channel,
wherein the binding channel, first glass member, and second glass member define a binding chamber effective for binding a heterogeneous population of nucleic acids, wherein the binding channel is a planar serpentine channel comprising a series of linear segments connected by curved segments having a narrower cross-section than the linear segments, and wherein the fluid pathway is essentially free of nucleic acid-specific binding sites.

11. A process for extracting nucleic acid from a biological sample comprising:
introducing a nucleic acid-containing sample into the binding chamber of the device of claim 1 via one of the ports;
allowing nucleic acid in the sample to bind to the unmodified flat glass surface;
washing the binding chamber to remove contaminants; and
eluting bound nucleic acid from the unmodified flat glass surface.

12. The process of claim 11 further comprising lysing a cell sample to prepare the nucleic acid-containing sample.

13. The process of claim 11 wherein the nucleic acid-containing sample contains human nucleic acid.

14. The process of claim 11 wherein the nucleic acid-containing sample contains non-human nucleic acid.

15. The process of claim 11 wherein the nucleic acid is DNA.

16. The process of claim 15 wherein the DNA is genomic DNA.

17. The process of claim 11 wherein bound nucleic acid is eluted with a buffer containing a fluorescent compound that exhibits a change in fluorescence intensity in the presence of nucleic acids.

18. The process of claim 11 wherein flow of liquid through the binding chamber is laminar.

19. The process of claim 11 comprising the additional step of amplifying the eluted nucleic acid.

20. The process of claim 19 wherein the amplifying step comprises isothermal amplification.

21. The process of claim 11 further comprising drying the washed binding chamber prior to eluting the bound nucleic acid.

22. A process for extracting nucleic acid from a biological sample comprising:
introducing a nucleic acid-containing sample into the binding chamber of the device of claim 1 via one of the ports;
allowing nucleic acid in the sample to bind to the unmodified flat glass surface;
washing the binding chamber to remove contaminants; and
drying the washed binding chamber.

23. A kit comprising:
    the device of claim 1; and
    a buffer in a sealed container, wherein the buffer is a lysis buffer, a wash buffer, or an elution buffer.

24. The kit of claim 23 wherein the buffer is an elution buffer comprising a fluorescent compound that exhibits a change in fluorescence intensity in the presence of nucleic acids.

25. The kit of claim 24 wherein the compound is a bis-benzimidine compound.

26. The kit of claim 23 further comprising a second buffer in a second sealed container, wherein the second buffer is a lysis buffer or a wash buffer.

27. The kit of claim 23 further comprising an instruction document.

\* \* \* \* \*

SEQUENCE LISTING

<160> NUMBER OF SEQ ID NOS: 7

<210> SEQ ID NO 1
<211> LENGTH: 22
<212> TYPE: DNA
<213> ORGANISM: Artificial Sequence
<220> FEATURE:

-continued

<223> OTHER INFORMATION: Synthetic Oligonucleotide

<400> SEQUENCE: 1
gtgtgatatc tacccgcttc gc                                            22

<210> SEQ ID NO 2
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 2
agaacggttt gtggttaatc agga                                          24

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 3
tcggcatccg gtcagtggca gt                                            22

<210> SEQ ID NO 4
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 4
aatttaatac gactcactat agggatcatg agtccttcca cgatacc                 47

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
agcgagatcc ctccaaaatc                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
gagatccctc caaaatcaag                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
caaagttgtc atggatgacc                                               20